US007811813B2

(12) United States Patent
Garren et al.

(10) Patent No.: US 7,811,813 B2
(45) Date of Patent: Oct. 12, 2010

(54) METHODS AND IMMUNE MODULATORY NUCLEIC ACID COMPOSITIONS FOR PREVENTING AND TREATING DISEASE

(75) Inventors: Hideki Garren, Palo Alto, CA (US); Peggy P. Ho, Cupertino, CA (US); Lawrence Steinman, Stanford, CA (US)

(73) Assignees: The Board of Trustees of the Leland Stanford Junior University, Palo Alto, CA (US); Bayhill Therapeutics, Inc., Palo Alto, CA (US)

( * ) Notice: Subject to any disclaimer, the term of this patent is extended or adjusted under 35 U.S.C. 154(b) by 1340 days.

(21) Appl. No.: 10/524,643

(22) PCT Filed: Nov. 21, 2003

(86) PCT No.: PCT/US03/37157

§ 371 (c)(1),
(2), (4) Date: Feb. 10, 2005

(87) PCT Pub. No.: WO2004/047734

PCT Pub. Date: Jun. 10, 2004

(65) Prior Publication Data

US 2005/0261215 A1 Nov. 24, 2005

Related U.S. Application Data

(60) Provisional application No. 60/428,643, filed on Nov. 21, 2002.

(51) Int. Cl.
*C12N 15/00* (2006.01)
(52) U.S. Cl. .................................................. 435/320.1
(58) Field of Classification Search .................. None
See application file for complete search history.

(56) References Cited

U.S. PATENT DOCUMENTS

| 6,194,388 | B1 | 2/2001 | Krieg et al. | |
|---|---|---|---|---|
| 6,225,292 | B1 | 5/2001 | Raz et al. | |
| 6,610,661 | B1 * | 8/2003 | Carson et al. | 514/44 |
| 6,949,520 | B1 * | 9/2005 | Hartmann et al. | 514/44 |
| 7,544,669 | B2 * | 6/2009 | Fontoura et al. | 514/44 R |
| 7,579,328 | B2 * | 8/2009 | Steinman et al. | 514/44 R |
| 7,585,843 | B2 * | 9/2009 | Garren et al. | 514/14 |
| 7,704,970 | B2 * | 4/2010 | Steinman et al. | 514/44 R |
| 2002/0164341 | A1 | 11/2002 | Davis et al. | |
| 2003/0181406 | A1 | 9/2003 | Schetter et al. | |
| 2005/0002953 | A1 * | 1/2005 | Herold | 424/186.1 |
| 2009/0208481 | A1 * | 8/2009 | Steinman et al. | 424/94.64 |
| 2009/0264515 | A1 * | 10/2009 | Fontoura et al. | 514/44 R |
| 2009/0281170 | A1 * | 11/2009 | Fontoura et al. | 514/44 R |
| 2010/0048679 | A1 * | 2/2010 | Garren et al. | 514/44 R |
| 2010/0074907 | A1 * | 3/2010 | Mi et al. | 424/172.1 |

FOREIGN PATENT DOCUMENTS

WO   WO 01/51626 A2   7/2001

OTHER PUBLICATIONS

Sugiyama et al, J. Immunology, 2005, 174:2273-2279.*
Puig et al, Nucleic Acids Research, 2006, 34/22:6488-6495.*
Dalpke et al, Immunology, 2002, 106:102-112.*
Ballas et al, J. Immunology, 2001, 167:4878-4886.*
Krieg et al, Nature, 2002, 374:546-549 abstract only.*
Lipford et al, Immunology, 2000, 101:46-52.*
Shen et al, Antisense & Nucleic Acid Drug Development, 2002, 12:155-164.*
Obermeier et al, Eur. J. Immunol., 2002, 32:2084-2092.*
Wooldridge et al, Blood, 1997, 89/8:2994-2998.*
Whitmore et al, Cancer Immunol. Immunother., 2001, 50:503-514.*
Lee et al, J. Immunol., 2000, 165:3631-3639.*
Mempl et al, Immunology Letters, 2003, 89:47-57.*
Zhang et al, J. Neuroimmunology, 2005, 161:68-77.*
Ho et al, J. Immunology, 2003, 171:4920-4926.*
Van Uden, Dissertation Abstracts International, 2001, 62/5B:2248 abstract only.*
Boccaccio et al, International Immunology, 1999, 11/2:289-296.*
Oxienius et al, I. Virology, 1999, 73/5:4120-4126.*
Lobell et al, J. Immunology, 1999, 163:4754-4762.*
Krieg et al, PNAS, 1998, 95:12631-12636.*
Krieg, Handbook of Experimental Pharmacology, 1998, 131:243-262.*
Ho et al, Autoimmunity, Dec. 2006, 39/8:675-682.*
Bar-Or et al, Arch. Neurol., 2007, 64/10:1407-1415.*
Garren et al, Ann. Neurol., 2008, 63:611-620.*
Robinson et al, Nature Biotechnology, Sep. 2003, 21/9:1033-1039.*
Solvason et al, I. Immunol., 2008, 181:8298-8307.*
Ho et al., "An immunomodulatory GpG oligonucleotide for the treatment of autoimmunity via the innate and adaptive immune systems", *J. Immunology*, 2003, pp. 4920-4926, vol. 171.
Klinman et al., "CpG motifs present in bacterial DNA rapidly induce lymphocytes to secrete interleukin 6, interleukin 12, and interferon γ", *Proc Nat. Acad. U.S.A.*, 1996, pp. 2879-2883, vol. 93.
Krieg et al., "CpG motifs in bacterial DNA trigger direct B-Cell activation", *Nature*, 1995, pp. 546-549, vol. 374.
Martin-Orozco et al., "Enhancement of antigen-presenting cell surface molecules involved in cognate interactions by immunostimulatory DNA sequences", *Int. Immunol.*, 1999, pp. 1111-1118, vol. 11(7).

(Continued)

*Primary Examiner*—N. M Minnifield
(74) *Attorney, Agent, or Firm*—Townsend and Townsend and Crew LLP

(57) ABSTRACT

This invention relates to methods and compositions for treating or preventing disease comprising the administration of immune modulatory nucleic acids having one or more immune modulatory sequences (IMSs). The invention further relates to the means and methods for the identification of the IMSs for preventing or treating disease, more particularly the treatment and prevention of autoimmune or inflammatory diseases. The invention also relates to the treatment or prevention of disease comprising the administration of the immune modulatory nucleic acids alone or in combination with a polynucleotide encoding self-protein(s), -polypeptide(s) or -peptide(s). The present invention also relates to methods and compositions for treating diseases in a subject associated with one or more self-protein(s), -polypeptide(s) or -peptide(s) that are present in the subject and involved in a non-physiological state.

11 Claims, 23 Drawing Sheets

OTHER PUBLICATIONS

Sparwasser et al., "Bacterial DNA and immunostimulatory CpG oligonucleotides trigger maturation and activation of murine dendritic cells", *Eur. J. Immunol.*, 1998, pp. 2045-2054, vol. 28.

Stacey et al., "Immunostimulatory DNA as an adjuvant in vaccination against *Leishmania major*", *Infection and Immunity*, 1999, pp. 3719-3726, vol. 67(8).

Yi et al., "Rapid Immune Activation by CpG Motifs in Bacterial DNA", *J. Immunol.*, 1996, pp. 5394-5402, vol. 157.

Zeuner et al., "Reduction of CpG-Induced Arthritis by Suppressive Oligodeoxynucleotides" *Arthritis and Rheumatism*, 2002, pp. 2219-2224, vol. 46(8).

Lenert, Petar et al.; "CpG Stimulation of Promary Mouse B Cells is Blocked by Inhibitory Oligodeoxyribonucleotides at a Site Proximal to NF-κB Activation"; 2001, *Antisense & Nuclecic Acid Drug Development*, vol. 11, pp. 247-256.

Yew, Nelson S. et al.; "Reduced Inflammatory Response to Plasmid DNA Vectors by Elimination and Inhibition of Immunostimulatory CpG Motifs"; 2000, *Molecular Therapy*, vol. 1, No. 3, pp. 255-262.

Invitrogen: pVAX1 (Catalog No. V260-20) version B 010124/25-0256, 1998, 15 pages.

* cited by examiner

US 7,811,813 B2

METHODS AND IMMUNE MODULATORY NUCLEIC ACID COMPOSITIONS FOR PREVENTING AND TREATING DISEASE

CROSS-REFERENCE TO RELATED APPLICATIONS

This is a U.S. National Stage Application under 35 U.S.C. 371 of International Application No. PCT/US2003/037157, filed on Nov. 21, 2003, which claims the benefit of U.S. Provisional Patent Application No. 60/428,643, filed Nov. 21, 2002, the complete disclosure of which is incorporated herein by reference.

STATEMENT AS TO RIGHTS TO INVENTIONS MADE UNDER FEDERALLY SPONSORED RESEARCH OR DEVELOPMENT

This invention was made with Government support under contract NS18235 awarded by the National Institutes of Health and under contract 1R43AI51135-01A1. The Government has certain rights in this invention.

BACKGROUND OF THE INVENTION

1. Field of the Invention

This invention relates to methods and compositions for treating or preventing disease comprising the administration of immune modulatory sequences. The invention further relates to the means and methods for the identification of the immune modulatory sequences for preventing or treating disease, more particularly the treatment and prevention of autoimmune disease or inflammatory diseases. The invention also relates to the treatment or prevention of disease comprising the administration of the immune modulatory sequences alone. The invention also relates to the treatment or prevention of disease comprising the administration of the immune modulatory sequences in combination with a polynucleotide encoding self-protein(s), -polypeptide(s) or -peptide(s). The invention further relates to the treatment or prevention of disease comprising the administration of the immune modulatory sequences in combination with self-molecules, such as self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s). The invention also relates to the treatment or prevention of disease comprising the administration of the immune modulatory sequences in combination with one or more additional immune modulatory therapeutics.

The present invention also relates to methods and compositions for treating diseases in a subject associated with one or more self-protein(s), -polypeptide(s) or -peptide(s) that are present in the subject and involved in a non-physiological state. The present invention also relates to methods and compositions for preventing diseases in a subject associated with one or more self-protein(s), -polypeptide(s) or -peptide(s) that are present in the subject and involved in a non-physiological state. The invention also relates to the administration of a combined therapy comprising an immune modulatory sequence and a polynucleotide encoding a self-protein(s), -polypeptide(s) or -peptide(s) present in a non-physiological state and associated with a disease. The invention also relates to modulating an immune response to self-molecule(s) present in an animal and involved in a non-physiological state and associated with a disease. The invention is more particularly related to the methods and compositions for treating or preventing autoimmune diseases associated with one or more self-molecule(s) present in the animal in a non-physiological state such as in multiple sclerosis (MS), rheumatoid arthritis (RA), insulin dependent diabetes mellitus (IDDM), autoimmune uveitis (AU), primary biliary cirrhosis (PBC), myasthenia gravis (MG), Sjogren's syndrome, pemphigus vulgaris (PV), scleroderma, pernicious anemia, systemic lupus erythematosus (SLE) and Grave's disease. The invention is further particularly related to other diseases associated with one or more self-molecule(s) present in the animal in a non-physiological state such as osteoarthritis, spinal cord injury, peptic ulcer disease, gout, migraine headaches, hyperlipidemia and coronary artery disease.

2. Background

Autoimmune Disease

Autoimmune disease is any disease caused by adaptive immunity that becomes misdirected at healthy cells and/or tissues of the body. Autoimmune disease affects 3% of the U.S. population, and likely a similar percentage of the industrialized world population (Jacobson et al., *Clin Immunol Immunopathol*, 84, 223-43, 1997). Autoimmune diseases are characterized by T and B lymphocytes that aberrantly target self-molecules, including but not limited to self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s), and derivatives thereof, thereby causing injury and or malfunction of an organ, tissue, or cell-type within the body (for example, pancreas, brain, thyroid or gastrointestinal tract) to cause the clinical manifestations of the disease (Marrack et al., *Nat Med*, 7, 899-905, 2001). Autoimmune diseases include diseases that affect specific tissues as well as diseases that can affect multiple tissues. This may, in part, for some diseases depend on whether the autoimmune responses are directed to a self molecule antigen confined to a particular tissue or to a self molecule antigen that is widely distributed in the body. The characteristic feature of tissue-specific autoimmunity is the selective targeting of a single tissue or individual cell type. Nevertheless, certain autoimmune diseases that target ubiquitous self molecules antigens can also affect specific tissues. For example, in polymyositis the autoimmune response targets the ubiquitous protein histidyl-tRNA synthetase, yet the clinical manifestations primarily involved autoimmune destruction of muscle.

The immune system employs a highly complex mechanism designed to generate responses to protect mammals against a variety of foreign pathogens while at the same time preventing responses against self-antigens. In addition to deciding whether to respond (antigen specificity), the immune system must also choose appropriate effector functions to deal with each pathogen (effector specificity). A cell critical in mediating and regulating these effector functions is the CD4+ T cell. Furthermore, it is the elaboration of specific cytokines from CD4+ T cells that appears to be one of the major mechanisms by which T cells mediate their functions. Thus, characterizing the types of cytokines made by CD4+ T cells as well as how their secretion is controlled is extremely important in understanding how the immune response is regulated.

The characterization of cytokine production from long-term mouse CD4+ T cell clones was first published more than 10 years ago (Mosmann et al., *J. Immunol.*, 136:2348-2357, 1986). In these studies, it was shown that CD4+ T cells produced two distinct patterns of cytokine production, which were designated T helper 1 (Th1) and T helper 2 (Th2). Th1 cells were found to selectively produce interleukin-2 (IL-2), interferon-gamma (IFN-gamma) and lymphotoxin (LT), while Th2 clones selectively produced IL-4, IL-5, IL-6, and IL-13 (Cherwinsid et al., *J. Exp. Med.*, 169:1229-1244, 1987). Somewhat later, additional cytokines, IL-9 and IL-10, were isolated from Th2 clones (Van Snick et al., *J. Exp. Med.*, 169:363-368, 1989) (Fiorentino et al., *J. Exp. Med.*, 170: 2081-2095, 1989). Finally, additional cytokines, such as IL-3, granulocyte macrophage colony-stimulating factor (GM-CSF), and tumor necrosis factor-alpha (TNF-alpha) were found to be secreted by both Th1 and Th2 cells.

Autoimmune disease encompasses a wide spectrum of diseases that can affect many different organs and tissues within the body as outlined in the table below. (See, e.g., Paul, W. E. (1999) *Fundamental Immunology*, Fourth Edition, Lippincott-Raven, New York.)

Current therapies for human autoimmune disease include glucocorticoids, cytotoxic agents, and recently developed biological therapeutics. In general, the management of human systemic autoimmune disease is empirical and unsatisfactory. For the most part, broadly immunosuppressive drugs, such as corticosteroids, are used in a wide variety of severe autoimmune and inflammatory disorders. In addition to corticosteroids, other immunosuppressive agents are used in management of the systemic autoimmune diseases. Cyclophosphamide is an alkylating agent that causes profound depletion of both T- and B-lymphocytes and impairment of cell-mediated immunity. Cyclosporine, tacrolimus, and mycophenolate mofetil are natural products with specific properties of T-lymphocyte suppression, and they have been used to treat SLE, RA and, to a limited extent, in vasculitis and myositis. These drugs are associated with significant renal toxicity. Methotrexate is also used as a "second line" agent in RA, with the goal of reducing disease progression. It is also used in polymyositis and other connective-tissue diseases. Other approaches that have been tried include monoclonal antibodies intended to block the action of cytokines or to deplete lymphocytes. (Fox, D. A. *Am. J Med.*, 99:82-88, 1995). Treatments for MS include interferon Beta and copolymer 1, which reduce relapse rate by 20-30% and only have a modest impact on disease progression. MS is also treated with immunosuppressive agents including methylprednisolone, other steroids, methotrexate, cladribine and cyclophosphamide. These immunosuppressive agents have minimal efficacy in treating MS. Current therapy for RA utilizes agents that non-specifically suppress or modulate immune function such as methotrexate, sulfasalazine, hydroxychloroquine, leflunamide, prednisone, as well as the recently developed TNF alpha antagonists etanercept and infliximab (Moreland et al., *J Rheumatol*, 28, 1431-52, 2001). Etanercept and infliximab globally block TNF alpha, making patients more susceptible to death from sepsis, aggravation of chronic mycobacterial infections, and development of demyelinating events.

In the case of organ-specific autoimmunity, a number of different therapeutic approaches have been tried. Soluble protein antigens have been administered systemically to inhibit the subsequent immune response to that antigen. Such therapies include delivery of myelin basic protein, its dominant peptide, or a mixture of myelin proteins to animals with experimental autoimmune encephalomyelitis (EAE) and humans with multiple sclerosis (Brocke et al., *Nature*, 379, 343-6, 1996); (Critchfield et al., *Science*, 263, 1139-43, 1994); Weiner et al., *Annu Rev Immunol*, 12, 809-37, (1994); administration of type II collagen or a mixture of collagen proteins to animals with collagen-induced arthritis and humans with rheumatoid arthritis (Gumanovskaya et al., *Immunology*, 97, 466-73, 1999); (McKown et al., *Arthritis Rheum*, 42, 1204-8, 1999), (Trentham et al., *Science*, 261, 1727-30, 1993); delivery of insulin to animals and humans with autoimmune diabetes (Pozzilli and Gisella Cavallo, *Diabetes Metab Res Rev*, 16, 306-7, 2000); and delivery of S-antigen to animals and humans with autoimmune uveitis (Nussenblatt et al., *Am J Ophthalmol*, 123, 583-92, 1997). A problem associated with this approach is T-cell unresponsiveness induced by systemic injection of antigen. Another approach is the attempt to design rational therapeutic strategies for the systemic administration of a peptide antigen based on the specific interaction between the T-cell receptors and peptides bound to major histocompatibility (MHC) molecules. One study using the peptide approach in an animal model of diabetes resulted in the development of antibody production to the peptide, (Hurtenbach U. et al, *J Exp. Med*, 177:1499, 1993). Another approach is the administration of TCR peptide immunization. See, for example, (Vandenbark A A et al., *Nature*, 341:541, 1989). Still another approach is the induction of oral tolerance by ingestion of peptide or protein antigens. See, for example, (Weiner H L, *Immmunol Today*, 18:335, 1997).

Immune responses to pathogens or tumors are currently altered by delivering proteins, polypeptides, or peptides, alone or in combination with adjuvants. For example, the hepatitis B virus vaccine contains recombinant hepatitis B virus surface antigen, a non-self antigen, formulated in aluminum hydroxide, which serves as an adjuvant. This vaccine induces an immune response against hepatitis B virus surface antigen to protect against infection. An alternative approach involves delivery of an attenuated, replication deficient, and/or non-pathogenic form of a virus or bacterium, each non-self antigens, to elicit a host protective immune response against the pathogen. For example, the oral polio vaccine is composed of a live attenuated virus, a non-self antigen, which infects cells and replicates in the vaccinated individual to induce effective immunity against polio virus, a foreign or non-self antigen, without causing clinical disease. Alternatively, the inactivated polio vaccine contains an inactivated or 'killed' virus that is incapable of infecting or replicating, and if administered subcutaneously, to induce protective immunity against polio virus.

Mechanisms of Initiation and Propagation of Immune Responses

Inflammatory Diseases Associated With "Nonself Molecules": Infection with microorganisms including mycoplasma, viruses, bacteria, parasites and mycobacteria leads to inflammation in target organs, and in some cases systemic inflammation. Prominent examples include bacterial septic arthritis, Lyme arthritis, infectious uveitis, and septic shock. As part of the inate immune system, inflammatory mediators such as components of the clotting cascade, bradykinins, and complement are activated and contribute to inflammation and morbidity. The immune response in infectious disease is directed against non-self molecules present in the microorganisms, including proteins, lipids, carbohydrates, and nucleic acids. Bacterial DNA containing certain motifs referred to as "CpG" motifs, defined in more detail below, are capable of initiating inflammatory responses in animal models. For example, injection of bacterial DNA or CpG motifs, both of which are non-self molecules, into synovial joints mimics many of the inflammatory signs and symptoms that characterize septic arthritis.

Inflammatory Diseases Associated With "Self Molecules": Many human diseases are associated with acute or chronic inflammation in the absence of any known infectious etiology. In these diseases, the immune system is active, causing the affected tissues to be inflamed and abnormally infiltrated by leukocytes and lymphocytes, but there appears to be no associated infection. Examples include osteoarthritis, coronary artery disease, Alzheimer's Disease, certain forms of dermatitis, gastritis, and pneumonitis. The predominant immune response is an innate immune response, in the absence of an adaptive immune response.

Autoimmune Diseases Associated With "Self Molecules": Dozens of autoimmune diseases have been described, including rheumatoid arthritis, systemic lupus erythematosus, multiple sclerosis, diabetes mellitus, psoriasis, and many others. Like the inflammatory diseases associated with self molecules above, the immune system is active, causing the affected tissues to be inflamed and abnormally infiltrated by leukocytes and lymphocytes, and there appears to be no associated infection. Unlike the inflammatory diseases associated with self molecules, a defining characteristic of autoimmune diseases is the presence of autoantibodies and/or T cells specific for self molecules expressed by the host. The mechanisms by which self molecules are selectively targeted by the host T and B lymphocytes are obscure. Some investigators have suggested that autoimmune diseases are triggered or exacerbated by infections with microbial pathogens. Stimulation with microbial CpG sequences is associated with an increased susceptibility to the development of animal models of autoimmune diseases such as EAE (Segal et al., *J. Immunology*, 158:5087, 1997) and SLE (Gilkeson et al., *J, immunology*, 142: 1482, 1989); however, there is little evidence to support the hypothesis that CpG sequences or microbial products can themselves trigger an autoimmune disease in an otherwise healthy animal, although inflammatory diseases can be induced. For example, several important experiments using gnotobiotic systems (i.e., animals raised in a germ free environment) have demonstrated that spontaneous development of autoimmune diseases occurs without exposure to naturally occurring microbes or microbial CpGs. Examples include development of autoimmune skin and genital disease in a germfree transgenic rodent model of ankylosing spondylitis (Taurog, J Exp Med, 180:2359, 1994); and development of lupus in 2 different models of SLE (Maldonadoi et al., J Immunol, 162: 6322, 1999; Unni et al., *J Rheum*, 2:35, 1975). An inducible model of SLE has also been described in which a single injection of any mouse strain with the hydrocarbon oil, pristane, leads to the development of SLE, characterized by the production of characteristic autoantibodies and immune complex-mediated kidney disease. Taken together, these experimental models suggest that spontaneous and inducible autoimmune diseases can develop in the absence of exposure to microbial DNA or CpGs.

Immunostimulatory sequences (ISS): The innate immune system is regarded as the first line of defense against microbes and pathogens. One of the most potent stimulants of the innate immune system is microbial DNA, which contains immunostimulatory sequences (ISS). The activation of innate immunity by specific immune stimulatory sequences in bacterial DNA requires a core unmethylated hexameric sequence motif consisting of 5'-purine-purine-cytosine-guanine-pyrimidine-pyrimidine-3' for stimulation in mice and 5'-purine-pyrimidine-cytosine-guanine-pyrimidine-pyrimidine-3' for stimulation in humans (Krieg et al., *Annu Rev. Immunol.*, 20:709-760, 2002). Bacterial DNA and synthetic oligodeoxynucleotides (ODN) containing this dinucleotide motif, referred to as "CpG" sequences, within an immune stimulatory sequence motif have the ability to stimulate B cells to proliferate and secrete IL-6, IL-10, and immunoglobulin (Krieg et al., *Nature*, 374:546-549, 1995; Yi et al., *J. Immunol*, 157:5394-5402, 1996). ISS DNA also directly activates dendritic cells, macrophages and monocytes to secrete Th1-like cytokines such as TNF-α, IL6, and IL12 and up-regulates the expression of MHC and costimulatory molecules (Klinman et al., *Proc. Nat. Acad. Sci. U.S.A.*, 93:2879-2883, 1996; Martin-Orozco et al., *Int. Immunol.*, 11:1111-1118, 1999; Sparwasser et al., *Eur. J. Immunol.*, 28:2045-2054, 1998). In mice, Toll-like receptor-9 (TLR-9) has been identified as the key receptor in the recognition of CpG motifs.

In vertebrate DNA, the frequency of CpG dinucleotides is suppressed to about one quarter of the predicted value, and the C in the CpG dinucleotide is methylated approximately 80% of the time. By contrast, bacterial DNA, like synthetic ODN, the C is not preferentially methylated in the CpG dinucleotide. Thus, bacterial DNA is structurally distinct from vertebrate DNA in its greater than 20-fold increased content of unmethylated CpG motifs. Numerous studies have established the unmethylated CpG motif as the molecular pattern within bacterial DNA that activates immune cells (Krieg et al., *Annu. Rev. Immunol.*, 20:709-760, 2002).

CpG DNA is recognized as a potent adjuvant for its ability to induce a strong antibody response and Th1-like T-cell response to such nonself antigens as hen egg lysozyme and ovalbumin (Chu et al., *J. Exp. Med.*, 186:1623-1631, 1997; Lipford et al., *Eur. J. Immunol.*, 27:2340-2344, 1997). Currently, CpG DNA and CpG ODN are being utilized as therapeutic vaccines in various animal models of infectious diseases, tumors, allergic diseases, and autoimmune diseases (Krieg et al., *Annu. Rev. Immunol.*, 20:709-760, 2002). The success of CpG as a vaccine relies heavily on its effectiveness of inducing a strong Th1-like response, and in some instances, redirecting a Th2 response to a Th1 response, such as in the allergic asthma model (Kline et al., *J. Immunol.*, 160:2555-2559, 1998; Broide et al., *J. Immunol.*, 161:7054-7062, 1998).

There has been significant attention given to the therapeutic applications of innate immune activation by CpG DNA. The potent non-antigen specific innate immune cell activation induced by CpG DNA is sufficient to protect mice against bacterial challenge, and even to treat established infections with intracellular pathogens (Agrawal et al., *Trends Mol. Med.*, 8:114-121, 2002). CpG DNA also induces innate immune resistance to tumors and the regression of established tumors in mice (Dow et al., *J. Immunol.*, 163:1552-1561, 1999; Carpenter et al., *Cancer Res.*, 59:5429-5432, 1999; Smith et al., *J. Natl. Cancer Inst.*, 90:1146-1154, 1998). The potent Th1 adjuvant effect of CpG DNA can even override preexisting Th2 immune responses; it has been used as an adjuvant for allergy vaccines, where it induces Th1 responses to antigens in the presence of a preexisting Th2 response, leading to decreased symptoms following subsequent allergen inhalation (Van Uden et al., *J. Allergy Clin. Immunol.*, 104:902-910, 1999).

Immunoinhibitory sequences (IIS): Inhibitors of immunostimulatory sequence oligodeoxynucleotide (ISS-ODN) have been used to inhibit the immunostimulatory activity of ISS-ODN, for example, to suppress the immunostimulatory activity of any ISS-ODN present in recombinant expression vectors particularly in the context of gene therapy, as anti-inflammatory agents for reducing host immune responses to ISS-ODN in bacteria and viruses, as autoimmune modulator in combination with autoantigen or autoantibody conjugate to inhibit ISS-ODN stimulated Th1 mediated IL-12 production, for use as an adjuvant for Th2 immune responses to extracellular antigen, and generally to shift a host immune response from a Th1 to a Th2 response. See U.S. Pat. No. 6,255,292.

Yamada et. al, J. Immunol., 169; 5590-5594, 2002, using various in vitro immune activation cell systems evaluated IIS oligodeoxynucleotides in CpG induced immune stimulation. Yamada et. al. found that suppression by IIS oligodeoxynucleotides is dominant over stimulation by oligodeoxynucleotides and it is specific for CpG-induced immune responses. They found that the most suppressive oligonucleotide sequences contained polyG or G-C rich sequences, but a specific hexamer motif was not discovered. Krieg et al., PNAS, 95; 12631-12636, 1998, found that synthetic oligonucleotides containing neutralizing motifs defined by him as CpG dinucleotide in direct repeat clusters or with a C on the 5' side or a G on the 3' side, could block immune activation by immunostimulatory CpG motifs. Again, a hexamer immunoinhibitory squence was not discovered. In Zeuner et al., Arthritis and Rheumatism, 46: 2219-2224, 2002, the IIS described by Kreig at al. above, was demonstrated to reduce CpG induced arthritis in an animal model. In U.S. Pat. No. 6,225,292, Raz et al. describe a specific hexamer motif designated as 5'-purine-purine-[Y]-[Z]-pyrimidine-pyrimidine-3' where Y is any nucleotide except cytosine, and Z is any nucleotide, wherein when Y is not guanosine or inosine, Z is guanosine or inosine, which blocks the stimulatory activity of CpG immunostimulatory sequences. In each of the above examples, the IIS was demonstrated to specifically inhibit immune activation caused by stimulatory CpG sequences.

Nucleic Acid Therapy

Antisense Therapy: Antisense oligonucleotides were originally designed as complementary to specific target genes to decrease their expression (Krieg, Annu. Rev. Immunol., 20:709-760, 2002). In order to prevent the degradation of these oligonucleotides the backbones were generally modified, such as to a phosphorothioate backbone. Although in many cases the antisense oligonucleotides did suppress the expression of target genes in tissues culture cells, in vivo experiments were less successful at altering expression. Instead, many investigators found unexpectedly that some of these oligonucleotides stimulated the immune response in vivo. For example, antisense oligonucleotide against the rev gene of the human immunodeficiency virus (HIV) had an immunostimulatory effect as manifested by increased B cell proliferation and splenomegaly (Branda et al., Biochem. Pharmacol., 45:2037-2043, 1993). Although no immediate immunostimulatory sequence motif was identified from these early studies, these findings led to the eventual search for specific immunostimulatory motifs.

Gene Therapy: Polynucleotide therapeutics, including naked DNA encoding peptides and/or polypeptides, DNA formulated in precipitation- and transfection-facilitating agents, and viral vectors have been used for "gene therapy." Gene therapy is the delivery of a polynucleotide to provide expression of a protein or peptide, to replace a defective or absent protein or peptide in the host and/or to augment a desired physiologic function. Gene therapy includes methods that result in the integration of DNA into the genome of an individual for therapeutic purposes. Examples of gene therapy include the delivery of DNA encoding clotting factors for hemophilia, adenine deaminase for severe combined immunodeficiency, low-density lipoprotein receptor for familial hypercholesterolemia, glucocerebrosidase for Gaucher's disease, α1-antitrypsin for α1-antitrypsin deficiency, alpha- or Beta-globin genes for hemoglobinopathies, and chloride channels for cystic fibrosis (Verma and Somia, Nature, 389, 239-42, 1997).

DNA immunization to treat infection: In DNA immunization a non-replicating transcription unit can provide the template for the synthesis of proteins or protein segments that induce or provide specific immune responses in the host. Injection of naked DNA promotes vaccination against a variety of microbes and tumors (Robinson and Torres, Semin Immunol, 9, 271-83, 1997). DNA vaccines encoding specific proteins, present in viruses (hepatitis B-virus, human Immunodeficiency virus, rotavirus, and influenza virus), bacteria (mycobacterium tuberculosis), and parasites (Malaria), all non-self antigens, are being developed to prevent and treat these infections (Le et al., Vaccine, 18, 1893-901, 2000); (Robinson and Pertmer, Adv Virus Res, 55, 1-74, 2000).

DNA to treat neoplasia: DNA vaccines encoding major histocompatibility antigen class I, cytokines (IL-2, IL-12 and IFN-gamma), and tumor antigens are being developed to treat neoplasia (Wlazlo and Ertl, Arch Immunol Ther Exp, 49:1-11, 2001). For example, viral DNA encoding the B cell immunoglobulin idiotype (antigen binding region) has been administered to eliminate and protect against B cell-lymphomas (Timmerman et al., Blood, 97:1370-1377, 2001).

DNA immunization to treat autoimmune disease: Others have described DNA therapies encoding immune molecules to treat autoimmune diseases. Such DNA therapies include DNA encoding the antigen-binding regions of the T cell receptor to alter levels of autoreactive T cells driving the autoimmune response (Waisman et al., Nat Med, 2:899-905, 1996) (U.S. Pat. No. 5,939,400). DNA encoding autoantigens were attached to particles and delivered by gene gun to the skin to prevent multiple sclerosis and collagen induced arthritis. (Patent WO 97/46253) (Ramshaw et al., Immunol., and Cell Bio., 75:409413, 1997) DNA encoding adhesion molecules, cytokines (TNF alpha), chemokines (C-C chemokines), and other immune molecules (Fas-ligand) have been used to treat animal models of autoimmune disease (Youssef et al., J Clin Invest, 106:361-371, 2000); (Wildbaum et al., J Clin Invest, 106:671-679, 2000); (Wildbaum et al., J Immunol, 165:5860-5866, 2000); (Wildbaum et al., J Immunol, 161:6368-7634, 1998); (Youssef et al., J Autoimmun, 13:21-9, 1999).

It is an object of the present invention to provide a method and composition for treating or preventing a disease, particularly autoimmune disease or inflammatory disease, comprising the administration of immune modulatory nucleic acids. Another object of this invention is to provide the means of identification of the immune modulatory sequences for treating disease. Yet another object of this invention is to provide the method and means of treating a disease associated with self-protein(s), -polypeptide(s), or -peptide(s) that are present and involved in a non-physiological process in an animal comprising the administration of an immune modulatory sequence in combination with a polynucleotide encoding self-protein(s), -polypeptide(s) or -peptide(s). Another object of the present invention is to provide a composition for treating or preventing a disease associated with self-protein(s), -polypeptide(s), or -peptide(s) that is present non-physiologically in an animal. The invention further relates to the treatment or prevention of disease comprising the administration of the immune modulatory nucleic acids in combination with self-molecule(s). These and other objects of this invention will be apparent from the specification as a whole.

BRIEF SUMMARY OF THE INVENTION

The present invention is based on the discovery that immune modulatory sequences alone or in combination could be used to prevent or treat autoimmune or inflammatory diseases associated with self-molecules. It was not appreciated until this invention that immune modulatory sequences containing a GpG dinucleotide or other modulatory dinucleotide as described herein in certain immune modulatory sequence motifs can be used to prevent or treat inflammatory or autoimmune diseases that are independent of proximate or concurrent ISS stimulation (e.g., microbial DNA or recombinant vectors containing CpGs). Examples of the immune modulatory sequence motifs are:

5'-Purine-Pyrimidine-[Y]-[Z]-Pyrimidine-Pyrimidine-3'; and,

5'-Purine-Purine-[Y]-[Z]-Pyrimidine-Pyrimidine-3'

Objects of the present invention are accomplished by a novel method and composition to treat or prevent a disease, particularly an autoimmune or inflammatory disease, comprising the administration of immune modulatory nucleic acids having one or more immune modulatory sequences. The immune modulatory nucleic acids can be administered alone or in combination with a polynucleotide encoding self-protein(s), -polypeptide(s), -peptide(s). The immune modulatory nucleic acids may also be administered in combination with other self molecules to treat an autoimmune or inflammatory disease associated with one or more self-molecules that is present in the individual nonphysiologically. The invention further relates to pharmaceutical compositions for the treatment or prevention of an autoimmune or inflammatory disease wherein the pharmaceutical composition comprises an immune modulatory sequence in the form of a polynucleotide, such as a DNA polynucleotide. The immune modulatory sequence may also be embodied within a vector, by modification of elements of a vector nucleotide sequence to include immune modulatory sequence motifs further comprising an inhibitory dinucleotide motif when used in the context of diseases associated with self-molecules present in the subject non-physiologically, such as in autoimmune or inflammatory disease.

Other objects of the present invention are accomplished by a novel method of treating or preventing a disease in an animal associated with one or more self-protein(s), -polypeptide(s), or -peptide(s) that is present in the animal nonphysiologically comprising administering to the animal an immune modulatory sequence. The invention further relates to a novel method of treating or preventing a disease in an animal associated with one or more self-protein(s), -polypeptide(s), or -peptide(s) that is present in the animal nonphysiologically comprising administering to the animal an immune modulatory sequence in combination with a polynucleotide encoding the self-protein(s), -polypeptide(s) or -peptide(s).

In one aspect of the invention there is provided a method for treating or preventing autoimmune diseases such as multiple sclerosis, rheumatoid arthritis, insulin dependent diabetes mellitus, autoimmune uveitis, primary biliary cirrhosis, myasthenia gravis, Sjogren's syndrome, pemphigus vulgaris, scleroderma, pernicious anemia, systemic lupus erythematosus (SLE), ankylosing spondylitis, autoimmune skin diseases, and Grave's disease comprising administering to the animal an immune modulatory sequence either alone or in combination with a self-vector comprising a polynucleotide encoding a self-protein(s), -polypeptide(s) or -peptide(s) associated with the autoimmune disease. In another aspect of the invention the immune modulatory sequence is administered in combination with a polynucleotide comprising DNA encoding the self-protein(s), -polypeptide(s), or -peptide(s) present in the subject in a non-physiological state and associated with a disease.

In another aspect of the invention there is provided a method for treating or preventing inflammatory diseases such as osteoarthritis, gout, pseudogout, hydroxyapatite deposition disease, asthma, bursitis, tendonitis, conjunctivitis, urethritis, cystitis, balanitis, dermatitis, coronary artery disease, or migraine headache comprising administering to the animal an immune modulatory sequence, either alone or in combination.

In yet another aspect of the invention there is provided a method for treating or preventing diseases related to organ or cell transplantation including but not limited to GVHD or transplant rejection comprising administering to the animal an immune modulatory sequence, either alone or in combination with a self-vector comprising a polynucleotide encoding a self-protein(s), -polypeptide(s) or -peptide(s) associated with GVHD or transplant rejection. Administration of the immune modulatory sequence and the self-vector comprising a polynucleotide encoding the self-protein(s), -polypeptide(s), or -peptide(s) modulates an immune response to the self-protein(s), -polypeptide(s) or -peptide(s) expressed by the self-vector.

and IL12p40 (B) production were measured by ELISA. As indicated there is a dose-dependent inhibition of the production of both IL6 and IL12p40 with increasing concentrations of the IMS. Each data point represents the mean of triplicate wells.

Figure 4:
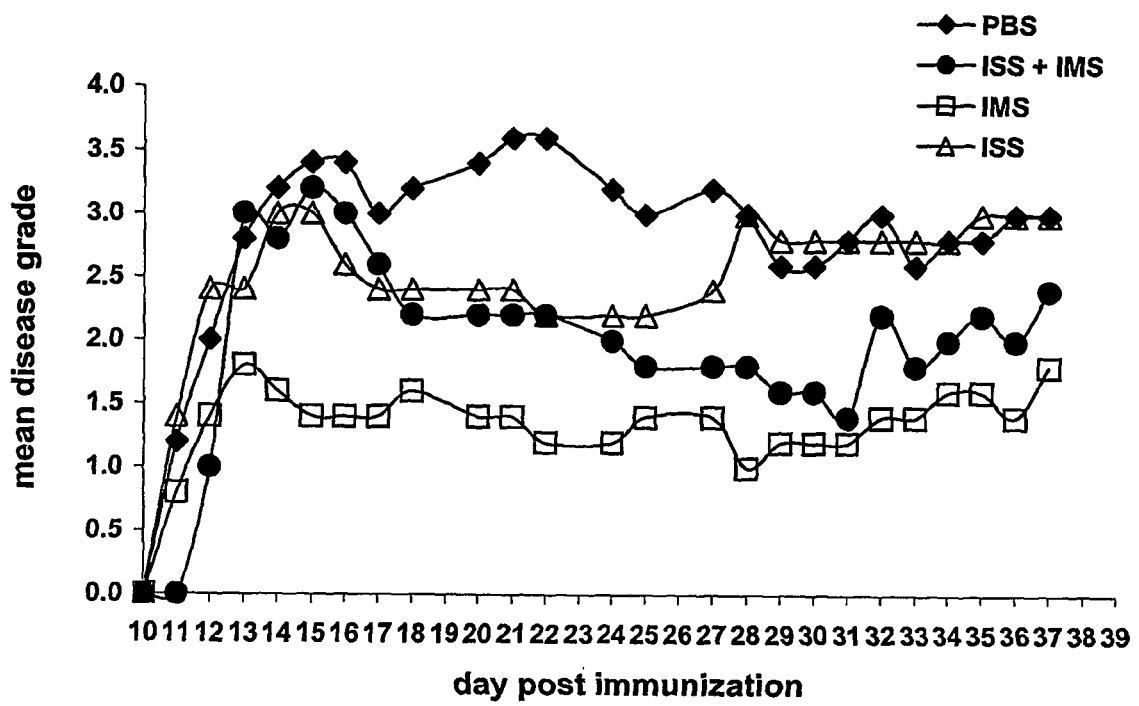

FIG. 4: Prevention therapy with Inhibitory IMS suppresses $PLP_{139-151}$ mediated EAE. SJL/J mice were immunized subcutaneously with 100 µg of $PLP_{139-151}$ peptide in PBS emulsified in CFA. 50 µg of the IMS resuspended in PBS was administered intraperitoneally fourteen and seven days prior to the peptide immunization. Animals were clinically scored daily. Grade 1, tail paralysis, grade 2, hind limb paraparesis, grade 3, hind limb paralysis, grade 4, complete paralysis (tetraplegy), grade 5, death.

Figure 5:
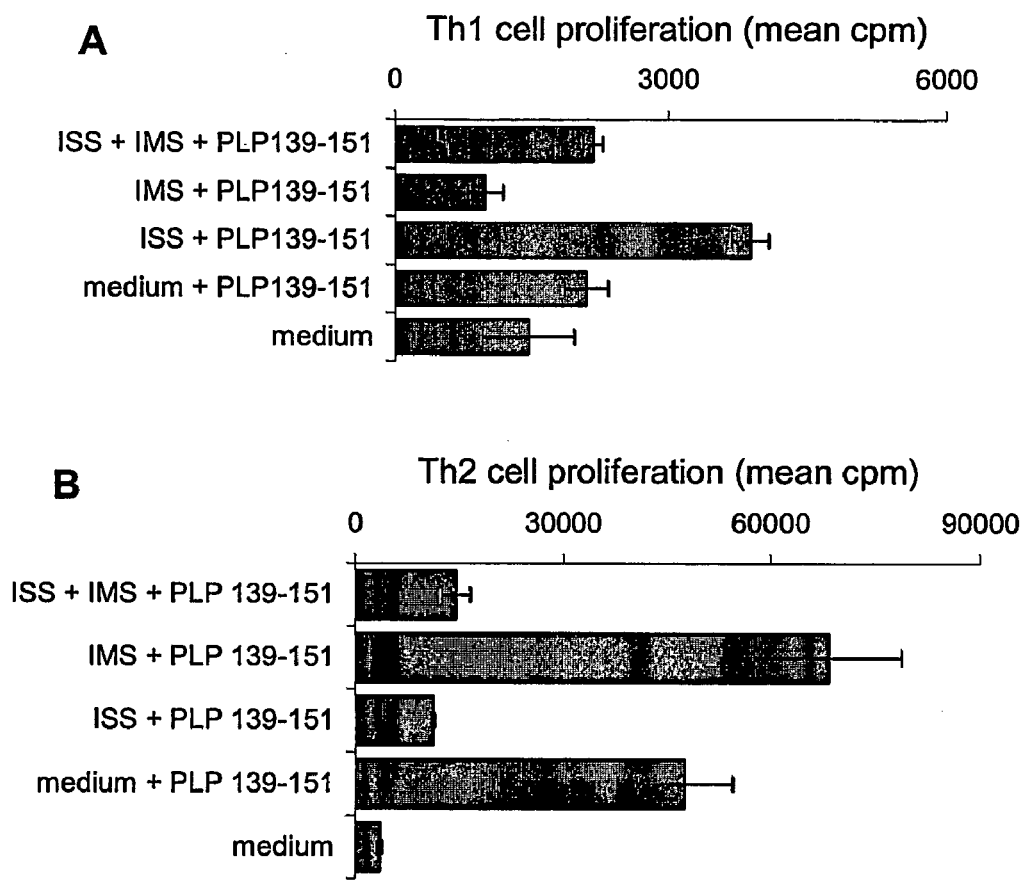

FIG. 5: Prevention therapy with Inhibitory IMS suppresses $PLP_{139-151}$ mediated EAE. SJL/J mice were immunized subcutaneously with 100 µg of $PLP_{139-151}$ peptide in CFA consisting of incomplete Freund's adjuvant and 0.5 mg of heat-inactivated *Mycobacterium tuberculosis*. 50 µg of the indicated ODN resuspended in PBS was administered intraperitoneally on the same day (day 0) as the peptide immunization. Animals were clinically scored daily. Grade 1, tail paralysis, grade 2, hind limb paraparesis, grade 3, hind limb paralysis, grade 4, complete paralysis (tetraplegy), grade 5, death.

Figure 6:
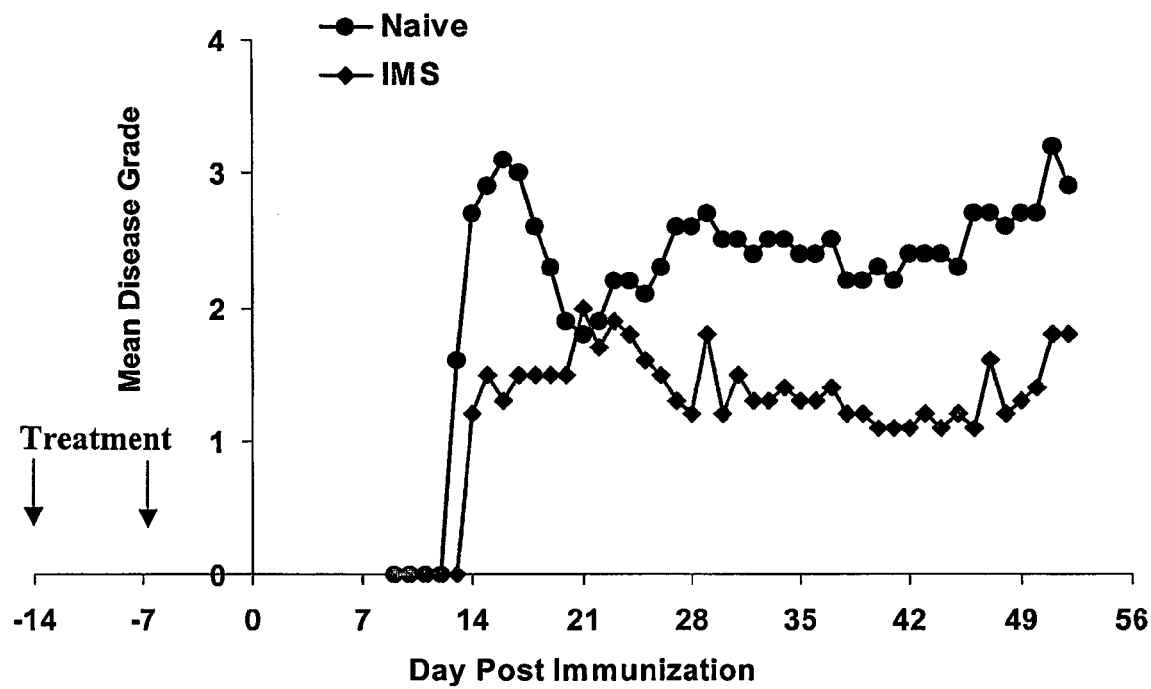

FIG. 6: Differential proliferation effects of IMS on purified antigen specific T cells. (A) Inhibitory IMS suppresses Th1 cells. Naïve whole splenocytes were co-cultured with $PLP_{139-151}$ peptide and the indicated ODN for 24 h. Following irradiation of the peptide loaded splenocytes, a $PLP_{139-151}$ specific Th1 cell line was added for another 72 h. IMS does not stimulate Th1 cell proliferation and in fact decreases the proliferation induced by CpG-ODN slightly. (B) In contrast, inhibitory IMS does not inhibit the proliferation of a $PLP_{139-151}$ specific Th2 cell line. Note that the CpG-ODN reduces the proliferation of this Th2 cell line. In each of these three experiments, wells were pulsed with 1 µCi[$^3$H]TdR for the final 16 h of culture before incorporated radioactivity was measured. Each data point represents the mean of triplicate wells+/−SD.

Figure 7A:
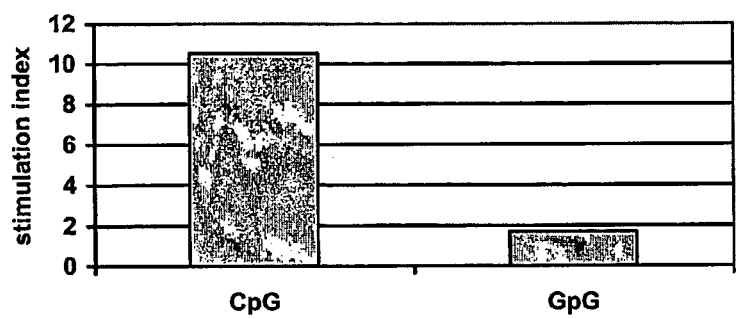
Figure 7B:
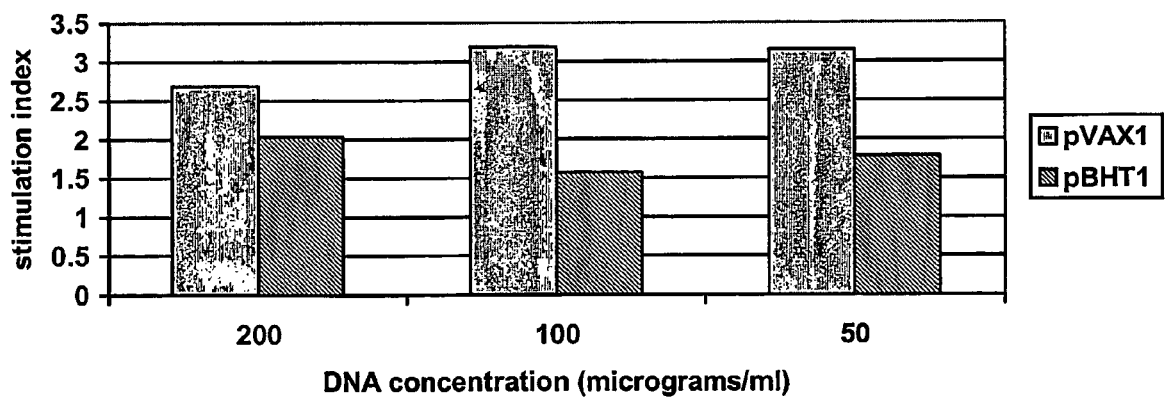

FIG. 7: Modifications in the pBHT1 vector reduce the proliferative activity of splenocytes. (A) Whole splenocytes were cultured with stimulatory CpG oligonucleotide and immunomodulatory GpG oligonucleotide for 24 h. Wells were pulsed with 1 µCi[$^3$H]-thymidine for the final 4 h of culture before incorporated radioactivity was measured. The stimulation index was calculated based on the degree of proliferation above the proliferation of splenocytes incubated with medium only. (B) Whole splenocytes were cultured with the pVAX1 empty vector or pBHT1 empty vector at the indicated concentrations for 24 h. Wells were pulsed with 1 µCi[$^3$H]-thymidine for the final 4 h of culture before incorporated radioactivity was measured. The stimulation index was calculated based on the degree of proliferation above the proliferation of splenocytes incubated with medium only.

FIG. 8: Reduced activation of APC's with pBHT1 vector. Naïve splenocytes were cultured with 10 µg/ml CpG or GpG oligonucleotide (A) or 100 µg/ml of pVAX1 or pBHT1 for 48 hours. Cells were harvested, stained or CD16/32 expression and analyzed by FACScan. The unmarked graph represents cells incubated with medium only.

Figure 9:
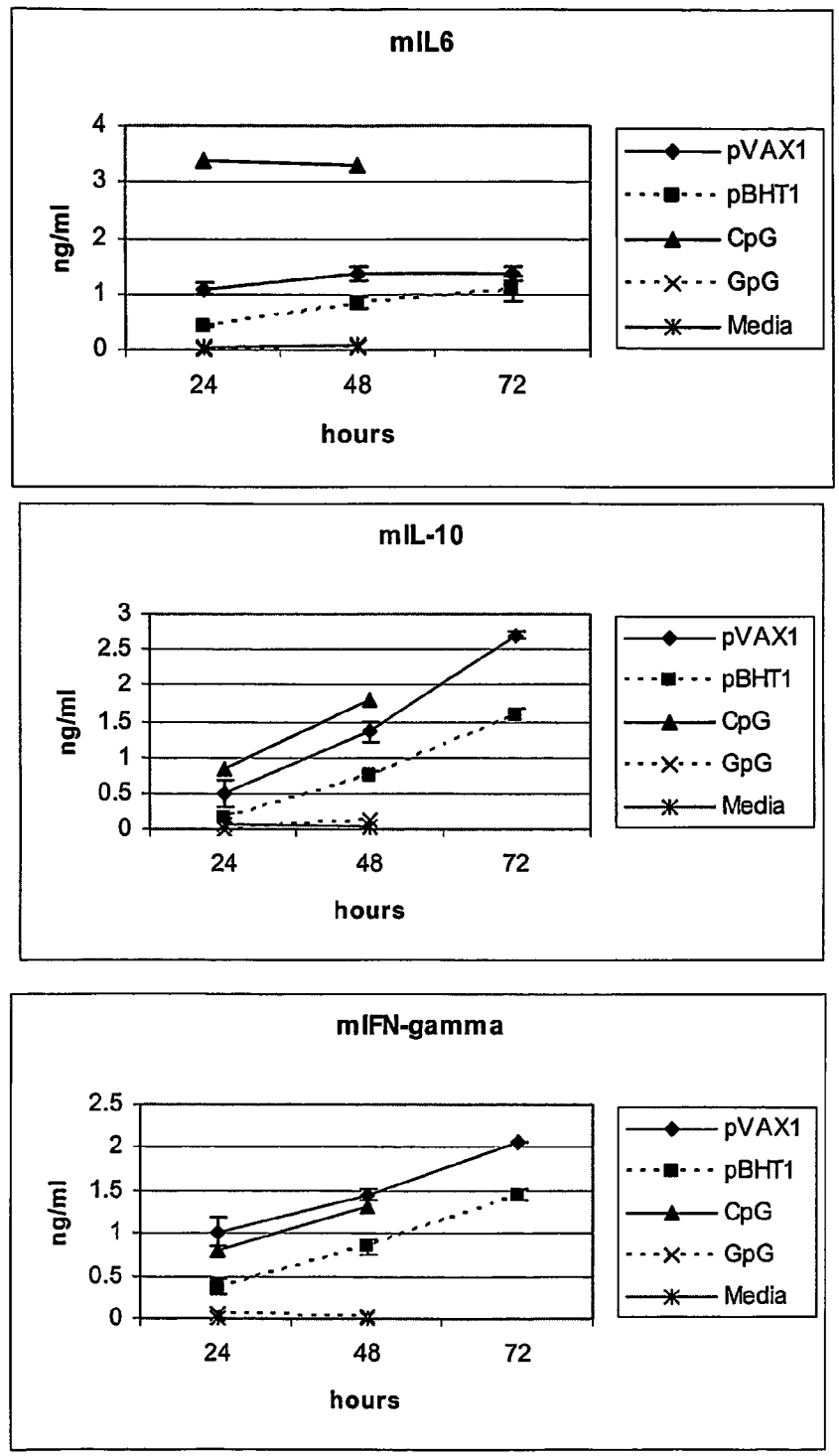

FIG. 9: Reduced cytokine production with the pBHT1 vector. Naïve splenocytes were cultured with 10 µg/ml of stimulatory CpG oligo, immunomodulatory GpG oligo, 100 µg/ml of pVAX1 DNA or 100 µg/ml of pBHT1 DNA. Supernantants were harvested after the times indicated and IL6, IL10, and IFNγ production was measured by sandwich ELISA. Each data point represents the mean of triplicate wells.

Figure 10A:
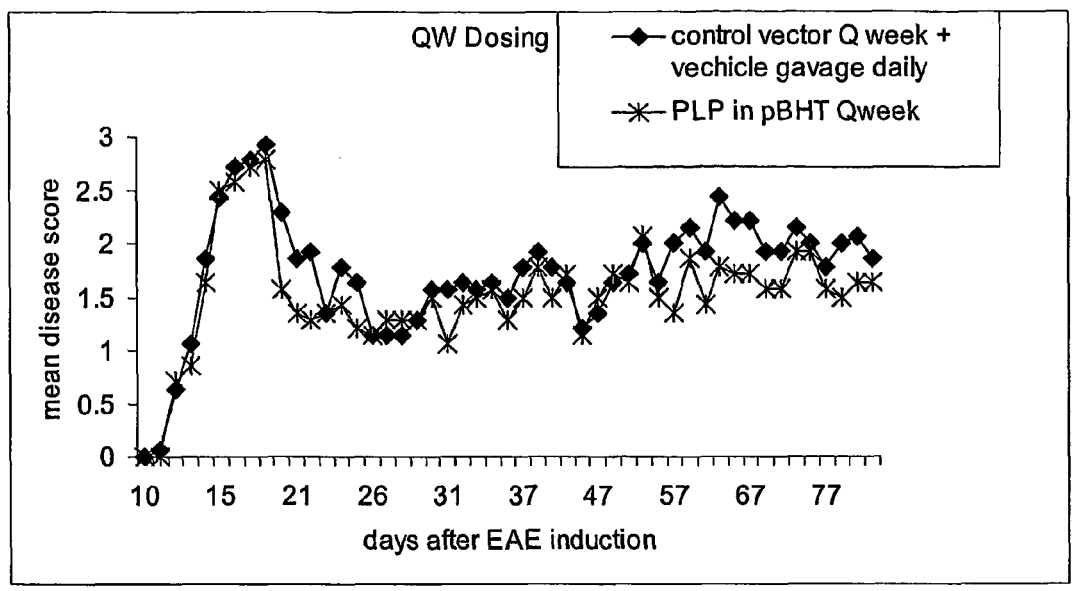
Figure 10B:
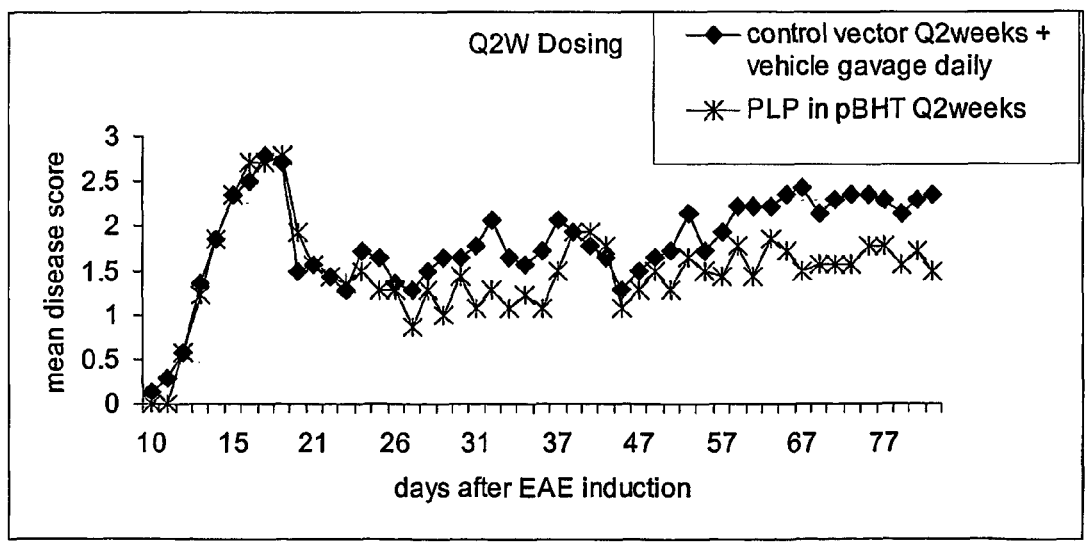
Figure 10C:
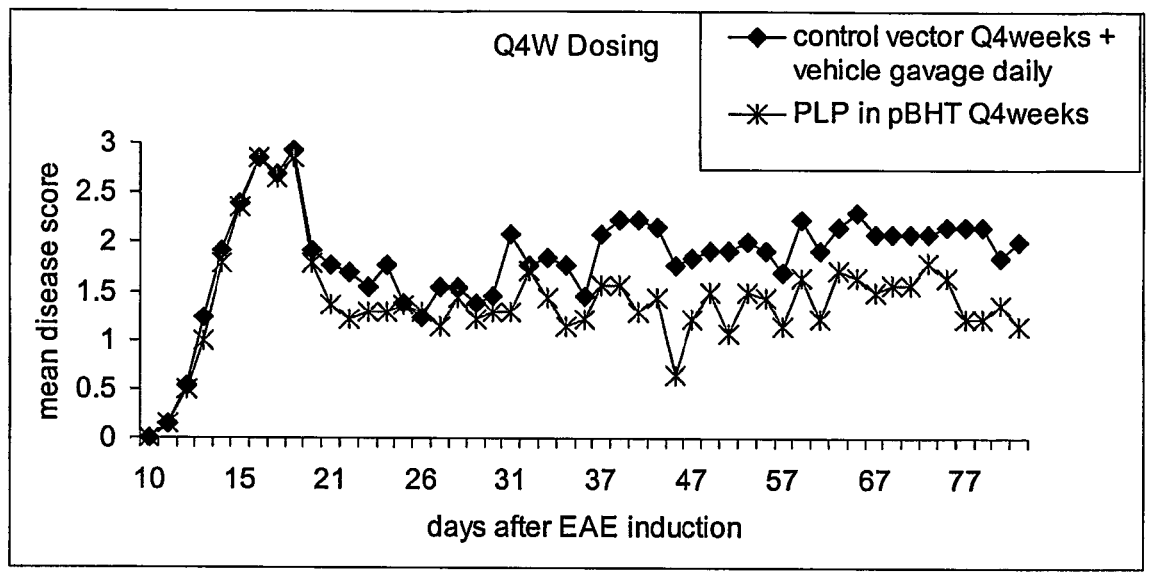

FIG. 10. The pBHT1 vector encoding a self antigen reduced EAE severity. The DNA encoding the self-antigen, mouse PLP (proteolipid protein), was incorporated within the pBHT1 vector and administered intramuscularly to SJL mice. Mice were first induced for EAE with the peptide $PLP_{139-151}$ in CFA (complete Freund's adjuvant) at day 0, and then several days after the onset of disease (on day 20) were randomized into various treatment groups. Fifty µg of mouse PLP encoded within the pBHT1 vector or fifty µg of an empty pBHT1 vector control were then administered intramuscularly at three different dose frequencies: (A) once per week, (B) once every other week, and (C) once every four weeks. Mice were scored daily for EAE disease severity on a 1 to 5 scale and the mean disease score of a treatment group is graphed. There is a reduction in the mean disease score in all of the treatment groups, most notably at a frequency of every two or every four weeks.

Figure 11:
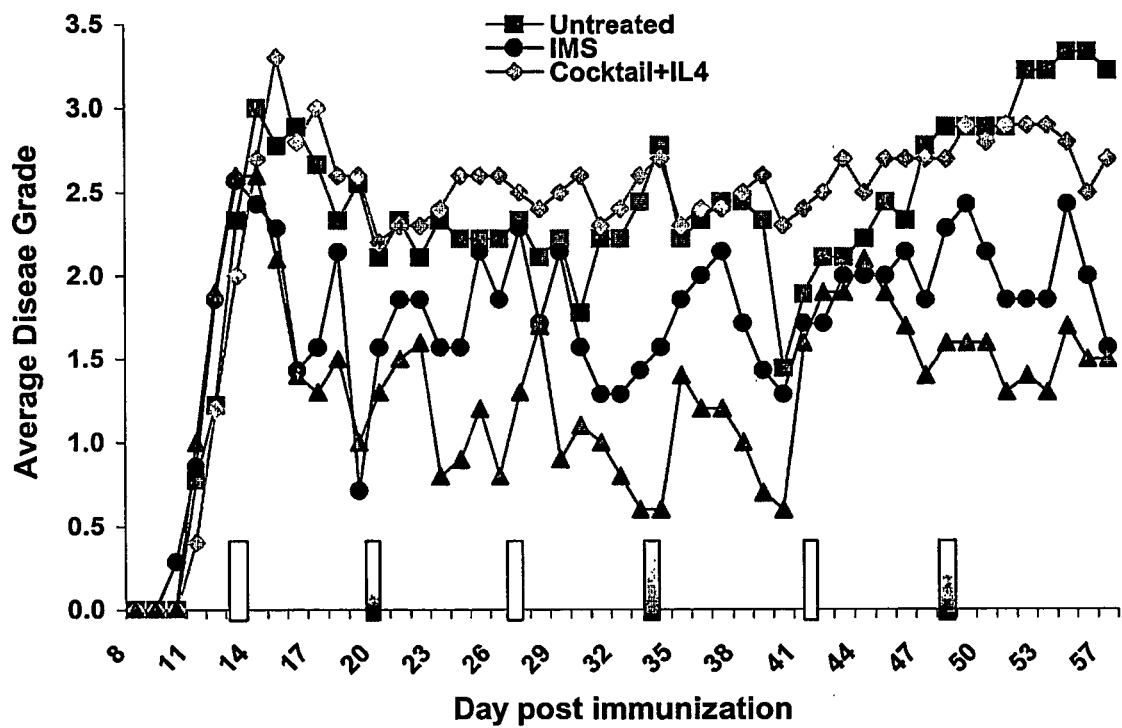

FIG. 11: Polynucleotide therapy with Inhibitory IMS suppresses $PLP_{139-151}$ mediated EAE. On day 0, seven-week old female SJL/J mice were immunized subcutaneously with 100 µg $PLP_{139-151}$ in PBS emulsified in CFA, consisting of IFA and 0.5 mg heat-inactivated *Mycobacterium tuberculosis*. Animals were clinically scored daily beginning on day 7. On day 12, mice were injected in both quadriceps with a total of 0.1 ml 0.25% Bupivacaine-HCL in PBS. Two days later, selected mice were injected intramuscularly in both quadriceps with DNA polynucleotide encoding full-length murine PLP, MAG, MOG, and MBP each on a separate pTARGET plasmid (25 µg of each) plus 50 µg pTARGET plasmid encoding full-length murine IL-4 in a total volume of 0.2 ml TE. DNA injections were given at weekly intervals for six weeks. At the same time as initial DNA treatment, 50 µg IMS in a volume of 200 µl PBS was administered intraperitoneally alone or with DNA polynucleotide treatment. IMS was given every other week for six weeks.

Figure 12:
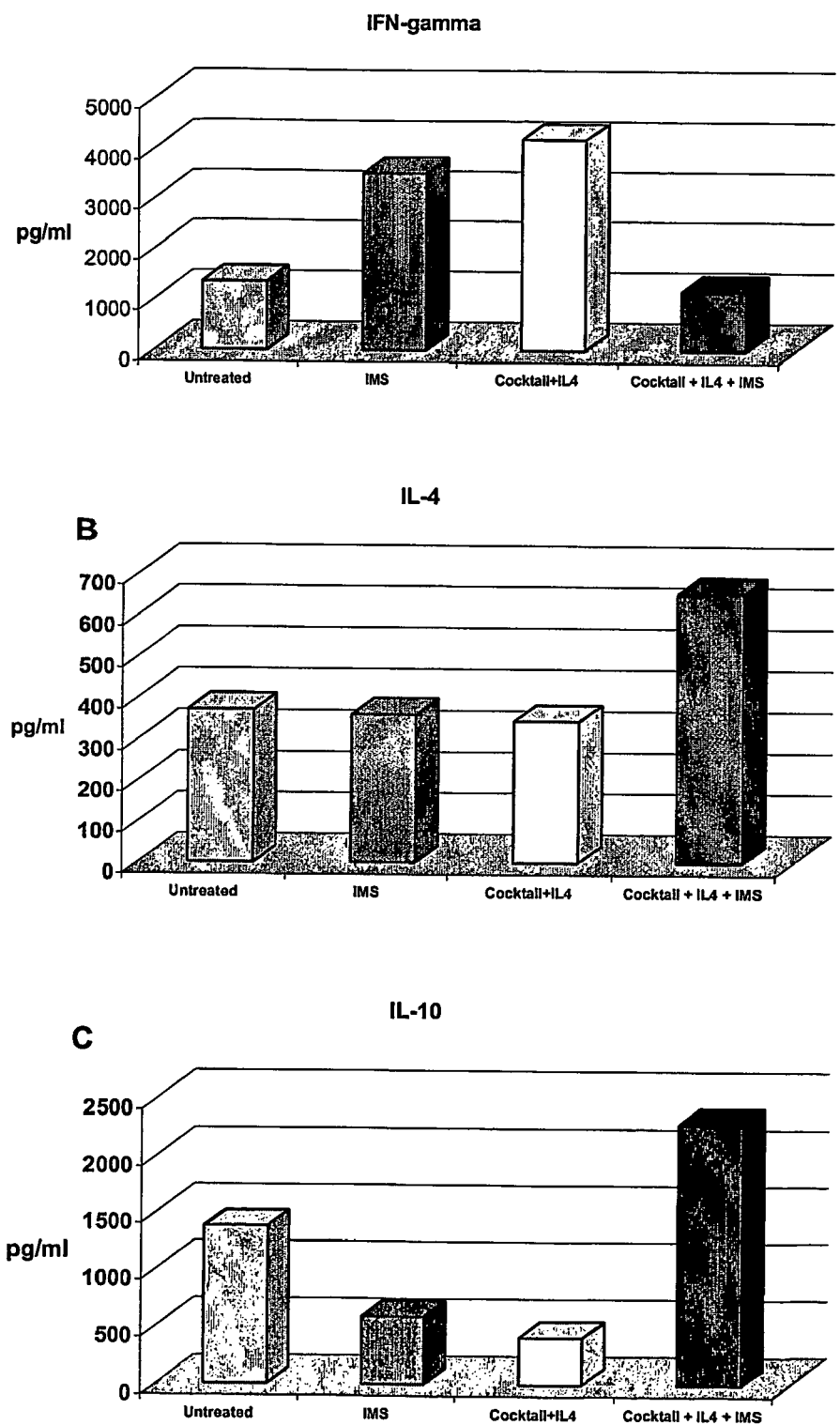

FIG. 12: Cytokine profile of EAE treated groups. Fifty-seven days after EAE disease induction, mice were sacrificed and inguinal and axillary lymph nodes from each mouse were extracted and pooled according to the respective groups. Cells were isolated and stimulated with 10 µg/ml in $PLP_{139-151}$ in enriched RPMI media and 10% FCS. Three days later, cells supernatants were collected and tested for cytokine profile by sandwich ELISA using standard murine (A) IFN-gamma, (B) IL-4 and (C) IL-10 ELISA kits from BD Pharmingen.

Figure 13:
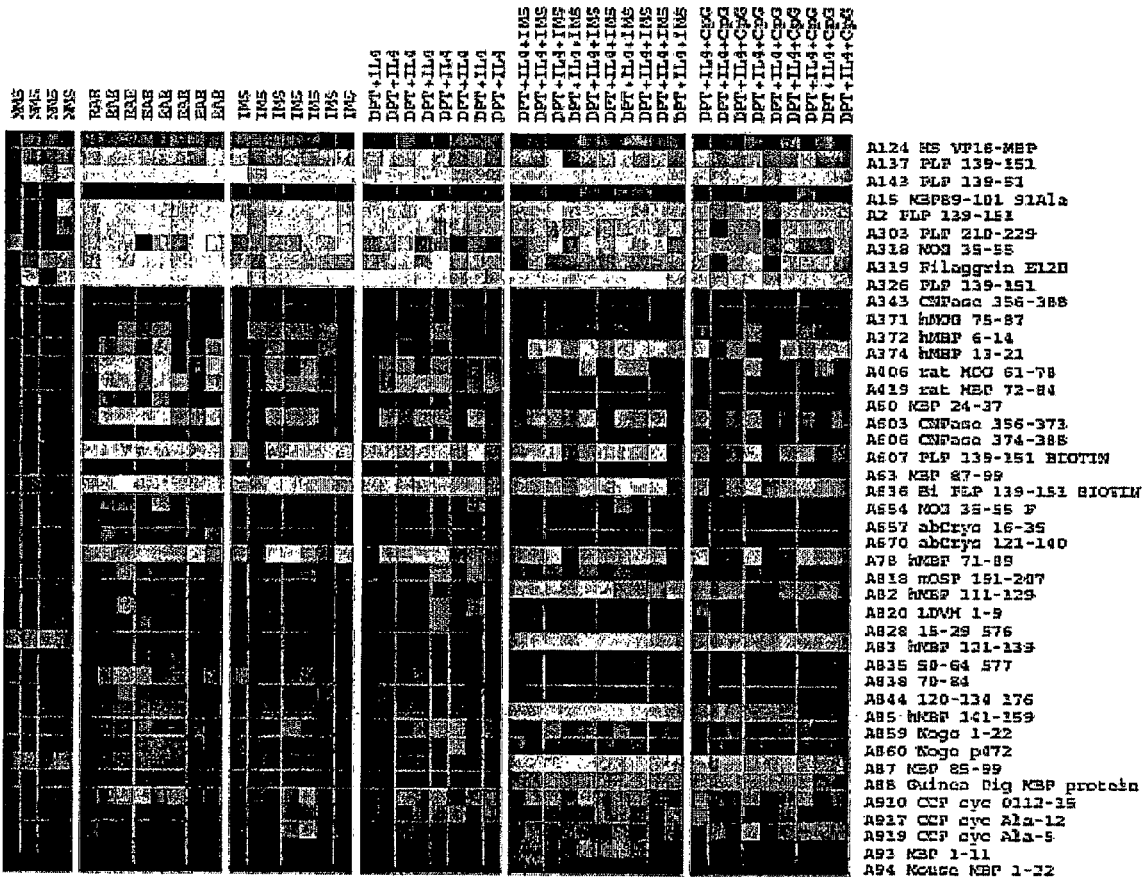

FIG. 13: Myelin autoantibody epitope spreading analysis using protein microarray technology. Fourteen days after onset of and following partial recovery from acute paralytic EAE induced with $PLP_{139-151}$, SJL/J mice were treated weekly with PBS vehicle, IMS, pTARGET expressing MBP, PLP, MOG and MAG (DPT) and IL-4; DPT and IL-4 plus IMS; DPT and IL-4 plus CpG. Following the six-week treatment, serum was obtained from each treatment group including normal mouse serum (NMS), myelin protein microarray analysis performed, and SAM used to identify and create a hierarchical cluster analysis to order the antigen features.

FIG. 14: Inhibitory IMS alone and in combination with polynucleotide therapy suppresses $PLP_{139-151}$ mediated EAE. On day 0, seven-week old female SJL/J mice were immunized subcutaneously with 100 µg $PLP_{139-151}$ in PBS emulsified in CFA, consisting of IFA and 0.5 mg heat-inactivated *Mycobacterium tuberculosis*. Animals were clinically scored daily beginning on day 7. On day 14, mice were injected in both quadriceps with a total of 0.1 ml 0.25% Bupivacaine-HCL in PBS. Two days later, selected mice were injected intramuscularly in both quadriceps with DNA polynucleotide encoding full-length murine PLP, MAG, MOG, and MBP each on a separate pTARGET plasmid (25 µg of each) plus 50 µg pTARGET plasmid encoding full-length murine IL-4 in a total volume of 0.2 ml TE. DNA injections were given at weekly intervals for six weeks. At the same time as initial DNA treatment, 50 µg IMS in a volume of 200 µl PBS was administered intraperitoneally alone (A), or with DNA polynucleotide treatment (B). IMS was given every other week for six weeks.

FIG. 15: DNA Polynucleotide Therapy and IMS treats diabetes in NOD mice. NOD/Lt female mice were obtained at 7 weeks of age and housed in a restricted access room. Mice were tested weekly for elevated blood glucose levels (BGL) beginning at 10 weeks of age using the One Touch Ultra Blood Glucose Monitoring System. Treatment was initiated when the BGL was between 200 to 250 mg/dl. Mice were added sequentially to each group as they became available, beginning at the age of 15 weeks. Mice were injected in both quadriceps with a total of 0.2 ml 0.25% Bupivacaine-HCL in PBS. Two days later, mice were injected intramuscularly in both quadriceps either with: 1) DNA polynucleotide encoding full-length murine preproinsulin-1 and preproinsulin-2 each on a separate pVAX1 vector at 50 µg/dose; or, 2) DNA polynucleotide encoding full-length murine preproinsulin-1 and preproinsulin-2 each on a separate pVAX1 vector at 50 µg/dose plus a pVAX1 plasmid encoding IL4 in a total volume of 0.2 ml PBS. Injections were given at weekly intervals for four weeks. At the same time as initial DNA treatment, 50 µg IMS in a volume of 200 µl PBS was administered intraperitoneally alone or with DNA polynucleotide treatment. IMS was given at weekly intervals for four weeks. The percent survival over the progression of observed diabetes was examined for nine weeks following the initial treatment (A). Percent diabetic at week 29 of age is defined as mice with a sustained BGL of over 250 mg/dl (B).

Figure 16:
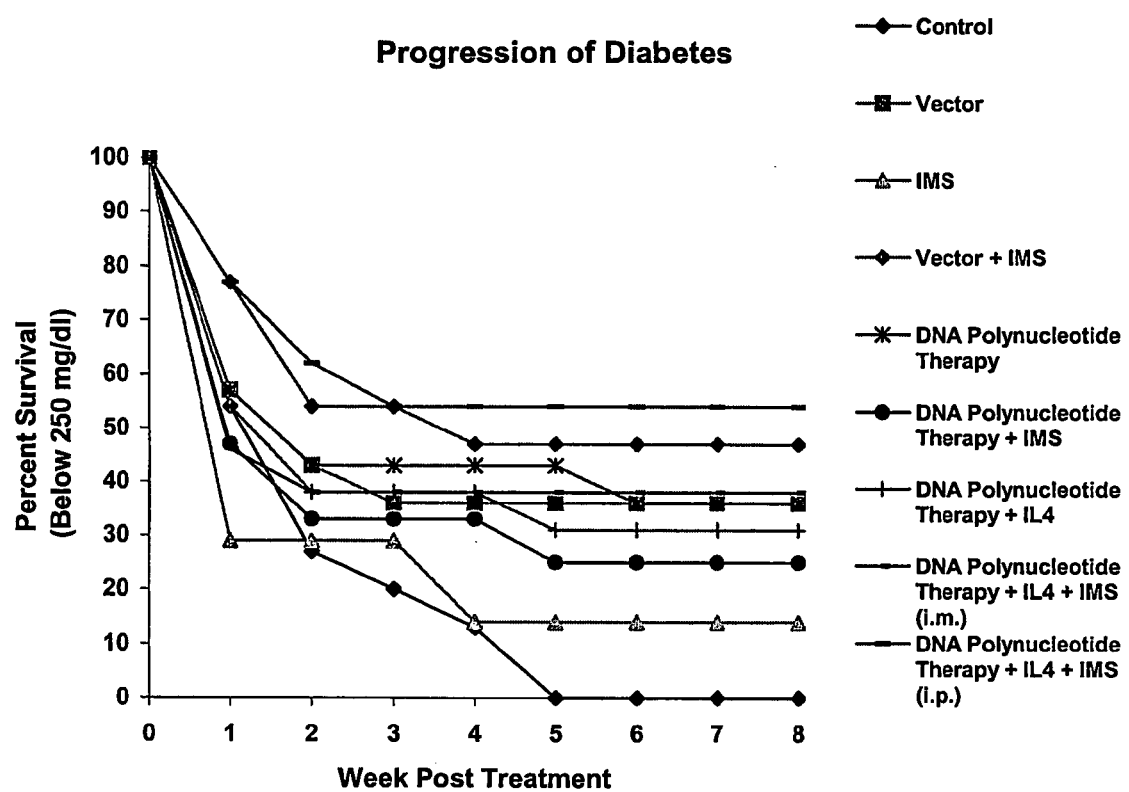

FIG. 16: DNA Polynucleotide Therapy and IMS treats diabetes in NOD mice. NOD/Lt female mice were obtained at 7 weeks of age and housed in a restricted access room. Mice were tested weekly for elevated blood glucose levels (BGL) beginning at 10 weeks of age using the One Touch Ultra Blood Glucose Monitoring System. Treatment was initiated when the BGL was between 200 to 250 mg/dL. Mice were added sequentially to each group as they became available, beginning at the age of 15 weeks. Mice were injected in both quadriceps with a total of 0.2 ml 0.25% Bupivacaine-HCL in PBS. Two days later, mice were injected intramuscularly in both quadriceps either with: 1) PBS treated, 2) empty pVAX1 plasmid at 200 ug/dose, 3) IMS at 50 ug/dose given intramuscularly, 4) the combination of empty pVAX1 plasmid plus IMS (intramuscularly), 5) the combination of DNA polynucleotide encoding full-length murine preproinsulin-1 and preproinsulin-2 each on a separate pVAX1 vector at 50 µg/dose, 6) the combination of DNA polynucleotide plus IMS (intramuscularly), 7) the combination of DNA polynucleotide plus 50 µg/dose of a pVAX1 plasmid encoding IL-4, 8) the combination of DNA polynucleotide plus IL-4 plus IMS (intramuscularly), 9) the combination of DNA polynucleotide plus IL-4 and a separate 50 µg/dose intraperitoneal injection of IMS a total volume of 0.2 ml PBS. All injections were given at weekly intervals for eight weeks. Percent diabetic is defined as mice with a sustained BGL of over 250 mg/dl. The percent survival over the progression of observed diabetes was examined for eight weeks following the initial treatment.

Figure 17A:
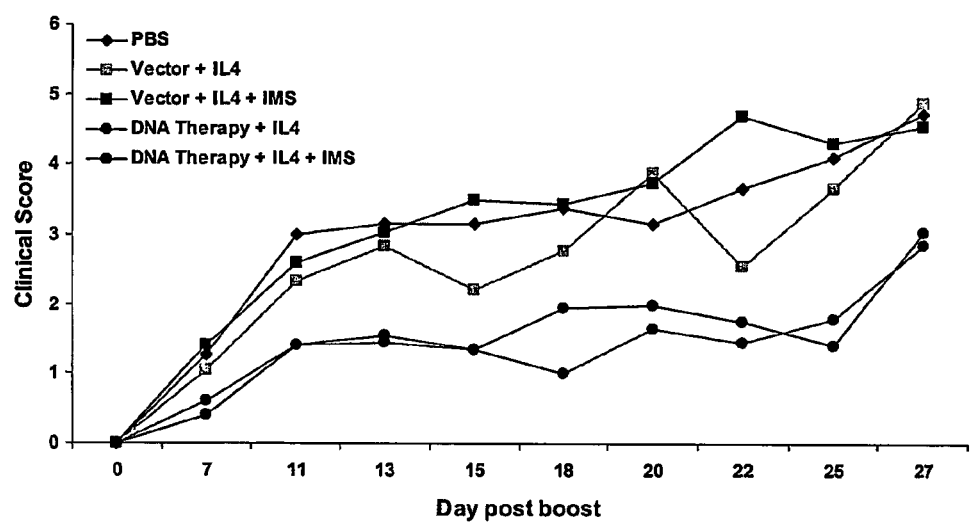

FIG. 17: DNA Therapy with Inhibitory IMS suppresses collagen Type II induced CIA. Groups of 20 six-week-old male DBA/1 mice were pre-treated IM with 50 µg of the indicated DNA vaccines 14 and 7 days prior to induction of CIA with CII emulsified in Complete Freund's Adjuvant. Mice received a third DNA tolerizing vaccine dose 1 week following induction of CIA. Mice were boosted 2 weeks later with CII emulsified in Incomplete Freund's Adjuvant. Arthritis was scored using the visual scoring system as described in Current Protocols in Immunology. (A) DNA encoding whole type II collagen (CII) in combination with DNA encoding IL-4 with and without IMS, resulted in significant reductions in the average severity of arthritis as compared to control groups treated with DNA vaccine vector (pTarget)+IL-4 with or without IMS. (B) The overall percent disease incidence was comparable in all groups.

Figure 18:
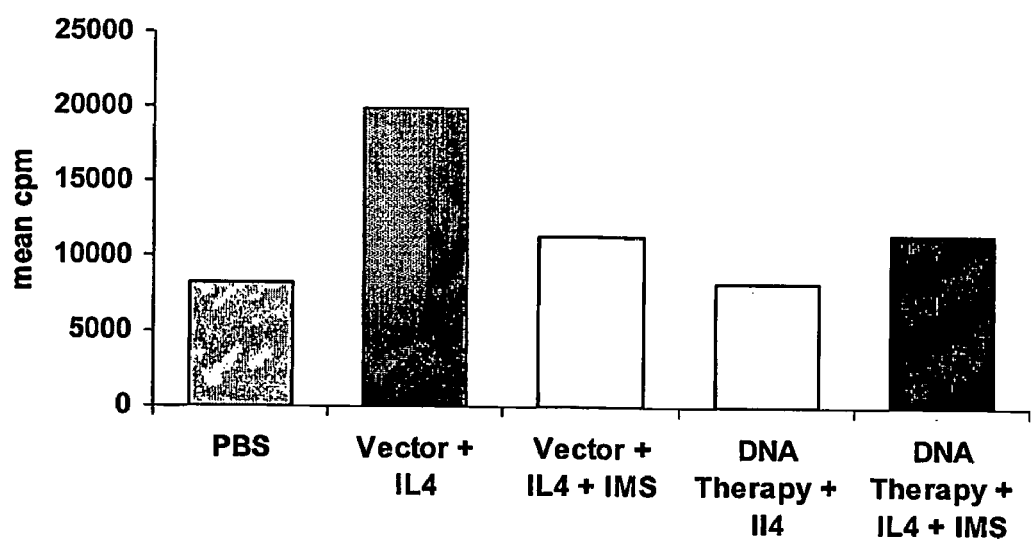

FIG. 18: Proliferation assay of CIA treated groups. Twenty-seven days after CIA immunization boost, mice were sacrificed and inguinal and axillary lymph nodes from each mouse were extracted and pooled according to the respective groups. Cells were isolated and stimulated with 100 µg/ml denatured type II collagen in enriched RPMI media and 10% FCS for 72 hours. Cells were pulsed with 1 µCi[$^3$H]TdR for the final 16 h of culture before incorporated radioactivity was measured. Each data point represents the mean of triplicate wells+/−SD.

Figure 19:
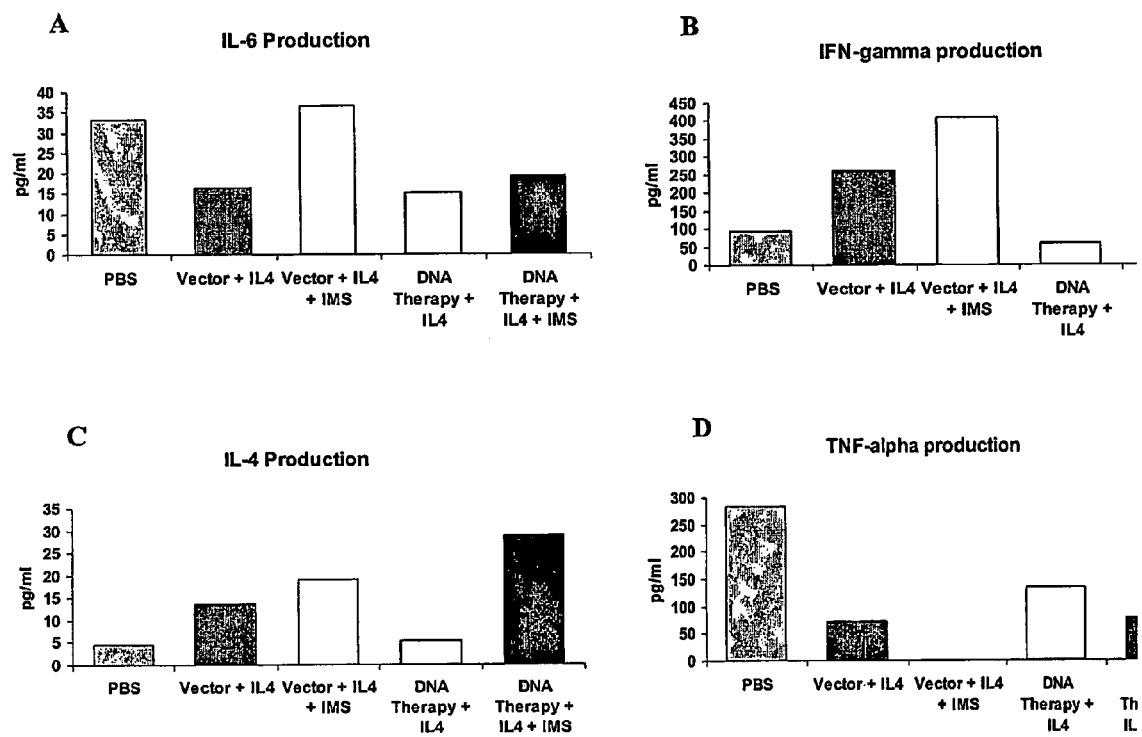

FIG. 19: Cytokine profile of CIA treated groups. Twenty-seven days after CIA immunization boost, mice were sacrificed and inguinal and axillary lymph nodes from each mouse were extracted and pooled according to the respective groups. Cells were isolated and stimulated with 100 µg/ml denatured type II collagen in enriched RPMI media and 10% FCS for 72 hours. Supernatants were collected and tested for cytokine profile by sandwich ELISA using standard murine (A) IL-6, (B) IL-4 (C) IFN-gamma, and (D) TNF-alpha ELISA kits from BD Pharmingen.

Figure 20A:
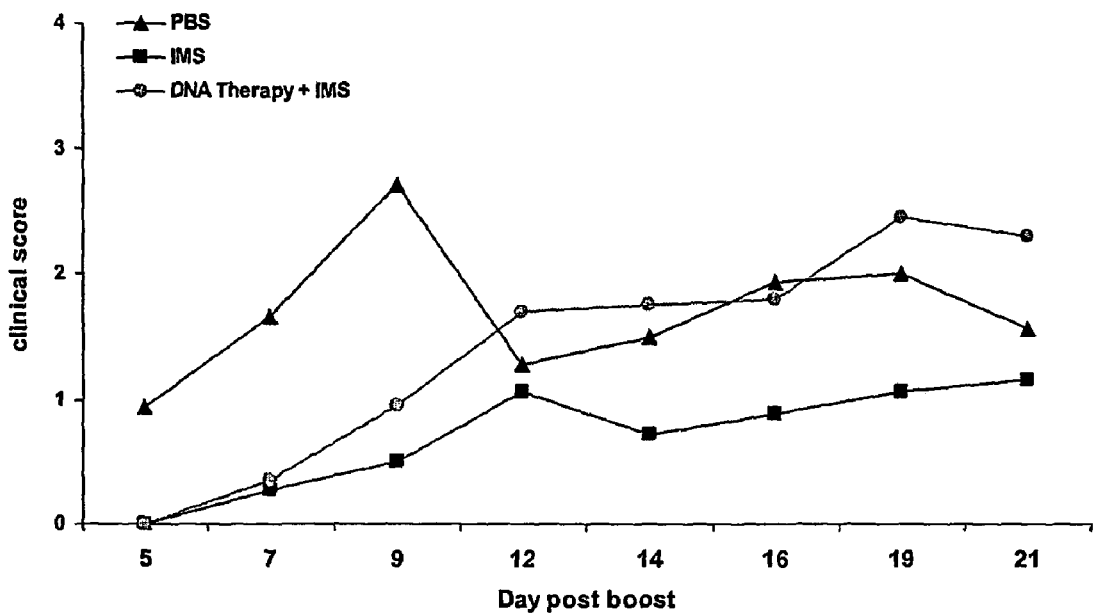

FIG. 20: DNA Therapy with Inhibitory IMS suppresses collagen Type II induced CIA. Groups of 20 six-week-old male DBA/1 mice were pre-treated IM with 50 µg of the indicated DNA vaccines and IP with IMS 14 and 7 days prior to induction of CIA with CII emulsified in Complete Freund's Adjuvant. Mice received a third DNA tolerizing vaccine dose and IMS 1 week following induction of CIA. Mice were boosted 2 weeks later with CII emulsified in Incomplete Freund's Adjuvant. Arthritis was scored using the visual scoring system as described in Current Protocols in Immunology. (A) IMS treated mice, resulted in significant reductions in the average severity of arthritis as compared to the untreated control group and the group treated with DNA encoding whole type II collagen (CI) in combination with IMS. (B) The overall percent disease incidence was decreased in the IMS treated group compared to the other two comparable in all groups.

Figure 21:
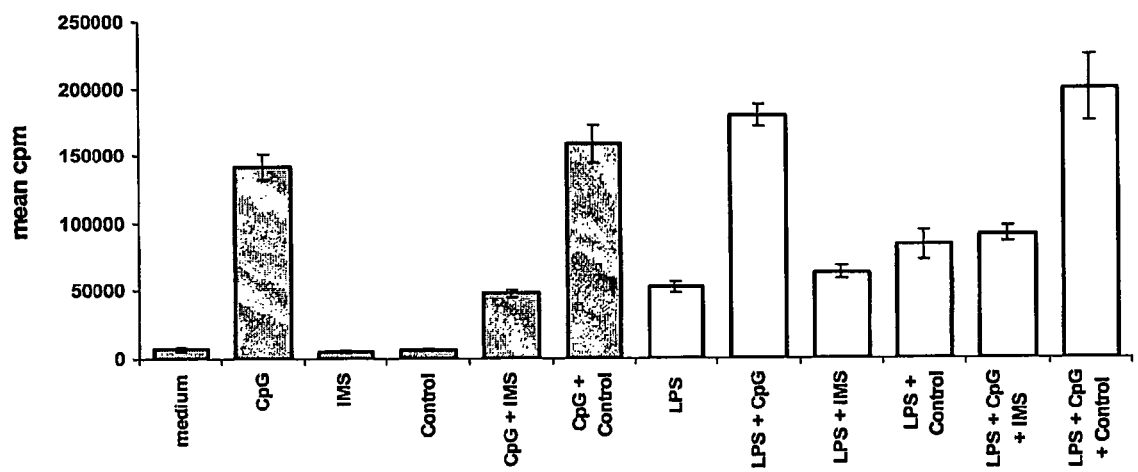

FIG. 21: Inhibitory IMS suppresses B cell proliferation mediated by ISS (CpG-ODN). Primary B cells were isolated from the spleen by a standard B cell panning technique using a goat anti-mouse IgG and IgM, heavy and light chain specific antibody with goat gamma globulin as a carrier protein, and purity>97% B220$^+$ cells was determined by FACScan analysis. B cells were cultured with 5 ug/ml of indicated oligo for 72 h. LPS was co-cultured at 100 ng/ml. Wells were pulsed with 1 µCi[$^3$H]TDR for the final 16 h of culture before incorporated radioactivity was measured. Each data point represents the mean of triplicate wells+/−SD.

Figure 22:
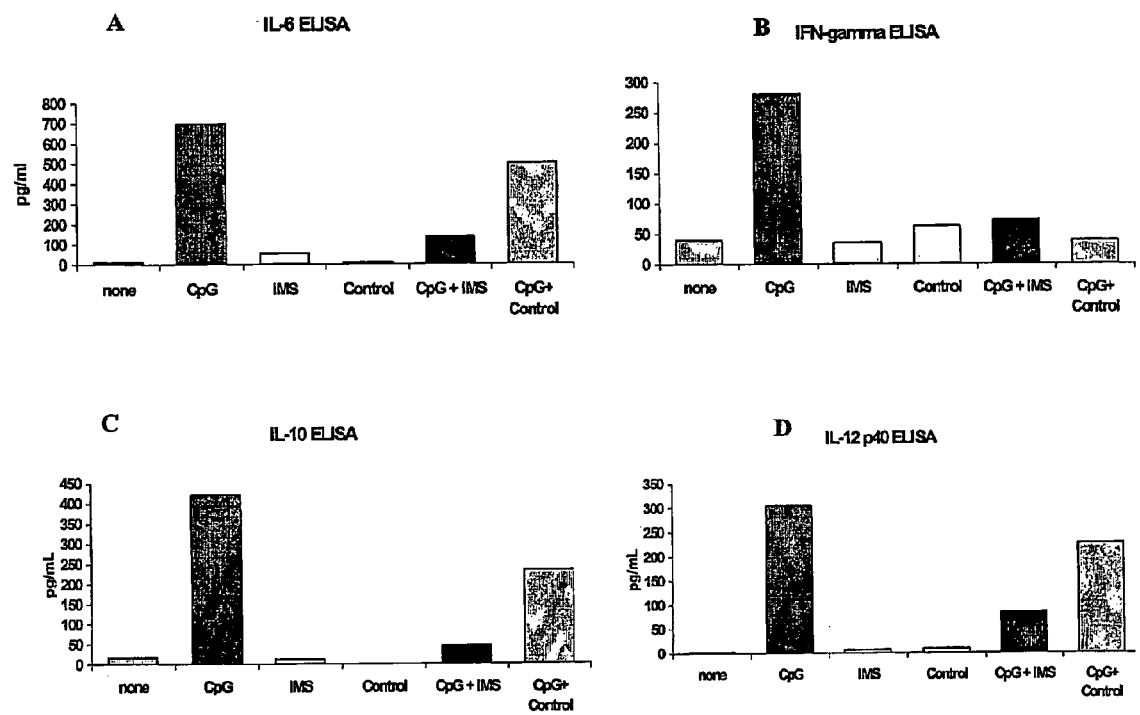

FIG. 22: Inhibitory IMS suppresses Th1 cytokine production of B cells. Naïve primary B cells were cultured with the indicated concentrations of stimulatory CpG-ODN, inhibitory IMS, or control ODN. Supernatants were harvested after 72 h. IL6 (A); IFN-gamma (B), IL-10 (C), and IL12p40

(D) production were measured by ELISA. Each data point represents the mean of triplicate wells.

DETAILED DESCRIPTION OF THE INVENTION

Before describing the present invention in detail, it is to be understood that this invention is not limited to particular formulations or process parameters as they may, of course, vary. It is also to be understood that the terminology used herein is for the purpose of describing particular embodiments of the invention only, and is not intended to be limiting.

DEFINITIONS

"Nucleic acid" and "polynucleotide" as used herein are synonymous and refer to a polymer of nucleotides (e.g., deoxynucleotide, ribonucleotides, or analog thereof).

"Oligonucleotide" as used herein refers to a subset of nucleic acid of from about 6 to about 175 nucleotides or more in length. Typical oligonucleotides are up to about 100 nucleotides in length. Oligonucleotide refers to both oligoribonucleotides and to oligodeoxyribonucleotides, herein after referred to ODNs. ODNs include oligonucleosides and other organic base containing polymers.

Nucleotides are molecules comprising a sugar (preferably ribose or deoxyribose) linked to a phosphate group and an exchangeable organic base, which can be either a substituted purine (guanine (G), adenine (A), or inosine (I)) or a substituted pyrimidine (thymine (T), cytosine (C), or uracil (U)).

Immune Modulatory Sequences (IMSs). "Immune modulatory sequence" or "IMS" as used herein refers to a sequence of nucleotides of a nucleic acid or region of a nucleic acid that is capable of modulating an autoimmune or inflammatory disease. An IMS may be, for example, an oligonucleotide or a sequence of nucleotides incorporated in a vector. An "immune modulatory nucleic acid" as used herein means a nucleic acid molecule that comprises one or more IMSs.

The terms "identity" or "percent identity" in the context of two or more nucleic acid or polypeptide sequences, refer to two or more sequences or subsequences that are the same or have a specified percentage of amino acid residues or nucleotides that are the same, when compared and aligned for maximum correspondence, as measured using either a sequence comparison algorithm such as, e.g., PILEUP or BLAST or a similar algorithm (See, e.g., Higgins and Sharp, *CABIOS*, 5:151-153, 1989; Altschul et al., *J. Mol. Biol.*, 215: 403-410, 1990). Optimal alignment of sequences for comparison can be conducted, e.g., by the local homology algorithm of Smith & Waterman, *Adv. Appl. Math.*, 2:482, 1981, by the homology alignment algorithm of Needleman & Wunsch, *J. Mol. Biol.*, 48:443, 1970, by the search for similarity method of Pearson & Lipman, *Proc. Nat'l. Acad. Sci. USA*, 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see, generally, Ausubel et al., supra).

The phrase "substantially identical," in the context of two nucleic acids or polypeptides, refers to two or more sequences or subsequences that have at least 60%, preferably at least 70%, more preferably at least 80%, and most preferably at least 90% or al least 95% nucleotide or amino acid residue identity, when compared and aligned for maximum correspondence. Preferably, the substantial identity exists over a region of the sequences that is at least about 50 residues in length, more preferably over a region of at least about 100 residues, and most preferably the sequences are substantially identical over at least about 150 residues. In a preferred embodiment, the sequences are substantially identical over the entire length of a given nucleic acid or polypeptide. In certain embodiments of the invention, a nucleic acid or polypeptide (e.g., self-protein, -polypeptide, or -peptide or a nucleic acid encoding the self-protein, -polypeptide, or -peptide) is substantially identical to a specific nucleic acid or polypeptide disclosed herein.

"Self-molecules" as used herein include self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s). "Self protein(s), polypeptide(s), or peptide(s), or fragment(s) or derivative(s)" includes protein(s), polypeptide(s) or peptide(s) encoded within the genome of the animal; is produced or generated in the animal; may be modified posttranslationally at some time during the life of the animal; or is present in the animal non-physiologically. The term "non-physiological" or "non-physiologically" when used to describe the self-proteins, -polypeptides, or -peptides of this invention means a departure or deviation from the normal role or process in the animal for that self-protein, -polypeptide or -peptide. When referring to the self-protein, -polypeptide or -peptide as "associated with a disease" or "involved in a disease" it is understood to mean that the self-protein, -polypeptide, or -peptide may be modified in form or structure and thus be unable to perform its physiological role or process; or may be involved in the pathophysiology of the condition or disease either by inducing the pathophysiology, mediating or facilitating a pathophysiologic process; and/or by being the target of a pathophysiologic process. For example, in autoimmune disease, the immune system aberrantly attacks self-molecules such as self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s), causing damage and dysfunction of cells and tissues in which the self-molecule is expressed and/or present. Alternatively, the molecule can itself be expressed at non-physiological levels and/or function non-physiologically. For example in neurodegenerative diseases self-proteins are aberrantly expressed, and aggregate in lesions in the brain thereby causing neural dysfunction. In other cases, the self-molecule aggravates an undesired condition or process. For example in osteoarthritis, self-proteins including collagenases and matrix metalloproteinases aberrantly degrade cartilage covering the articular surface of joints. Examples of posttranslational modifications of self-protein(s), -polypeptide(s) or -peptide(s) are glycosylation, addition of lipid groups, dephosphorylation by phosphatases, addition of dimethylarginine residues, citrullination of fillagrin and fibrin by peptidyl arginine deiminase (PAD); alpha B-crystallin phosphorylation; citrullination of MBP; and SLE autoantigen proteolysis by caspases and granzymes. Immunologically, self-protein, -polypeptide or -peptide would all be considered host self-antigens and under normal physiological conditions are ignored by the host immune system through the elimination, inactivation, or lack of activation of immune cells that have the capacity to recognize self-antigens through a process designated "immune tolerance." Self-protein, -polypeptide, or -peptide does not include immune proteins, polypeptides, or peptides which are molecules expressed physiologically, specifically and exclusively by cells of the immune system for the purpose of regulating immune function. The immune system is the defense mechanism that provides the means to make rapid, highly specific, and protective responses against the myriad of potentially pathogenic microorganisms inhabiting the animal's world. Examples of immune protein(s), polypeptide(s) or peptide(s) are proteins comprising the T-cell receptor, immunoglobulins, cytokines including the type I interleukins, and the type II cytokines, including the interferons and IL-10, TNF-α, lymphotoxin, and the chemokines such as macrophage inflammatory protein-1alpha and beta, monocyte-chemotactic protein and RANTES, and other molecules directly involved in immune function such as Fas-ligand. There are certain immune proteins, polypeptide(s) or peptide (s) that are included in the self-protein, -polypeptide or -peptide of the invention and they are: class I MHC membrane glycoproteins, class II MHC glycoproteins and osteopontin. Self-protein, -polypeptide or -peptide does not include proteins, polypeptides, and peptides that are absent from the subject, either entirely or substantially, due to a genetic or acquired deficiency causing a metabolic or functional disorder, and are replaced either by administration of said protein, polypeptide, or peptide or by administration of a polynucleotide encoding said protein, polypeptide or peptide (gene therapy). Examples of such disorders include Duchenne' muscular dystrophy, Becker's muscular dystrophy, cystic fibrosis, phenylketonuria, galactosemia, maple syrup urine disease, and homocystinuria. Self-protein, -polypeptide or -peptide does not include proteins, polypeptides, and peptides expressed specifically and exclusively by cells which have characteristics that distinguish them from their normal counterparts, including: (1) clonality, representing proliferation of a single cell with a genetic alteration to form a clone of malignant cells, (2) autonomy, indicating that growth is not properly regulated, and (3) anaplasia, or the lack of normal coordinated cell differentiation. Cells have one or more of the foregoing three criteria are referred to either as neoplastic, cancer or malignant cells.

"Plasmids" and "vectors" are designated by a lower case p followed by letters and/or numbers. The starting plasmids are commercially available, publicly available on an unrestricted basis, or can be constructed from available plasmids in accord with published procedures. In addition, equivalent plasmids to those described are known in the art and will be apparent to the ordinarily skilled artisan. A "vector" or "plasmid" refers to any genetic element that is capable of replication by comprising proper control and regulatory elements when present in a host cell. For purposes of this invention examples of vectors or plasmids include, but are not limited to, plasmids, phage, transposons, cosmids, virus, and the like.

"Naked nucleic acid" as used herein refers to a nucleic acid molecule that is not encapsulated (such as, e.g., within a viral particle, bacterial cell, or liposome) and not complexed with a molecule that binds to the nucleic acid (such as, e.g., DEAE-dextran) nor otherwise conjugated to the nucleic acid (e.g., gold particles or polysaccharide-based supports).

"Treating," "treatment," or "therapy" of a disease or disorder shall mean slowing, stopping or reversing the progression of established disease, as evidenced by a decrease, cessation or elimination of either clinical or diagnostic symptoms, by administration of the immune modulatory nucleic acid of this invention. "Established disease" means the immune system is active, causing the affected tissues to be inflamed and abnormally infiltrated by leukocytes and lymphocytes. "Treating," "treatment," or "therapy" of a disease or disorder shall also mean slowing, stopping or reversing the disease's progression by administration of an immune modulatory nucleic acid in combination with a self-molecule. "Self-molecules" as used herein refer to self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s). "Treating," "treatment," or "therapy" of a disease or disorder shall further mean slowing, stopping or reversing the disease's progression by administration of an immune modulatory nucleic acid in combination with an immune modulatory therapeutic. "In combination with" when referring to a therapeutic regimen comprising an immune modulatory nucleic acid and another compound, for example DNA encoding a self-protein, -peptide, or -polypeptide, includes two or more compounds administered separately but together physically as co-administration in a vial, linked together as for example by conjugation, encoded by DNA on one or more vectors, or administered separately at different sites but temporally so close together to be considered by one of ordinary skill in the art to be administered "in combination." As used herein, ameliorating a disease and treating a disease are equivalent.

"Preventing," "prophylaxis" or "prevention" of a disease or disorder as used in the context of this invention refers to the administration of a immune modulatory sequence either alone or in combination with another compound as described herein, to prevent the occurrence or onset of a disease or disorder or some or all of the symptoms of a disease or disorder or to lessen the likelihood of the onset of a disease or disorder. "Preventing," "prophylaxis" or "prevention" of a disease or disorder as used in the context of this invention refers to the administration of an immune modulatory sequence in combination with self-molecules to prevent the occurrence or onset of a disease or disorder or some or all of the symptoms of a disease or disorder or to lessen the likelihood of the onset of a disease or disorder. "Preventing," "prophylaxis" or "prevention" of a disease or disorder as used in the context of this invention refers to the administration of an immune modulatory sequence in combination with an immune modulatory therapeutic to prevent the occurrence or onset of a disease or disorder or some or all of the symptoms of a disease or disorder or to lessen the likelihood of the onset of a disease or disorder. As used herein "immune modulatory therapeutics" refers to such molecules that have an immune modulatory or regulatory function when administered to a subject. Such immune modulatory therapeutics include cytokines, chemokines, steroids, or antibodies to antigens or autoantigens.

"Subjects" shall mean any animal, such as, for example, a human, non-human primate, horse, cow, dog, cat, mouse, rat, guinea pig or rabbit.

Autoimmune Diseases

The compositions and methods described herein are useful for the treatment or prevention of autoimmune disease. Several examples of autoimmune diseases associated with self molecules including self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), glycoprotein(s), or derivatives of self molecules present in the animal non-physiologically is set forth in the table below and is described below.

TABLE 1

| Autoimmune Disease | Tissue Targeted | Self-Protein(s) Associated With An Autoimmune Disease |
|---|---|---|
| Multiple sclerosis | central nervous system | myelin basic protein, proteolipid protein, myelin associated glycoprotein, cyclic nucleotide phosphodiesterase, yelin-associated glycoprotein, myelin- |

TABLE 1-continued

| Autoimmune Disease | Tissue Targeted | Self-Protein(s) Associated With An Autoimmune Disease |
|---|---|---|
| | | associated oligodendrocytic basic protein; alpha-B-crystalin; myelin oligodendrocyte glycoprotein |
| Guillian Barre Syndrome | peripheral nerv. sys. | peripheral myelin protein I and others |
| Insulin Dependent Diabetes Mellitus | Beta cells in islets of pancreas | tyrosine phosphatase IA2, IA-2β; glutamic acid decarboxylase (65 and 67 kDa forms), carboxypeptidase H, insulin, proinsulin, heat shock proteins, glima 38, islet cell antigen 69 KDa, p52, islet cell glucose transporter GLUT-2 |
| Rheumatoid Arthritis | synovial joints | Immunoglobulin, fibrin, filaggrin, type I, II, III, IV, V, IX, and XI collagens, GP-39, hnRNPs |
| Autoimmune Uveitis | iris, uveal tract | S-antigen, interphotoreceptor retinoid binding protein (IRBP), rhodopsin, recoverin |
| Primary Biliary Cirrhosis | biliary tree of liver | pyruvate dehydrogenase complexes (2-oxoacid dehydrogenase) |
| Autoimmune Hepatitis | Liver | Hepatocyte antigens, cytochrome P450 |
| Pemphigus vulgaris | Skin | Desmoglein-1, -3, and others |
| Myasthenia Gravis | nerve-muscle junct. | acetylcholine receptor |
| Autoimmune gastritis | stomach/ parietal cells | $H^+/K^+$ ATPase, intrinsic factor |
| Pernicious Anemia | Stomach | intrinsic factor |
| Polymyositis | Muscle | histidyl tRNA synthetase, other synthetases, other nuclear antigens |
| Autoimmune Thyroiditis | Thyroid | Thyroglobulin, thyroid peroxidase |
| Graves's Disease | Thyroid | Thyroid-stimulating hormone receptor |
| Psoriasis | Skin | Unknown |
| Vitiligo | Skin | Tyrosinase, tyrosinase-related protein-2 |
| Systemic Lupus Eryth. | Systemic | nuclear antigens: DNA, histones, ribonucleoproteins |
| Celiac Disease | Small bowel | Transglutaminase |

Multiple Sclerosis: Multiple sclerosis (MS) is the most common demyelinating disorder of the central nervous system (CNS) and affects 350,000 Americans and one million people worldwide. Onset of symptoms typically occurs between 20 and 40 years of age and manifests as an acute or sub-acute attack of unilateral visual impairment, muscle weakness, paresthesias, ataxia, vertigo, urinary incontinence, dysarthria, or mental disturbance (in order of decreasing frequency). Such symptoms result from focal lesions of demyelination which cause both negative conduction abnormalities due to slowed axonal conduction, and positive conduction abnormalities due to ectopic impulse generation (e.g. Lhermitte's symptom). Diagnosis of MS is based upon a history including at least two distinct attacks of neurologic dysfunction that are separated in time, produce objective clinical evidence of neurologic dysfunction, and involve separate areas of the CNS white matter. Laboratory studies providing additional objective evidence supporting the diagnosis of MS include magnetic resonance imaging (MRI) of CNS white matter lesions, cerebral spinal fluid (CSF) oligoclonal banding of IgG, and abnormal evoked responses. Although most patients experience a gradually progressive relapsing remitting disease course, the clinical course of MS varies greatly between individuals and can range from being limited to several mild attacks over a lifetime to fulminant chronic progressive disease. A quantitative increase in myelin-autoreactive T cells with the capacity to secrete IFN-gamma is associated with the pathogenesis of MS and EAE.

Rheumatoid Arthritis: Rheumatoid arthritis (RA) is a chronic autoimmune inflammatory synovitis affecting 0.8% of the world population. It is characterized by chronic inflammatory synovitis that causes erosive joint destruction. RA is mediated by T cells, B cells and macrophages.

Evidence that T cells play a critical role in RA includes the (1) predominance of CD4+ T cells infiltrating the synovium, (2) clinical improvement associated with suppression of T cell function with drugs such as cyclosporine, and (3) the association of RA with certain HLA-DR alleles. The HLA-DR alleles associated with RA contain a similar sequence of amino acids at positions 67-74 in the third hypervariable region of the beta chain that are involved in peptide binding and presentation to T cells. RA is mediated by autoreactive T cells that recognize a self molecule such as self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s), or an unidentified self biomolecule present in synovial joints or elsewhere in the host. Self-protein(s), -polypeptide(s) or -peptides of this invention also referred to as autoantigens are targeted in RA and comprise epitopes from type II collagen; hnRNP; A2/RA33; Sa; filaggrin; keratin; citrulline; cartilage proteins including gp39; collagens type I, III, IV, V, IX, XI; HSP-65/60; IgM (rheumatoid factor); RNA polymerase; hnRNP-B1; hnRNP-D; cardiolipin; aldolase A; citrulline-modified filaggrin and fibrin. Autoantibodies that recognize filaggrin peptides containing a modified arginine residue (de-iminated to form citrulline) have been identified in the serum of a high proportion of RA patients. Autoreactive T and B cell responses are both directed against the same immunodominant type II collagen (CII) peptide 257-270 in some patients.

Insulin Dependent Diabetes Mellitus: Human type I or insulin-dependent diabetes mellitus (IDDM) is characterized by autoimmune destruction of the Beta cells in the pancreatic islets of Langerhans. The depletion of Beta cells results in an inability to regulate levels of glucose in the blood. Overt diabetes occurs when the level of glucose in the blood rises above a specific level, usually about 250 mg/dl. In humans a long presymptomatic period precedes the onset of diabetes. During this period there is a gradual loss of pancreatic beta cell function. The development of disease is implicated by the presence of autoantibodies against insulin, glutamic acid decarboxylase, and the tyrosine phosphatase IA2 (LA2), each an example of a self-protein, -polypeptide or -peptide according to this invention.

Markers that may be evaluated during the presymptomatic stage are the presence of insulitis in the pancreas, the level and frequency of islet cell antibodies, islet cell surface antibodies, aberrant expression of Class II MHC molecules on pancreatic beta cells, glucose concentration in the blood, and the plasma concentration of insulin. An increase in the number of T lymphocytes in the pancreas, islet cell antibodies and blood glucose is indicative of the disease, as is a decrease in insulin concentration.

The Non-Obese Diabetic (NOD) mouse is an animal model with many clinical, immunological, and histopathological features in common with human IDDM. NOD mice spontaneously develop inflammation of the islets and destruction of the Beta cells, which leads to hyperglycemia and overt diabetes. Both CD4+ and CD8+ T cells are required for diabetes to develop, although the roles of each remain unclear. It has been shown with both insulin and GAD that when administered as proteins under tolerizing conditions, disease can be prevented and responses to the other self-antigens downregulated.

Importantly, NOD mice develop autoimmune diabetes in clean pathogen-free mouse houses, and in germ-free environments.

Human IDDM is currently treated by monitoring blood glucose levels to guide injection, or pump-based delivery, of recombinant insulin. Diet and exercise regimens contribute to achieving adequate blood glucose control.

Autoimmune Uveitis: Autoimmune uveitis is an autoimmune disease of the eye that is estimated to affect 400,000 people, with an incidence of 43,000 new cases per year in the U.S. Autoimmune uveitis is currently treated with steroids, immunosuppressive agents such as methotrexate and cyclosporin, intravenous immunoglobulin, and TNFalpha-antagonists.

Experimental autoimmune uveitis (EAU) is a T cell-mediated autoimmune disease that targets neural retina, uvea, and related tissues in the eye. EAU shares many clinical and immunological features with human autoimmune uveitis, and is induced by peripheral administration of uveitogenic peptide emulsified in Complete Freund's Adjuvant (CFA).

Self-proteins targeted by the autoimmune response in human autoimmune uveitis may include S-antigen, interphotoreceptor retinoid binding protein (IRBP), rhodop sin, and recoverin.

Primary Biliary Cirrhosis: Primary Biliary Cirrhosis (PBC) is an organ-specific autoimmune disease that predominantly affects women between 40-60 years of age. The prevalence reported among this group approaches 1 per 1,000. PBC is characterized by progressive destruction of intrahepatic biliary epithelial cells (IBEC) lining the small intrahepatic bile ducts (Nishio et al., *Semin Liver Dis*, 22:291, 2002). This leads to obstruction and interference with bile secretion, causing eventual cirrhosis. Association with other autoimmune diseases characterized by epithelium lining/secretory system damage has been reported, including Sjogren's Syndrome, CREST Syndrome, Autoimmune Thyroid Disease and Rheumatoid Arthritis.

A murine model of experimental autoimmune cholangitis (EAC) uses intraperitoneal (i.p.) sensitization with mammalian PDC in female SJL/J mice, inducing non-suppurative destructive cholangitis (NSDC) and production of AMA (Jones, *J Clin Pathol*, 53:813-21, 2000). The MRL/lpr mouse model of SLE has also been shown to develop a PBC like illness characterized by the development of autoantibodies directed against the alpha ketoglutarate dehydrogenase complex.

Other Autoimmune Diseases And Associated Self-Protein(s), -Polypeptide(s) Or -Peptide(s): Autoantigens for myasthenia gravis may include epitopes within the acetylcholine receptor. Autoantigens targeted in pemphigus vulgaris may include desmoglein-3. Sjogren's syndrome antigens may include SSA (Ro); SSB (La); and fodrin. The dominant autoantigen for pemphigus vulgaris may include desmoglein-3. Panels for myositis may include tRNA synthetases (e.g., threonyl, histidyl, alanyl, isoleucyl, and glycyl); Ku; Scl; SS-A; U1-sn-ribonuclear proteins; Mi-1; Mi-1; Jo-1; Ku; and SRP. Panels for scleroderma may include Scl-70; centromere; U1-sn-ribonuclear proteins; and fibrillarin. Panels for pernicious anemia may include intrinsic factor; and glycoprotein beta subunit of gastric H/K ATPase. Epitope Antigens for systemic lupus erythematosus (SLE) may include DNA; phospholipids; nuclear antigens; U1 ribonucleoprotein; Ro60 (SS-A); Ro52 (SS-A); La (SS-B); calreticulin; Grp78; Scl-70; histone; Sm protein; serine-arginine splicing factors, and chromatin, etc. For Grave's disease epitopes may include the Na+/I− symporter; thyrotropin receptor; Tg; and TPO.

Other Diseases

Several examples of other diseases associated with self-protein(s), -polypeptide(s) or -peptide(s) present in the animal non-physiologically are set forth in the table and described below.

Inflammatory Diseases

Osteoarthritis and Degenerative Joint Diseases: Osteoarthritis (OA) affects 30% of people over 60 years of age, and is the most common joint disease of humans. Osteoarthritis represents the degeneration and failure of synovial joints, and involves breakdown of the articular cartilage.

Cartilage is composed primarily of proteoglycans, which provide stiffness and ability to withstand load, and collagens that provide tensile and resistance to sheer strength. Chondrocytes turn over and remodel normal cartilage by producing and secreting latent collagenases, latent stromelysin, latent gelatinase, tissue plasminogen activator and other associated enzymes, each of which alone or in combination is a self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s) of this invention. Several inhibitors, including tissue inhibitor of metalloproteinase (TIMP) and plasminogen activator inhibitor (PAI-1), are also produced by chondrocytes and limit the degradative activity of neutral metalloproteinases, tissue plasminogen activator, and other enzymes. These degradative enzymes and inhibitors, alone or in combination, are the self-protein(s), polypeptide(s) or peptide(s) of this invention. These degradative enzymes and inhibitors coordinate remodeling and maintenance of normal cartilage. In OA, dysregulation of this process results in the deterioration and degradation of cartilage. Most patients with OA also have some degree of inflammation, including warmth and swelling of joints. In early OA there are abnormal alterations in the arrangement and size of collagen fibers. Metalloproteinases, cathepsins, plasmin, and other self molecules alone or in combination are self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s) of this invention, cause significant cartilage matrix loss. Initially increased chondrocyte production of proteoglycans and cartilage results in the articular cartilage being thicker than normal. The articular cartilage then thins and softens as a result of the action of degradative enzymes including collagenases, stromelysin, gelatinase, tissue plasminogen activator and other related enzymes, alone or in combination are self molecules such as self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s) of this invention. Inflammatory molecules such as IL-1, cathepsins, and plasmin may promote the degeneration and breakdown of cartilage, alone or in combination, and are self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s) of this invention. The softer and thinner cartilage is much more susceptible to damage by mechanical stress. These factors lead to the breakdown of the cartilage surface and the formation of vertical clefts (fibrillation). Erosions in the cartilage surface form, and extend to bone in end-stage disease. Chondrocytes initially replicate and form clusters, and at end-stage the cartilage is hypocelluar. Remodeling and hypertrophy of bone are significant features of OA.

Current therapies for OA include rest, physical therapy to strengthen muscles supporting the joint, braces and other supportive devices to stabilize the joint, non-steroidal anti-inflammatory agents, acetaminophen, and other analgesics. In end-stage bone-on-bone OA of joints critical for activities of daily living, such as the knees or hips, surgical joint replacement is performed.

Spinal Cord Injury: It is estimated that there are approximately 11,000 new cases of spinal cord injury every year in the U.S. and that the overall prevalence is a total of 183,000 to 230,000 cases in the U.S. presently (Stover et al., Arch Phys Med Rehabil, 80, 1365-71, 1999). Recovery from spinal cord injury is very poor and results in devastating irreversible neurologic disability. Current treatment of acute spinal cord injury consists of mechanical stabilization of the injury site, for example by surgical intervention, and the administration of parenteral steroids. These interventions have done little to reduce the incidence of permanent paralysis following spinal cord injury. Treatment of chronic spinal cord injury is focused on maintenance of quality of life such as the management of pain, spasticity, and bladder function. No currently available treatment addresses the recovery of neurologic function. In the acute stage immediately following injury, inflammation is prominent, and swelling associated with cord damage is a major cause of morbidity. This inflammation is controlled in part with high doses of systemic corticosteroids.

Graft Versus Host Disease: One of the greatest limitations of tissue and organ transplantation in humans is rejection of the tissue transplant by the recipient's immune system. It is well established that the greater the matching of the MHC class I and II (HLA-A, HLA-B, and HLA-DR) alleles between donor and recipient the better the graft survival. Graft versus host disease (GVHD) causes significant morbidity and mortality in patients receiving transplants containing allogeneic hematopoietic cells. This is due in part to inflammation in the skin and in other target organs. Hematopoietic cells are present in bone-marrow transplants, stem cell transplants, and other transplants. Approximately 50% of patients receiving a transplant from a HLA-matched sibling will develop moderate to severe GVHD, and the incidence is much higher in non-HLA-matched grafts. One-third of patients who develop moderate to severe GVHD will die as a result. T lymphocytes and other immune cell in the donor graft attack the recipients cells that express polypeptides variations in their amino acid sequences, particularly variations in proteins encoded in the major histocompatibility complex (MHC) gene complex on chromosome 6 in humans. The most influential proteins for GVHD in transplants involving allogeneic hematopoietic cells are the highly polymorphic (extensive amino acid variation between people) class I proteins (HLA-A, -B, and -C) and the class II proteins (DRB1, DQB1, and DPB1) (Appelbaum, Nature 411:385-389, 2001). Even when the MHC class I alleles are serologically 'matched' between donor and recipient, DNA sequencing reveals there are allele-level mismatches in 30% of cases providing a basis for class I-directed GVHD even in matched donor-recipient pairs (Appelbaum, Nature, 411, 385-389, 2001). GVHD frequently causes damage to the skin, intestine, liver, lung, and pancreas. GVHD is treated with glucocorticoids, cyclosporine, methotrexate, fludarabine, and OKT3.

Tissue Transplant Rejection: Immune rejection of tissue transplants, including lung, heart, liver, kidney, pancreas, and other organs and tissues, is mediated by immune responses in the transplant recipient directed against the transplanted organ. Allogeneic transplanted organs contain proteins with variations in their amino acid sequences when compared to the amino acid sequences of the transplant recipient. Because the amino acid sequences of the transplanted organ differ from those of the transplant recipient they frequently elicit an immune response in the recipient against the transplanted organ. The immune response encompasses responses by both the innate and the acquired immune system and is characterized by inflammation in the target organ. Rejection of transplanted organs is a major complication and limitation of tissue transplant, and can cause failure of the transplanted organ in the recipient. The chronic inflammation that results from rejection frequently leads to dysfunction in the transplanted organ. Transplant recipients are currently treated with a variety of immunosuppressive agents to prevent and suppress rejection. These agents include glucocorticoids, cyclosporin A, Cellcept, FK-506, and OKT3.

Immune Modulatory Nucleic Acids and Related Compositions

In one aspect, the immune modulatory nucleic acids of the invention comprise the following core hexamer:

5'-purine-pyrimidine-[X]-[Y]-pyrimidine-pyrimidine-3'
or

5'-purine-purine-[X]-[Y]-pyrimidine-pyrimidine-3' wherein X and Y are any naturally occurring or synthetic nucleotides, except that X and Y cannot be cytosine-guanine.

The core hexamer of IMSs, referred to herein as the immune modulatory sequence motif comprising a dinucleotide motif, can be flanked 5' and/or 3' by any composition or number of nucleotides or nucleosides. Preferably, immune modulatory nucleic acids comprising immune modulatory sequence motifs are oligonucleotides ranging between 6 and 100 base pairs in size, and most preferably 16-50 base pairs in size. Immune modulatory nucleic acids can also be delivered as part of larger pieces of DNA, ranging from 100 to 100,000 base pairs. IMSs can be incorporated in, or already occur in, DNA plasmids, viral vectors and genomic DNA. Immune modulatory nucleic acids can also range from 6 (no flanking sequences) to 10,000 base pairs, or larger, in size. Sequences present which flank the hexamer core can be constructed to substantially match flanking sequences present in any known immunoinhibitory sequences. For example, the IMS having the sequence TGACTGTG-Purine-Pyrimidine-X-Y-Pyrimidine-Pyrimidine-AGAGATGA (SEQ ID NO:298), comprises the flanking sequences TGACTGTG and AGAGATGA. Another preferred flanking sequence incorporates a series of pyrimidines (C, T, and U), either as an individual pyrimidine repeated two or more times, or a mixture of different pyrimidines two or more in length. Different flanking sequences have been used in testing inhibitory modulatory sequences. Further examples of flanking sequences for inhibitory nucleic acids are contained in the following references: U.S. Pat. Nos. 6,225,292 and 6,339,068; Zeuner et al., *Arthritis and Rheumatism*, 46:2219-24, 2002.

Particular IMSs of the invention comprise the following hexamer sequences:

1. 5'-purine-pyrimidine-[X]-[Y]-pyrimidine-pyrimidine-3' IMSs containing GG dinucleotide cores: GTGGTT (SEQ ID NO:1), ATGGTT (SEQ ID NO:2), GCGGTT (SEQ ID NO:3), ACGGTT (SEQ ID NO:4), GTGGCT (SEQ ID NO:5), ATGGCT (SEQ ID NO:6), GCGGCT (SEQ ID NO:7), ACGGCT (SEQ ID NO:8), GTGGTC (SEQ ID NO:9), ATGGTC (SEQ ID NO:10), GCGGTC (SEQ ID NO:11), ACGGTC (SEQ ID NO:12), and so forth;
2. 5'-purine-pyrimidine-[X]-[1]-pyrimidine-pyrimidine-3' IMSs containing GC dinucleotides cores: GTGCTT (SEQ ID NO:13), ATGCTT (SEQ ID NO:14), GCGCTT (SEQ ID NO:15), ACGCTT (SEQ ID NO:16), GTGCCT (SEQ ID NO:17), ATGCCT (SEQ ID NO:18), GCGCCT (SEQ ID NO:19), ACGCCT (SEQ ID NO:20), GTGCTC (SEQ ID NO:21), ATGCTC (SEQ ID NO:22), GCGCTC (SEQ ID NO:23), ACGCTC (SEQ ID NO:24), and so forth;
3. Guanine and inosine substitutes for adenine and/or uridine substitutes for cytosine or thymine and those substitutions can be made as set forth based on the guidelines above.

A previously disclosed immune inhibitory sequence or IIS, was shown to inhibit immunostimulatory sequences (ISS) activity containing a core dinucleotide, CpG. U.S. Pat. No. 6,225,292. This IIS, in the absence of an ISS, was shown for the first time by this invention to prevent and treat autoimmune disease either alone or in combination with DNA polynucleotide therapy. This IIS contained the core hexamer region having the sequence AAGGTT (SEQ ID NO:28). That sequence is referred to herein as an immune modulatory sequence or IMS. Other related IISs with a similar motif included within the IMSs of this invention are:
1. 5'-purine-purine-[X]-[Y]-pyrimidine-pyrimidine-3' IMSs containing GG dinucleotide cores: GGGGTT (SEQ ID NO:25), AGGGTT (SEQ ID NO:26), GAGGTT (SEQ ID NO:27, AAGGTT (SEQ ID NO:28), GGGGCT (SEQ ID NO:29), AGGGCT (SEQ ID NO:30), GAGGCT (SEQ ID NO:31), AAGGCT (SEQ ID NO:32), GGGGTC (SEQ ID NO:33), AGGGTC (SEQ ID NO:34), GAGGTC (SEQ ID NO:35), AAGGTC (SEQ ID NO:36), and so forth;
2. 5'-purine-purine-[X]-[Y]-pyrimidine-pyrimidine-3' IMSs containing GC dinucleotide cores: GGGCTT (SEQ ID NO:37), AGGCTT (SEQ ID NO:38), GAGCTT (SEQ ID NO:39, AAGCTT (SEQ ID NO:40), GGGCCT (SEQ ID NO:41), AGGCCT (SEQ ID NO:42), GAGCCT (SEQ ID NO:43), AAGCCT (SEQ ID NO:44), GGGCTC (SEQ ID NO:45), AGGCTC (SEQ ID NO:46), GAGCTC (SEQ ID NO:47), AAGCTC (SEQ ID NO:48), and so forth;
3. Guanine and inosine substitutions for adenine and/or uridine substitutions for cytosine or thymine can be made as set forth based on the guidelines above.

In certain embodiments of the present invention, the core hexamer region of the IMS is flanked at either the 5' or 3' end, or at both the 5' and 3' ends, by a polyG region. A "polyG region" or "polyG motif" as used herein means a nucleic acid region consisting of at least two (2) contiguous guanine bases, typically from 2 to 30 or from 2 to 20 contiguous guanines. In some embodiments, the polyG region has from 2 to 10, from 4 to 10, or from 4 to 8 contiguous guanine bases. In certain preferred embodiments, the flanking polyG region is adjacent to the core hexamer. In yet other embodiments, the polyG region is linked to the core hexamer by a non-polyG region (non-polyG linker); typically, the non-polyG linker region has no more than 6, more typically no more than 4 nucleotides, and most typically no more than 2 nucleotides.

Immune modulatory nucleic acids can be obtained from existing nucleic acid sources, including genomic DNA, plasmid DNA, viral DNA and cDNA. In certain preferred embodiments, the immune modulatory nucleic acids are synthetic oligonucleotides produced by oligonucleotide synthesis. IMS can be part of single-strand or double-stranded DNA, RNA and/or oligonucleosides.

Immune modulatory nucleic acids are preferentially nucleic acids having one or more IMS regions that contain unmethylated GpG oligonucleotides. In alternative embodiments, one or more adenine or cytosine residues of the IMS region are methylated. In eukaryotic cells, typically cytosine and adenine residues can be methylated.

Immune modulatory nucleic acids can be stabilized and/or unstabilized oligonucleotides. Stabilized oligonucleotides mean oligonucleotides that are relatively resistant to in vivo degradation by exonucleases, endonucleases and other degradation pathways. Preferred stabilized oligonucleotides have modified phophate backbones, and most preferred oligonucleotides have phophorothioate modified phosphate backbones in which at least one of the phosphate oxygens is replaced by sulfur. Backbone phosphate group modifications, including methylphosphonate, phosphorothioate, phophoroamidate and phosphorodithionate internucleotide linkages, can provide antimicrobial properties on IMSs. The immune modulatory nucleic acids are preferably stabilized oligonucleotides, preferentially using phosphorothioate stabilized oligonucleotides.

Alternative stabilized oligonucleotides include: alkylphosphotriesters and phosphodiesters, in which the charged oxygen is alkylated; arylphosphonates and alkylphosphonates, which are nonionic DNA analogs in which the charged phosphonate oxygen is replaced by an aryl or alkyl group; or/and oligonucleotides containing hexaethyleneglycol or tetraethyleneglycol, or another diol, at either or both termini. Alternative steric configurations can be used to attach sugar moieties to nucleoside bases in IMS regions.

The nucleotide bases of the IMS region which flank the modulating dinucleotides may be the known naturally occurring bases or synthetic non-natural bases. Oligonucleosides may be incorporated into the internal region and/or termini of the IMS-ON using conventional techniques for use as attachment points, that is as a means of attaching or linking other molecules, for other compounds, including self-molecules or as attachment points for additional immune modulatory therapeutics. The base(s), sugar moiety, phosphate groups and termini of the IMS-ON may also be modified in any manner known to those of ordinary skill in the art to construct an IMS-ON having properties desired in addition to the modulatory activity of the IMS-ON. For example, sugar moieties may be attached to nucleotide bases of IMS-ON in any steric configuration.

The techniques for making these phosphate group modifications to oligonucleotides are known in the art and do not require detailed explanation. For review of one such useful technique, the intermediate phosphate triester for the target oligonucleotide product is prepared and oxidized to the naturally occurring phosphate triester with aqueous iodine or with other agents, such as anhydrous amines. The resulting oligonucleotide phosphoramidates can be treated with sulfur to yield phophorothioates. The same general technique (excepting the sulfur treatment step) can be applied to yield methylphosphoamidites from methylphosphonates. For more details concerning phosphate group modification techniques, those of ordinary skill in the art may wish to consult U.S. Pat. Nos. 4,425,732; 4,458,066; 5,218,103 and 5,453,496, as well as Tetrahedron, *Lett*. at 21:4149 25 (1995), 7:5575 (1986), 25:1437 (1984) and *Journal Am. Chem Soc.*, 93:6657 (1987), the disclosures of which are incorporated herein for the purpose of illustrating the level of knowledge in the art concerning the composition and preparation of immune modulatory nucleic acids.

A particularly useful phosphate group modification is the conversion to the phosphorothioate or phosphorodithioate forms of the IMS-ON oligonucleotides. Phosphorothioates and phosphorodithioates are more resistant to degradation in vivo than their unmodified oligonucleotide counterparts, making the IMS-ON of the invention more available to the host.

IMS-ON can be synthesized using techniques and nucleic acid synthesis equipment which are well-known in the art. For reference in this regard, see, e.g., Ausubel, et al., *Current Protocols in Molecular Biology*, Chs. 2 and 4 (Wiley Interscience, 1989); Maniatis, et al., *Molecular Cloning: A Laboratory Manual* (Cold Spring Harbor Lab., New York, 1982); U.S. Pat. No. 4,458,066 and U.S. Pat. No. 4,650,675. These references are incorporated herein by reference for the purpose of demonstrating the level of knowledge in the art concerning production of synthetic oligonucleotides.

Alternatively, IMS-ON can be obtained by mutation of isolated microbial ISS-ODN to substitute a competing dinucleotide for the naturally occurring CpG motif and the flanking nucleotides. Screening procedures which rely on nucleic acid hybridization make it possible to isolate any polynucleotide sequence from any organism, provided the appropriate probe or antibody is available. Oligonucleotide probes, which correspond to a part of the sequence encoding the protein in question, can be synthesized chemically. This requires that short, oligo-peptide stretches of amino acid sequence must be known. The DNA sequence encoding the protein can also be deduced from the genetic code, however, the degeneracy of the code must be taken into account.

For example, a cDNA library believed to contain an ISS-containing polynucleotide can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucleotide of interest. Alternatively, a cDNA library can be screened indirectly for expression of peptides of interest having at least one epitope using antibodies specific for the peptides. Such antibodies can be either polyclonally or monoclonally derived and used to detect expression product indicative of the presence of cDNA of interest.

Once the ISS-containing polynucleotide has been obtained, it can be shortened to the desired length by, for example, enzymatic digestion using conventional techniques. The CpG motif in the ISS-ODN oligonucleotide product is then mutated to substitute an "inhibiting" dinucleotide—identified using the methods of this invention—for the CpG motif. Techniques for making substitution mutations at particular sites in DNA having a known sequence are well known, for example M13 primer mutagenesis through PCR. Because the IMS is non-coding, there is no concern about maintaining an open reading frame in making the substitution mutation. However, for in vivo use, the polynucleotide starting material, ISS-ODN oligonucleotide intermediate or IMS mutation product should be rendered substantially pure (i.e., as free of naturally occurring contaminants and LPS as is possible using available techniques known to and chosen by one of ordinary skill in the art).

The immune modulatory nucleic acids of the present invention can contain IMSs alone or incorporated in cis or in trans with other nucleic acid regions such as, for example, into a recombinant self-vector (plasmid, cosmid, virus or retrovirus) which may in turn code for any self-protein(s), -polypeptide(s), or -peptide(s) deliverable by a recombinant expression vector. In certain embodiments, the IMSs are administered without incorporation into a vector. Alternatively, in other embodiments, the IMSs are incorporated into a vector such as, for example, an expression vector, which may be accomplished, for example, using conventional techniques as known to one of ordinary skill in the art (see, e.g., Ausubel, *Current Protocols in Molecular Biology*, supra).

For example, construction of recombinant expression vectors employs standard ligation techniques. For analysis to confirm correct sequences in vectors constructed, the ligation mixtures may be used to transform a host cell and successful transformants selected by antibiotic resistance where appropriate. Vectors from the transformants are prepared, analyzed by restriction and/or sequenced by, for example, the method of Messing, et al., *Nucleic Acids Res.*, 9:309, 1981, the method of Maxam, et al., *Methods in Enzymology*, 65:499, 1980, or other suitable methods which will be known to those skilled in the art. Size separation of cleaved fragments is performed using conventional gel electrophoresis as described, for example, by Maniatis, et al., *Molecular Cloning*, pp. 133-134, 1982.

Host cells may be transformed with the expression vectors of this invention and cultured in conventional nutrient media modified as is appropriate for inducing promoters, selecting transformants or amplifying genes. The culture conditions, such as temperature, pH and the like are those previously used with the host cell selected for expression, and will be apparent to the ordinarily skilled artisan.

If a recombinant vector is utilized as a carrier for the IMS-ON of the invention, plasmids and cosmids are particularly preferred for their lack of pathogenicity. However, plasmids and cosmids are subject to degradation in vivo more quickly than viruses and therefore may not deliver an adequate dosage of IMS-ON to prevent or treat an inflammatory or autoimmune disease.

In a related aspect, a nucleic acid vector is provided in which a non-CpG dinucleotide is substituted for one or more CpG dinucleotides of the formula 5'-purine-pyrimidine-C-G-pyrimidine-pyrimidine-3' or 5'-purine-purine-C-G-pyrimidine-pyrimidine-3', thereby producing a vector in which IIS-associated immunostimulatory activity is reduced. Such vectors are useful, for example, in methods for administering immune modulatory nucleic acids and/or for administering a self vector encoding one or more self-protein(s), -polypeptides(s), or -peptide(s). For example, the cytosine of the CpG dinucleotide can be substituted with guanine, thereby yielding an IMS region having a GpG motif of the formula 5'-purine-pyrimidine-G-G-pyrimidine-pyrimidine-3' or 5'-purine-purine-G-G-pyrimidine-pyrimidine-3'. The cytosine can also be substituted with any other non-cytosine nucleotide. The substitution can be accomplished, for example, using site-directed mutagenesis. Typically, the substituted CpG motifs are those CpGs that are not located in important control regions of the vector (e.g., promoter regions). In addition, where the CpG is located within a coding region of an expression vector, the non-cytosine substitution is typically selected to yield a silent mutation or a codon corresponding to a conservative substitution of the encoded amino acid.

For example, in certain embodiments, a modified pVAX1 vector is provided in which one or more CpG dinucleotides of the formula 5'-purine-pyrimidine-C-G-pyrimidine-pyrimidine-3' is mutated by substituting the cytosine of the CpG dinucleotide with a non-cytosine nucleotide. The pVAX1 vector is known in the art and is commercially available from Invitrogen (Carlsbad, Calif.). In one exemplary embodiment, the modified pVAX1 vector has the following cytosine to non-cytosine substitutions within a CpG motif:

cytosine to guanine at nucleotides 784, 1161, 1218, and 1966;

cytosine to adenine at nucleotides 1264, 1337, 1829, 1874, 1940, and 1997; and cytosine to thymine at nucleotides 1963 and 1987;

with additional cytosine to guanine mutations at nucleotides 1831, 1876, 1942, and 1999 (The nucleotide number designations as set forth above are according to the numbering system for pVAX1 provided by Invitrogen.) (See Example 3, infra.)

Functional Properties of IMSs

There are several mechanisms to explain the immunomodulatory properties of IMSs, and these include mechanisms independent of ISS (CpG)-mediated immune stimulation.

"Modulation of, modulating or altering an immune response" as used herein refers to any alteration of existing or potential immune response(s) against self-molecules, including but not limited to nucleic acids, lipids, phospholipids, carbohydrates, self-protein(s), -polypeptide(s), -peptide(s), protein complexes, ribonucleoprotein complexes, or derivative(s) thereof that occurs as a result of administration of an immune modulatory nucleic acid. Such modulation includes any alteration in presence, capacity or function of any immune cell involved in or capable of being involved in an immune response. Immune cells include B cells, T cells, NK cells, NK T cells, professional antigen-presenting cells, non-professional antigen-presenting cells, inflammatory cells, or any other cell capable of being involved in or influencing an immune response. Modulation includes any change imparted on an existing immune response, a developing immune response, a potential immune response, or the capacity to induce, regulate, influence, or respond to an immune response. Modulation includes any alteration in the expression and/or function of genes, proteins and/or other molecules in immune cells as part of an immune response.

Modulation of an immune response includes, but is not limited to: elimination, deletion, or sequestration of immune cells; induction or generation of immune cells that can modulate the functional capacity of other cells such as autoreactive lymphocytes, APCs, or inflammatory cells; induction of an unresponsive state in immune cells, termed anergy; increasing, decreasing or changing the activity or function of immune cells or the capacity to do so, including but not limited to altering the pattern of proteins expressed by these cells. Examples include altered production and/or secretion of certain classes of molecules such as cytokines, chemokines, growth factors, transcription factors, kinases, costimulatory molecules, or other cell surface receptors; or any combination of these modulatory events.

The immune responses are characterized by helper T cells and immune responses that produce cytokines including IL-12 and IFN gamma, and are associated with B cells that produce antibodies of certain isotypes (generally, IgG2a in mice; generally, IgG1 and IgG3 in humans). Th1-type immune responses predominate in autoimmune diseases, and are associated with autoimmune-mediated tissue injury. In contrast, Th2 immune responses are characterized by helper T cells and immune responses that produce cytolines including IL-4 and IL-10, and are associated with B cells that produce antibodies of certain isotypes (generally, IgG1 in mice; generally, IgG2 and IgG4 in humans). Th2-type immune responses are associated with protection against autoimmune-mediated tissue injury in rodent and human autoimmunity.

Immune modulatory nucleic acids could modulate immune responses by eliminating, sequestering, or turning-off immune cells mediating or capable of mediating an undesired immune response; inducing, generating, or turning on immune cells that mediate or are capable of mediating a protective immune response; changing the physical or functional properties of immune cells (such as suppressing a Th1-type response and/or inducing a Th2-type response); or a combination of these effects. Examples of measurements of the modulation of an immune response include, but are not limited to, examination of the presence or absence of immune cell populations (using flow cytometry, immunohistochemistry, histology, electron microscopy, the polymerase chain reaction); measurement of the functional capacity of immune cells including ability or resistance to proliferate or divide in response to a signal (such as using T cell proliferation assays and pepscan analysis based on 3H-thymidine incorporation following stimulation with anti-CD3 antibody, anti-T cell receptor antibody, anti-CD28 antibody, calcium ionophores, PMA, antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (by flow cytometry, enzyme-linked immunosorbent assays, Western blot analysis, protein microarray analysis, immunoprecipitation analysis); measurement of biochemical markers of activation of immune cells or signaling pathways within immune cells (Western blot and immunoprecipitation analysis of tyrosine, serine or threonine phosphorylation, polypeptide cleavage, and formation or dissociation of protein complexes; protein array analysis; DNA transcriptional profiling using DNA arrays or subtractive hybridization); measurements of cell death by apoptosis, necrosis, or other mechanisms (annexin V staining, TUNEL assays, gel electrophoresis to measure DNA laddering, histology; fluorogenic caspase assays, Western blot analysis of caspase substrates); measurement of the genes, proteins, and other molecules produced by immune cells (Northern blot analysis, polymerase chain reaction, DNA microarrays, protein microarrays, 2-dimentional gel electrophoresis, Western blot analysis, enzyme linked immunosorbent assays, flow cytometry); and measurement of clinical outcomes such as improvement of autoimmune, neurodegenerative, and other disease outcomes (clinical scores, requirements for use of additional therapies, functional status, imaging studies).

Other investigators have carried out experiments to evaluate the mechanisms of action of ISSs. Those investigators demonstrated that neutralizing or suppressive IISs (GpGs) motifs, block ISS (CpG) immune stimulation (Krieg et al., *PNAS,* 95:12631, 1998; U.S. Pat. Nos. 6,225,292 and 6,339, 068). The IISs in those experiments were used to counteract, inhibit, compete, or overcome the effects of ISSs (from such sources such as bacteria, viruses, parasites, and DNA given exogenously such as in DNA vaccination or gene therapy). ISSs and IISs have been shown to enter the same cell, suggesting that one mechanism by which IISs inhibit ISSs is through direct competition within the same cell (Yamada et al., *J. Immunology,* 2002, 169:5590).

Methods of Administration

The immune modulatory nucleic acids are prepared as a composition comprising a pharmaceutically acceptable carrier. Pharmaceutically acceptable carriers preferred for use with the immune modulatory nucleic acid of the invention may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. A composition of immune modulatory nucleic acids may also be lyophilized using means well known in the art, for subsequent reconstitution and use according to the invention. Immune modulatory nucleic acids can be mixed into a pharmaceutical composition that contain multiple copies of an individual IMS, a combination of different IMSs, a combination of IMSs where each is present at the same relative molar concentration, a combinations of IMSs where each is present at different relative molar concentrations, or individual and/or different IMSs incorporated into recombinant expression vector plasmids, linear polynucleotides, viruses and viral vectors, bacteria, and other live, inactivated or synthetic compositions containing oligonucleotides.

The immune modulatory nucleic acids of this invention can be formulated with salts for use as pharmaceuticals. Immune modulatory nucleic acids can be prepared with non-toxic inorganic or organic bases. Inorganic base salts include sodium, potassium, zinc, calcium, aluminum, magnesium, etc. Organic non-toxic bases include salts of primary, secondary and tertiary amines, and the like. Such immune modulatory nucleic acids can be formulated in lyophilized form for reconstitution prior to delivery, such as sterile water or a salt solution. Alternatively, immune modulatory nucleic acids can be formulated in solutions, suspensions, or emulsions involving water- or oil-based vehicles for delivery. Immune modulatory nucleic acids can be lyophilized and then reconstituted with sterile water prior to administration.

As known to those ordinarily skilled in the art, a wide variety of methods exist to deliver nucleic acids to subjects. In some embodiments, the immune modulatory nucleic acid is administered as a naked nucleic acid. For example, in certain embodiments, viral particles (e.g., adenovirus particles, see, e.g., Curiel et al., *Am. J Respir. Cell Mol. Biol.*, 6:247-52, 1992, supra) are mixed with the naked nucleic acid prior to administration to produce a formulation that contains viral particles not encapsulating the nucleic acid but which still facilitate its delivery. Alternatively, in other embodiments, the immune modulatory nucleic acid is encapsulated or is complexed with molecule that binds to the nucleic acid such as, for example, cationic substances (e.g., DEAE-dextran or cationic lipids). For example, liposomes represent effective means to formulate and deliver oligonucleotide and/or self-polynucleotide. In other specific embodiments, the immune modulatory nucleic acid is incorporated into a viral vector, viral particle, or bacterium for pharmacologic delivery. Viral vectors can be infection competent, attenuated (with mutations that reduce capacity to induce disease), or replication-deficient. In other embodiments, the nucleic acid is conjugated to solid supports including gold particles, polysaccharide-based supports, or other particles or beads that can be injected, inhaled, or delivered by particle bombardment (ballistic delivery).

Methods for delivering nucleic acid preparations are known in the art. See, e.g., U.S. Pat. Nos. 5,399,346, 5,580,859, 5,589,466. A number of viral based systems have been developed for transfer into mammalian cells. For example, retroviral systems have been described (U.S. Pat. No. 5,219,740; (Miller et al., *Biotechniques*, 7:980-990, 1989); (Miller, A. D., *Human Gene Therapy*, 1:5-14, 1990); (Scarpa et al., *Virology*, 180:849-852, 1991); (Burns et al., *Proc. Natl. Acad. Sci. USA*, 90:8033-8037, 1993); and (Boris-Lawrie and Temin, *Cur. Opin. Genet. Develop.*, 3:102-109, 1993). A number of adenovirus vectors have also been described, see, e.g., (Haj-Ahmad et al., *J. Virol.*, 57:267-274, 1986); (Bett et al., *J. Virol.*, 67:5911-5921, 1993); (Mitereder et al., *Human Gene Therapy*, 5:717-729, 1994); (Seth et al., *J. Virol.*, 68:933-940, 1994); (Barr et al., *Gene Therapy*, 1:51-58, 1994); (Berkner, K. L., *BioTechniques*, 6:616-629, 1988); and (Rich et al., *Human Gene Therapy*, 4:461-476, 1993). Adeno-associated virus (AAV) vector systems have also been developed for nucleic acid delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); (Lebkowski et al., *Molec. Cell. Biol*, 8:3988-3996, 1988); (Vincent et al., *Vaccines*, 90 (Cold Spring Harbor Laboratory Press) 1990); (Carter, B. J., *Current Opinion in Biotechnology*, 3:533-539, 1992); (Muzyczka, N., *Current Topics in Microbiol. And Immunol.*, 158:97-129, 1992); (Kotin, R. M., *Human Gene Therapy*, 5:793-801, 1994); Shelling et al., *Gene Therapy*, 1:165-169, 1994); and Zhou et al., *J. Exp. Med.*, 179:1867-1875, 1994).

The IMSs of this invention can also be delivered without a vector. For example, the molecule can be packaged in liposomes prior to delivery to the subject. Lipid encapsulation is generally accomplished using liposomes that are able to stably bind or entrap and retain nucleic acid. For a review of the use of liposomes as carriers for delivery of nucleic acids, see, (Hug et al., *Biochim. Biophys. Acta.*, 1097:1-17, 1991); Straubinger et al., in *Methods of Enzymology*, Vol. 101, pp. 512-527, 1983). For example, lipids that can be used in accordance with the invention include, but are not limited to, DOPE (Dioleoyl phosphatidylethanolamine), cholesterol, and CUDMEDA (N-(5-cholestrum-3-ol 3 urethanyl)-N',N'-dimethylenediamine). As an example, DNA can be administered in a solution containing one of the following cationic liposome formulations: Lipofectin™ (LTI/IBRL), Transfast™ (Promega Corp), Tfx50™ (Promega Qorp), Tfx10™ (Promega Corp), or Tfx20™ (Promega Corp).

"Therapeutically effective amounts" of the immune modulatory nucleic acids are administered in accord with the teaching of this invention and will be sufficient to treat or prevent the disease as for example by ameliorating or eliminating symptoms and/or the cause of the disease. For example, therapeutically effective amounts fall within broad range(s) and are determined through clinical trials and for a particular patient is determined based upon factors known to the ordinarily skilled clinician including the severity of the disease, weight of the patient, age and other factors. Therapeutically effective amounts of immune modulatory nucleic acids are in the range of about 0.001 micrograms to about 1 gram. A preferred therapeutic amount of immune modulatory nucleic acid is in the range of about 5 micrograms to about 1000 micrograms of each. A most preferred therapeutic amount of an immune modulatory nucleic acid is in the range of about 50 to 200 micrograms. Immune modulatory nucleic acid therapy is delivered daily, every-other-day, twice-per-week, weekly, every-two-weeks or monthly on an ongoing basis. If delivered in conjunction with polynucleotide therapies encoding self-proteins, -polypeptides, or -peptides then the therapeutic regimen may be administered for various periods such as 6-12 months, and then every 3-12 months as a maintenance dose. Alternative treatment regimens maybe developed depending upon the severity of the disease, the age of the patient, the oligonucleotide and/or polynucleotide encoding self-protein(s), -polypeptide(s) or -peptide(s) being administered and such other factors as would be considered by the ordinary treating physician.

In one embodiment the immune modulatory nucleic acids are delivered by intramuscular injection. In another embodiment the immune modulatory nucleic acids are delivered intranasally, orally, subcutaneously, intradermally, intravenously, impressed through the skin, intraocularly, intraarticularly, intravaginally, intrarectally, mucosally, or attached to gold particles delivered to or through the dermis (see, e.g., WO 97/46253). Alternatively, nucleic acid can be delivered into skin cells by topical application with or without liposomes or charged lipids (see, e.g., U.S. Pat. No. 6,087,341). Yet another alternative is to deliver the nucleic acid as an inhaled agent. In the case of combination therapy comprising the administration of immune modulatory nucleic acids and polynucleotides encoding a self-protein(s), -polypeptide(s), or -peptide(s), the immune modulatory nucleic acid and the polynucleotide can be administered at the same site, or at different sites, as well as at the same time, or at different times.

Prior to delivery of immune modulatory nucleic acids, the delivery site can be preconditioned by treatment with bupivicane, cardiotoxin or another agent that may enhance the delivery of subsequent polynucleotide therapy. Such preconditioning regimens are generally delivered 12 to 96 hours prior to delivery of therapeutic polynucleotide, more frequently 24 to 48 hours prior to delivery of the therapeutic immune modulatory nucleic acids. Alternatively, no preconditioning treatment is given prior to IMS therapy.

The immune modulatory nucleic acids and/or self-vector comprising a polynucleotide encoding the self-protein(s), -polypeptide(s), or -peptide(s) can be administered in combination with other substances, such as pharmacological agents, adjuvants, cytokines, self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), glycoprotein(s), DNA-based therapies, or in conjunction with delivery of vectors encoding cytokines.

In another embodiment the immune modulatory nucleic acids are administered in combination with other therapies. Such therapies could include, for example, immune modulatory nucleic acids administered in combination with self-molecules including, but not limited to, DNA encoding self molecules, for example in the case of polynucleotide therapy (see U.S. patent application Publication 20030148983), or with self-lipids, self-protein(s), self-peptide(s), self-polypeptide(s), self-glycolipid(s), self-carbohydrate(s), self-glycoprotein(s), and posttranslationally-modified self-protein(s), peptide(s), polypeptide(s), or glycoprotein(s), or any other therapeutic compound used to treat autoimmune disease.

A further understanding of the present invention will be obtained by reference to the following description that sets forth illustrative embodiments.

EXAMPLE 1

Confirmation of Prior Studies Showing that IMS Inhibits ISS-Induced Lymphocyte Activation and Prevents Induction of Experimental Autoimmune Encephalomyelitis A series of experiments was carried out confirming various prior studies indicating that an IMS can inhibit stimulation by sequences containing ISS (CpG). Those experiments are as follows.

Figure 1:
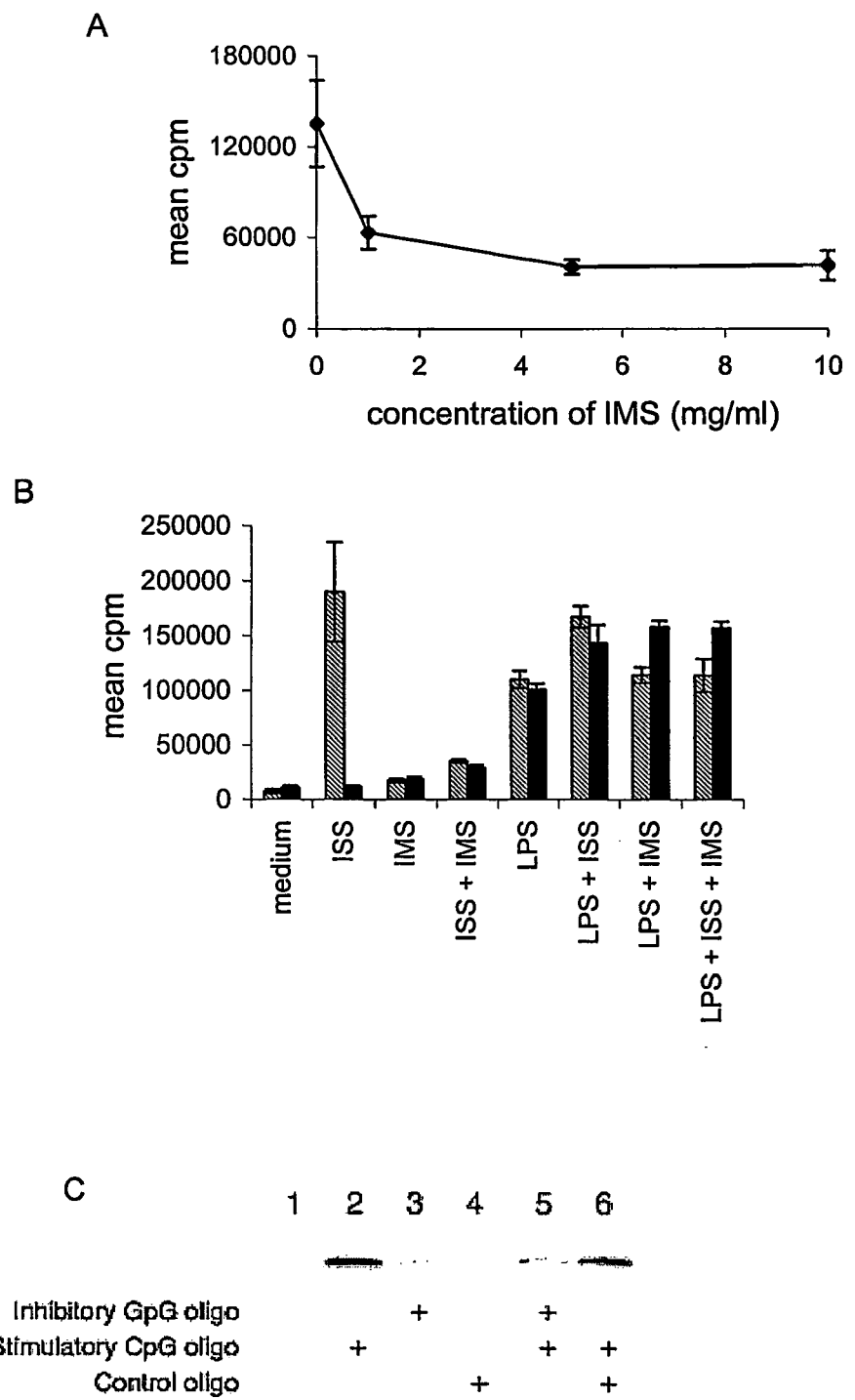
FIG. 1: IMS (inhibitory IMS) suppresses whole splenocyte proliferation mediated by ISS (CpG-ODN) and is dependent on TLR-9. (A) Whole splenocytes were cultured with stimulatory CpG-ODN and increasing concentrations of inhibitory IMS as indicated for 72 h. Wells were pulsed with 1 μCi[$^3$H] TDR for the final 16 h of culture before incorporated radioactivity was measured. Each data point represents the mean of triplicate wells+/−SD. (B) Whole splenocytes from TLR-9 WT (cross-hatched bars) and TLR-9 KO (black bars) mice were isolated and cultured with stimulatory CpG-ODN, inhibitory IMS, or LPS for 72 h. Wells were pulsed with 1 μCi[$^3$H]TDR for the final 16 h of culture before incorporated radioactivity was measured. Each data point represents the mean of triplicate wells+/−SD. (C) IMS inhibits phosphorylation of IκB-α at Serine 32. Naïve splenocytes were cultured in the presence of the indicated oligo at 5 μg/ml for 72 h. The phosphorylation of IκB-α at Serine 32 was determined by Western blot analysis of 20 μg of each protein extract. IκB-α is activated in the presence of stimulatory CpG (lane 2) or stimulatory CpG and control oligo (lane 6), but becomes reduced in activation with the addition of the IMS to the stimulatory CpG oligo (lane 5).

Stimulatory CpG-ODN is known to activate immune cells derived from spleens including dendritic cells, macrophages, T cells, and B cells (see, Krieg et. al., Nature, 374:546-549, 1995; Yi et. al., J. Immunol., 157:5394-5402, 1996; Klinman et. al., Proc Nat. Acad. Sci. USA, 93:2879-2883, 1996; Martin-Orozco et. al., Int. Immunol., 11:1111-1118, 1999; Sparwasser et. al., Eur. J. Immunol., 28-2045-2054, 1998). The effects of IMS were assessed by measuring overall proliferation of naïve splenocytes. We constructed a 22-mer oligonucleotide sequence containing a single 5'-AACGTT-3' (CpG-ODN) (SEQ ID NO:49) or an IMS 5'-AAGGTT-3' (SEQ ID NO:50) sequence with a phosphorothioate backbone to protect the DNA from nuclease degradation. To determine whether the addition of the IMS would counteract the effects of stimulatory CpG-ODN, isolated naïve whole splenocytes were cultured with 5 μg/ml stimulatory CpG-ODN alone and with increasing concentrations of IMS. After 48 hrs whole splenocyte proliferation decreased 2-fold upon the addition of 1 μg/ml IMS, and decreased 3-fold with the addition of 5 μg/ml and 10 μg/ml of IMS (FIG. 1A).

TLR-9 has been shown to recognize bacterial DNA CpG motifs (Hemmi et. al., Nature, 408:740-745, 2000). To determine whether a simple C to G base pair switch would alter this recognition, isolated naïve whole splenocytes from TLR-9 wildtype (WT) and TRL-9 knockout (KO) mice were separately cultured with CpG-ODN, IMS and combinations of both. As a separate control, lipopolysaccharide (LPS) was added to show that the TLR-9 KO splenocytes were still capable of proliferating to a nonspecific mitogenic stimulus. The addition of stimulatory CpG-ODN resulted in a strong proliferative response that was significantly suppressed by the addition of IMS (FIG. 1B). The combination of LPS with stimulatory CpG-ODN increased splenocyte proliferation as compared to LPS stimulation alone. However, the modulatory effects of the IMS were still evident even with the addition of LPS.

The absence of TLR-9 receptor from the TLR-9 KO splenocytes abrogated the proliferative effects of CpG-ODN as compared to TLR-9 WT splenocytes. Similarly, the TLR-9 KO splenocytes did not respond to the IMS. Upon the addition of LPS to the TLR-9 KO splenocytes, the IMS alone and in combination with stimulatory CpG-ODN did not influence the proliferative response when compared to TLR-9 WT splenocytes. This implies that IMS may be preventing stimulatory CpG-ODN from proceeding through the TLR-9 signaling pathway.

The recognition of stimulatory CpG-ODN by TLR-9 triggers the induction of cell signaling pathways culminating in NF-κB activation (Krieg, Ann. Rev. Immunol., 20:709-760, 2002). To elucidate the mechanism of IMS on stimulatory CpG-ODN, the role of NF-κB activity through the phosphorylation of IκB-α at Serine 32 was investigated. Western blot analysis of extracts from splenocytes activated with the indicated oligo confirms the phosphorylation of IκB-α at Serine 32 by stimulatory CpG-ODN (FIG. 1C, lane 2). Accordingly, IMS did not induce phosphorylation of IκB-α at Serine 32 (FIG. 1C, lane 3). Interestingly, the combination of stimulatory CpG-ODN and IMS resulted in a marked reduction in phosphorylation of IκB-α at Serine 32 (FIG. 1C, lane 5). This result indicates that one mechanism by which IMS's function is to compete with stimulatory CpG-ODN for recognition and binding by elements of the TLR-9 signaling pathway.

Figure 2:
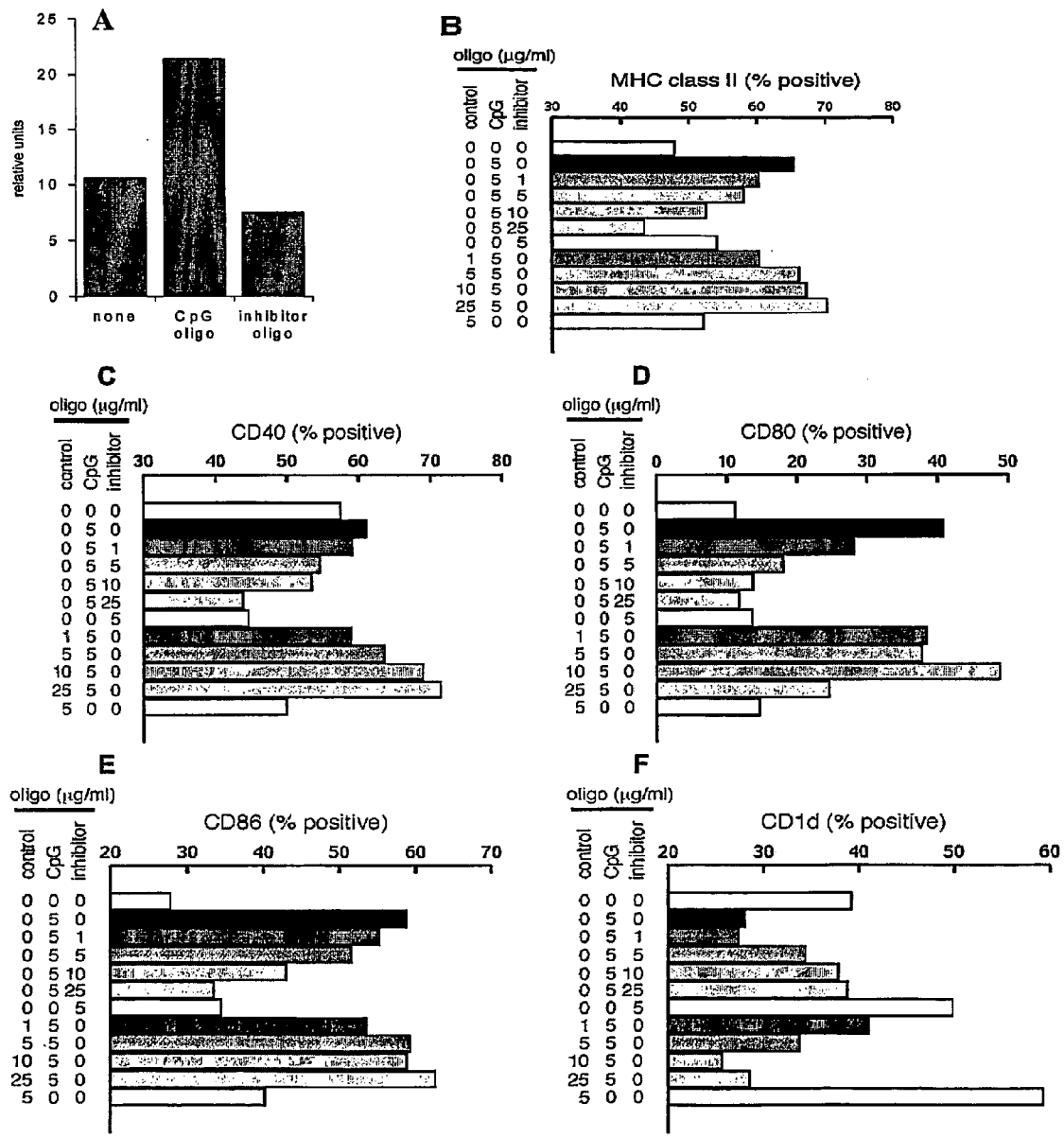
FIG. 2: Inhibitory IMS reduces cell surface MHC class II and costimulatory molecule expression. (A) Naïve splenocytes were cultured in the absence or presence of either stimulatory CpG-ODN (5 μg/ml) or inhibitory IMS (5 μg/ml). Cells were harvested after 72 h. cDNA was synthesized from purified RNA for quantitative PCR analysis. The quantity of RNA for MHC class II is indicated as the relative units compared to quantity of β-actin present in each sample. (B) Naïve splenocytes were cultured in the presence of the indicated amount of each oligonucleotide (in μg/ml). The percentage of cells positive for MHC class II expression was analyzed by FACS, and as shown there is a dose-dependent inhibition of the expression of MHC class II with increasing concentrations of the inhibitor oligonucleotide. (C to F) Effect of inhibitory IMS (inhibitor oligo) on expression of APC activation markers. Naïve splenocytes were cultured with the indicated concentrations of stimulatory CpG-ODN, inhibitory IMS, or control ODN. Cells were harvested after 72 h. FACScan analysis was used to assess expression of CD40 (C), CD80 (D), CD86 (E), and CD1d (F). There is a dose-dependent reduction in expression of CD40, CD80, and CD86, but a dose-dependent increase in expression of CD1d with the inhibitory IMS.

CpG-ODNs have been shown to increase MHC class II expression (Martin-Orozco et. al., Int. Immunol., 11:1111-1118, 1999). To quantitate the relative concentration of message for the MHC class II molecule, quantitative PCR (QPCR) analysis was performed on cDNA from purified RNA samples of whole splenocyte cultures. Signals were normalized relative to the quantity of message for β-actin. MHC class II mRNA was increased in stimulatory splenocytes incubated with the CpG-ODN, but not in splenocytes incubated with IMS (FIG. 2A). The down-regulation of MHC class II cell surface expression by IMS was confirmed by fluorescence activated cell scan (FACScan) analysis. The IMS suppressed the activation of MHC class II cell surface expression by the stimulatory CpG-ODN in a dose dependent manner (FIG. 2B).

To determine if IMS reduced antigen presenting cell (APC) activation, cell surface expression of various APC activation markers was also analyzed. Naïve splenocytes were incubated for 72 hours with the indicated concentrations of inhibitory, stimulatory, or irrelevant control oligonucleotide. FACScan analysis indicates that the IMS suppressed stimulatory CpG-ODN induced cell surface expression of CD40 (FIG. 2C), CD80 (FIG. 2D) and CD86 (FIG. 2E) in a dose dependent manner. In contrast, the expression of the glycolipid presentation molecule, CD1d (FIG. 2F), was increased by the IMS in a dose dependent manner.

Figure 3:
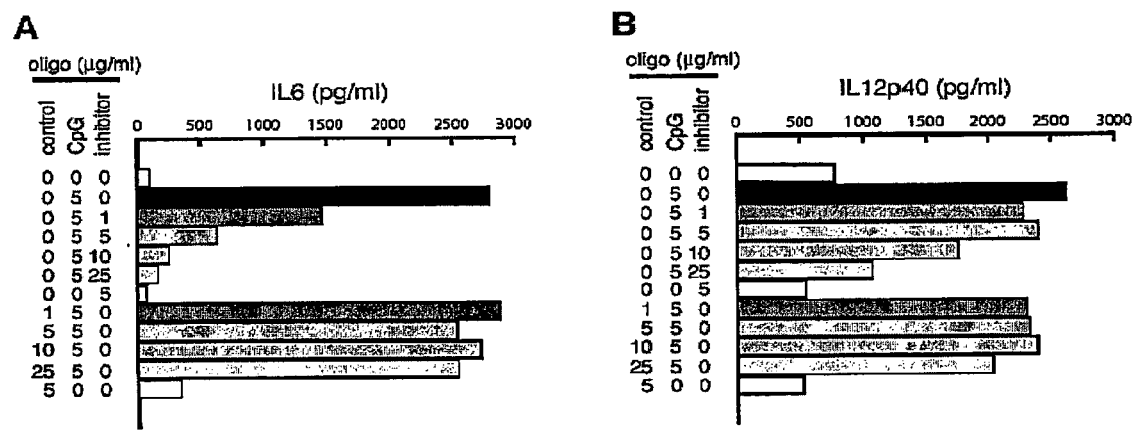
FIG. 3: Inhibitory IMS suppresses Th1 cytokine production. Naïve splenocytes were cultured with the indicated concentrations of stimulatory CpG-ODN, inhibitory IMS, or control ODN. Supernatant were harvested after 72 h. IL6 (A)

In order to profile the effect on cytokine production of immune cells by the immune modulatory oligonucleotide, naïve splenocytes were removed from animals and incubated for 72 hours with the indicated concentrations of IMS, stimulatory CpG-ODN, or irrelevant control oligonucleotide. The IMS alone did not induce the production of IL6 (FIG. 3A) and IL12p40 (FIG. 3B), but when combined with stimulatory CpG-ODN, suppressed cytokine production in a dose dependent manner.

Experimental autoimmune encephalomyelitis (EAE) is a Th1-mediated animal disease model of multiple sclerosis. The central nervous system inflammation induced in EAE disease results in an ascending paralysis as a result of white matter inflammatory infiltration and demyelination. Active induction of EAE requires immunization of the animal with myelin antigen or peptide in complete Freund's adjuvant, which contains heat-killed mycobacteria.

We then investigated the in vivo administration of IMS as a method of prevention of EAE induction. SJL/J mice were immunized subcutaneously for disease induction with $PLP_{139-151}$ peptide in CFA. Concurrently, the indicated oligonucleotide resuspended in phosphate buffered saline was administered intraperitoneally as a single injection. Mice treated with just a single injection of inhibitory IMS exhibited an overall decreased disease severity as compared to PBS-treated and stimulatory CpG-ODN treated mice (FIG. 4).

EXAMPLE 2

IMS Modulate Protective Th2 Cells, Suppress Autoreactive Th1 Cells, and Prevent Induction of Experimental Autoimmune Encephalomyelitis in the Absence of ISS (CpG)

Having demonstrated that IMS suppressed naïve uncommitted myelin-specific T cells, we tested whether it might have differential effects on committed Th1 or Th2 cells in the absence and presence of CpG-ODN. Stimulatory CpG-ODN increased the proliferation of a $PLP_{139-151}$ specific Th1 cell line, whereas the IMS suppressed its proliferation (FIG. 5A). The combination of IMS and stimulatory CpG-ODN decreased the augmentation of the $PLP_{139-151}$ specific Th1 cell proliferation caused by CpG-ODN alone.

Similar investigations were undertaken with a $PLP_{139-151}$ specific Th2 cell line. Stimulatory CpG-ODN suppressed the proliferation of the $PLP_{139-151}$ specific Th2 cell line (FIG. 5B). Surprisingly, the IMS enhanced the proliferation of the Th2 cell line. Thus the CpG-ODN acts as an inhibitor of the $PLP_{139-151}$ specific Th2 cells, whereas the IMS alone, i.e. in the absence of ISS, modulates the $PLP_{139-151}$ specific Th2 cells. Taken together, these unexpected and surprising results establish that the IMS of this invention inhibits autoimmune Th1 cells and augments the protective function of Th2 cells, independent of ISS-ODN (CpG).

IMS were administered to SJL mice 14 and 7 days prior to induction of EAE with $PLP_{139-151}$ in CFA. This protocol introduces the IMS to the immune system for two weeks in the absence of any added ISS's. Mice treated with IMS had a delay in disease onset and an overall decreased disease severity as compared to untreated mice (FIG. 6).

EXAMPLE 3

Polynucleotide Therapy with a GpG Modified Plasmid Vector Backbone

Based on the results with the IMS oligonucleotide demonstrating the benefit of the GpG sequences in reducing disease severity and in producing a Th2 shift in the autoreactive T cell population, we have created a modified vector incorporating GpG sequences within the vector backbone. We began with the pVAX1 vector (Invitrogen, Carlsbad, Calif.) which is the plasmid vector predominantly used in our EAE experiments, and which has been designed to meet all of the regulatory requirements for use in humans. We then examined the vector for CpG motifs that match the known human CpG motif consensus for immune stimulation, that is Pu-Py-C-G-Py-Py. We determined that on one strand of pVAX1, there are 16 such CpG elements. Using site-directed mutagenesis we modified 12 of those sites as summarized on Table 1. The remaining CpG sites occurred within important control regions of the vector and, therefore, were not modified. Where possible the C in the CpG motif was changed to a G to match the sequence motif of the GpG oligo sequences used in the IMS oligonucleotide. This was done at four of the 12 modified sites. The other eight sites were modified not to a GpG but in such a way that the C within the CpG motif was changed to either an A or a T. In this way, the potentially Th1 driving immunostimulatory CpG motif was removed. The vector thus constructed has been named pBHT1, deposited with American Type Culture Collection (ATCC®), 10801 University Boulevard, Manassas, Va. 20110-2209 USA, under ATCC Deposit No. PTA-10152, on Jun. 26, 2009.

TABLE 2

Sequence confirmed sites of mutagenesis and types of nucleotide changes in pBHT1

| Sites* | 784 | 1161 | 1218 | 1264 | 1337 | 1829 | 1874 | 1940 | 1963 | 1966 | 1987 | 1997 |
|---|---|---|---|---|---|---|---|---|---|---|---|---|
| Non-coding | yes | yes | yes | no | no | no | no | no | no | no | no | no |
| Coding | no | no | no | Kan | Kan | Kan | Kan | Kan | Kan | Kan | Kan | Kan |
| C to G | yes | yes | yes | no | no | no | no | no | no | yes | no | no |
| C to A | no | no | no | yes | yes | no | no | no | no | no | no | no |
| C to T | no | no | no | no | no | no | no | no | yes | no | yes | no |
| CGC to AGG | no | no | no | no | no | yes | yes | yes | no | no | no | yes |

*Numbering system is based on the original numbering system of Invitrogen's pVAX1 sequence The pBHT1 vector was tested by in vitro assays to determine if there is in fact a reduced degree of immunostimulation compared to the unmodified pVAX1. Assays were performed using whole fresh splenocytes from SJL/J mice as a source of immune cells. Whole splenocytes were used because stimulatory CpG oligonucleotides are known to activate immune cells derived from spleens including dendritic cells, macrophages, T cells, and B cells. Assays performed included proliferation assay, FACS analysis, and ELISA's for cytokine production. CpG oligonucleotides were used as a control for immune activation and GpG IMS oligonucleotides were used as control for immune inhibition.

In the control assays, proliferation was performed by incubating isolated splenocytes with 10 µg/ml of either CpG oligo or GpG IMS oligo for 24 hours. In addition splenocytes were incubated for 24 hours with three different concentrations of pVAX1 empty vector or pBHT1 empty vector as in FIG. 7. As shown by the stimulation indices, the pVAX1 vector had a higher degree of proliferation compared to pBHT1 vector at each of the vector concentrations. Although the magnitude of stimulation is less (likely because the molar quantity of stimulatory sequences are higher in a given concentration of oligo than in plasmid), the resulting trend in stimulation correlated with that observed with the two oligos. That is, that there is less stimulation with the GpG IMS oligo, and there is also less stimulation with the pBHT1 vector.

Figure 8A:
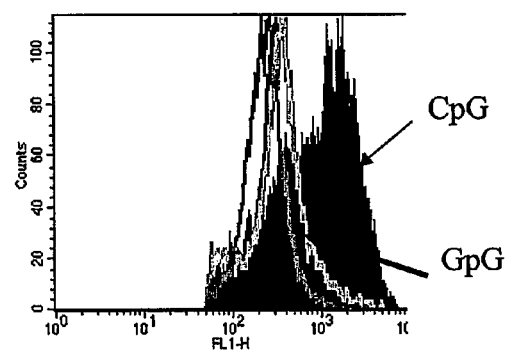
Figure 8B:
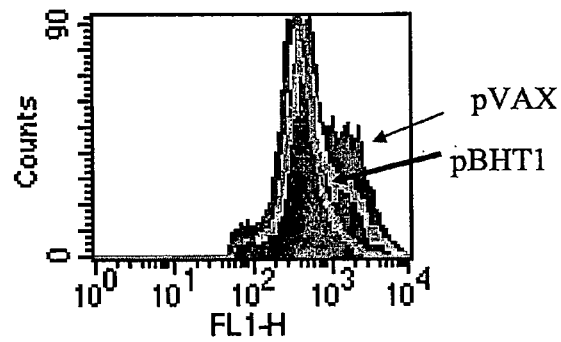

To determine if GpG IMS oligonucleotide reduced antigen presenting cell (APC) activation, cell surface expression of CD16/32 as a marker for activation of APC's was analyzed. Naïve splenocytes were incubated for 48 hours with 10 µg/ml of either CpG oligo or GpG IMS oligos. Cells were harvested and measured by FACScan analysis for CD16/32 expression. Whereas CpG oligos cause the activation of CD16/32, the immunomodulatory GpG IMS oligo suppressed the cell surface expression of CD16/32 to the level almost of that of media alone (FIG. 8A). We then determined if the modified pBHT1 vector behaved in a similar manner in terms of CD16/32 activation. Splenocytes were incubated for 48 hours with 100 µg/ml of either pVAX1 empty vector or pBHT1 empty vector. Again there was a reduction in the activation of CD16/32 with the pBHT1 vector, indicated by a reduction in activation of APC's (FIG. 8B).

CpG oligonucleotides are known to cause the activation of immune cells in such a manner that the secretion of multiple cytokines are increased. We performed assays as above in which splenocytes were incubated with CpG oligo or GpG IMS oligo for the indicate time and the secretion of various cytokines were measured by sandwich ELISA. In addition splenocytes were incubated with pVAX1 and pBHT1 empty vector to determine if the modifications in pBHT1 had a similar effect on cytokine production. As shown in FIG. 9, CpG oligo causes the induction of secretion of IL6, IL10 and IFN-γ from naïve splecnocytes. GpG IMS oligo, however, does not induce the production of any of these cytokines. When the cytokine production induced by pVAX1 vector is compared to that by pBHT1 vector, there is a similar trend in reduced production of IL6, IL10, and IFN-γ with pBHT1. Although there remains a small increased induction of cytokine production by pBHT1 in contrast to GpG IMS in which there was nearly no cytokine induction, the degree of induction is much less than that with pVAX1. This low degree of induction is likely due to the CpG sequences which were not able to be modified and remain on the vector backbone. In fact, we would likely not want a completely innocuous vector that caused no immune induction, as such a vector may have no efficacy in causing the immune system to react in a favorable way to the DNA vaccine.

In vivo experiments assessing the efficacy of the tolerizing polynucleotide DNA therapy approach using a self-antigen within the pBHT1 vector have been performed in the EAE model. The DNA encoding the self-antigen, mouse PLP (proteolipid protein), was incorporated within the pBHT1 vector and administered intramuscularly to SJL mice (see FIG. 10). The model used herein is a treatment model rather than a prevention model in that the mice were first induced for EAE with the peptide $PLP_{139-151}$ in CFA (complete Freund's adjuvant), and then several days after the onset of disease (on day 20) were randomized into various treatment groups. Fifty µg of mouse PLP encoded within the pBHT1 vector or fifty µg of an empty pBHT1 vector control were then administered intramuscularly at three different dose frequencies. As shown in FIG. 10, there is a reduction in the EAE mean disease score in all of the treatment groups, most notably at a frequency of every two or every four weeks. Prior studies using self-antigen polynucleotide therapy with a non-pBHT1 vector have demonstrated a reduction in relapse rates in this type of treatment model of EAE. However, those prior studies have not demonstrated a reduction of this parameter of EAE severity (i.e., mean disease score) in a treatment model, as is demonstrated here with the self-antigen polynucleotide therapy in the pBHT1 vector.

Our conclusion is that the current pBHT1 vector is now more optimized for use in the treatment of Th1 mediated autoimmune diseases such as MS. Therefore, human self-antigen genes are cloned in the pBHT1 vector for use as polynucleotide therapy in the human disease.

EXAMPLE 4

Treatment of an Animal Model of Multiple Sclerosis Using IMS In Combination With DNA Encoding Multiple Self-Proteins A DNA polynucleotide therapy composed of full-length cDNAs encoding the four major components of myelin, MBP, MAG, MOG, and PLP treated relapsing disease in the EAE animal model when given after initial disease onset. Moreover, with the addition of DNA encoding IL-4 to the myelin DNA polynucleotide therapy, the efficacy of treatment is further enhanced by a decrease in relapse rate. However, despite the reduction in relapses, the overall disease severity is still comparable to the control group.

Female SJL/J mice were immunized subcutaneously with 100 μg $PLP_{139-151}$ in PBS emulsified in CFA, consisting of IFA and 0.5 mg heat-inactivated *Mycobacterium tuberculosis*. Twelve days post immunization, at the time of disease onset, mice were injected in both quadriceps with a total of 0.1 ml 0.25% Bupivacaine-HCL in PBS. Two days later, selected mice were injected intramuscularly in both quadriceps with a DNA cocktail mixture containing 25 μg each of four separate pTARGET (Promega Corp. Wisconsin) plasmids encoding full-length murine PLP, MAG, MOG, and MBP plus 50 μg pTARGET plasmid encoding full-length murine IL-4 in a total volume of 0.2 ml. DNA injections were given at weekly intervals over the course of six weeks. At the same time as initial DNA vaccination, 50 μg IMS in a volume of 200 μl PBS was administered intraperitoneally alone or with DNA vaccination. IMS was given every other week over the course of six weeks.

Compared to untreated mice and mice treated with DNA polynucleotide therapy plus a plasmid encoding IL-4, mice treated with IMS alone had an overall decreased mean disease severity throughout the entire disease course (FIG. 11). The reduction of overall mean disease severity was significantly more dramatic when mice were treated with DNA cocktail plus IL-4 in combination with IMS (FIG. 11).

Fifty-seven days after EAE disease induction, mice were sacrificed and inguinal and axillary lymph nodes from the mice were extracted and pooled according to the respective groups. Cells were isolated and stimulated with 10 μg/ml in $PLP_{139-151}$ in enriched RPMI media and 10% FCS. Three days after restimulation, supernatants were collected and screened for IFN-γ, IL-4 and IL-10 production by sandwich ELISA. The cytokine profile for untreated mice and mice treated with IMS alone or with DNA polynucleotide therapy plus IL-4 all had a Th1-bias of increased IFN-γ production (FIG. 12). The group treated with DNA polynucleotide therapy plus IL-4 in combination with IMS had a Th2-bias with increased IL-4 and IL-10 production.

Brains and spinal cords from this in vivo experiment were isolated for histological analysis by perfusing the mice with 10% buffered formalin, after which brain and spinal cord will be removed and further fixed in 10% buffered formalin. Paraffin embedded samples were stained with hematoxylin-eosin and Luxol fast blue stains and Bielschowsky impregnation. As summarized in Table 2, the total number of inflammatory foci in the meninges and parenchyma and the number of foci of demyelination were significantly decreased in the IMS treated group compared to the control group. The total number of inflammatory foci in the meninges and parenchyma and the number of foci of demyelination in mice treated with DNA polynucleotide therapy and IL-4 plus CpG were significantly enhanced compared to the control group. There was a decrease in both the total number of inflammatory foci and the number of foci of demyelination in the group treated with DNA polynucleotide therapy and IL4. The number of inflammatory foci and the number of foci of demyelination were further decreased in the group treated with DNA polynucleotide and IL4 plus IMS.

TABLE 3

| | Number of Inflammatory Foci | | | # Foci of |
|---|---|---|---|---|
| | Meninges | Parenchyma | Total | demyelination |
| CONTROL | 76 | 66 | 142 | 50 |
| | 138 | 128 | 266 | 18 |
| | 106 | 89 | 195 | 39 |
| IMS | 62 | 48 | 110 | 22 |
| | 77 | 54 | 131 | 22 |
| DNA Polynucleotide Therapy + IL4 | 109 | 58 | 167 | 47 |
| | 110 | 106 | 216 | 41 |
| | 69 | 61 | 130 | 40 |
| DNA Polynucleotide Therapy IL4 + IMS | 66 | 17 | 83 | 7 |
| | 69 | 33 | 102 | 18 |
| | 90 | 89 | 179 | 42 |
| DNA Polynucleotide Therapy IL4 + CpG | 160 | 213 | 373 | nd |
| | 196 | 122 | 318 | 36 |
| | 126 | 129 | 255 | 55 |

Serum samples collected at day fifty-seven from mice treated in FIG. 11 was analyzed by a novel protein microarray technology that enables large-scale profiling of the specificity of myelin autoantibody responses between disease and control samples. Array analysis was performed, and SAM was used to identify and create a hierarchical cluster analysis to order the antigen features. In FIG. 13, there was a significant increase in meylin autoantibody epitope spreading by treatment with DNA polynucleotide therapy and IL-4 plus CpG compared to control mice and mice treated with IMS alone and DNA polynucleotide therapy and IL-4. Treatment with DNA polynucleotide therapy and IL-4 plus IMS further increased myelin autoantibody epitope spreading.

Figure 14A:
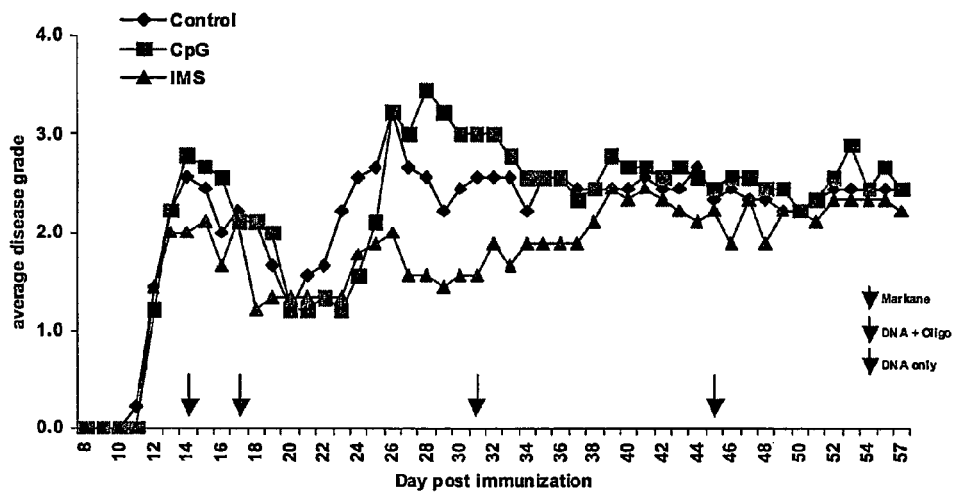
Figure 14B:
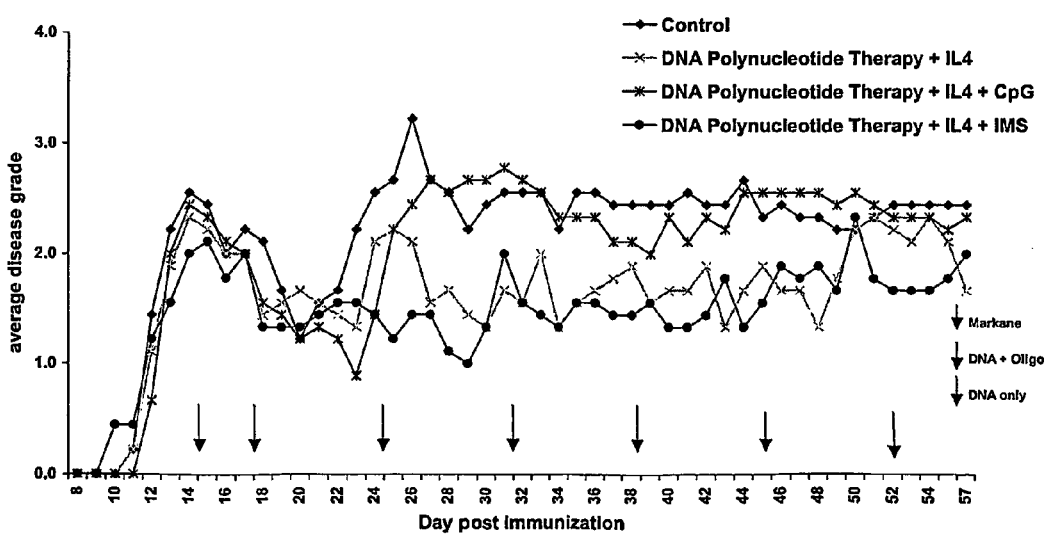

This in vivo experiment was repeated with similar results. In FIG. 14A, at the peak of acute EAE, mice were treated with 50 μg/dose of either IMS or CpG every two weeks. Over the course of fifty-seven days, there was a significant decrease in overall mean disease severity in mice treated with IMS as compared to the PBS-treated mice and mice treated with CpG. In FIG. 14B, at the peak of acute EAE, mice were treated with weekly injections of DNA polynucleotide therapy and IL-4, DNA-polynucleotide therapy and IL-4 plus CpG, or DNA polynucleotide therapy and IL-4 plus IMS. Over the course of fifty-seven days, the overall mean disease severity of mice treated with DNA polynucleotide therapy and IL-4 plus CpG was comparable to PBS-treated mice. There was a significant decrease in overall mean disease severity in mice treated with DNA polynucleotide therapy and IL-4 as compared to PBS-treated mice. Overall mean disease severity was further reduced in mice treated with DNA polynucleotide therapy and IL-4 plus IMS.

EXAMPLE 5

Treatment of Insulin Dependent Diabetes Mellitus Using Ims in Combination with DNA Encoding the Self-Protein Insulin Nonobese diabetic (NOD) mice develop spontaneous autoimmune diabetes, and share many clinical, immunological, and histopathological features with human insulin-dependent diabetes mellitus (IDDM). The disease is characterized by inflammation of the pancreatic islets of Langerhans and destruction of the β cells, leading to hyperglycemia and overt diabetes. Both CD4+ and CD8+ T cells are required for disease development. Reactivity to several autoantigens, including insulin, IA-2, and glutamic acid decarboxylase, have been identified.

The efficacy of IMS treatment in combination with DNA encoding the self-protein insulin was initiated during invasive insulitis but before the complete onset of IDDM. NOD/Lt female mice were obtained at 7 weeks of age and housed in a restricted access room. Mice were tested weekly for elevated blood glucose levels (13GL) beginning at 10 weeks of age using the One Touch Ultra Blood Glucose Monitoring System. Treatment was initiated when the BGL was between 200 to 250 mg/dl. Mice were added sequentially to each group as they became available, beginning at the age of 15 weeks. Mice were injected in both quadriceps with a total of 0.2 ml 0.25% Bupivacaine-HCL in PBS. Two days later, mice were injected intramuscularly in both quadriceps with pVAX1 vector at 50 µg/dose or a DNA cocktail mixture containing 50 µg each of three separate pVAX1 plasmids encoding full-length murine Preproinsulin-1, Preproinsulin-2, and IL-4 in a total volume of 0.2 ml PBS. Injections were given at weekly intervals for four weeks. At the same time as initial DNA vaccination, 50 µg IMS in a volume of 200 µl PBS was administered intraperitoneally alone or with DNA vaccination. IMS was given at weekly intervals for four weeks.

Figure 15A:
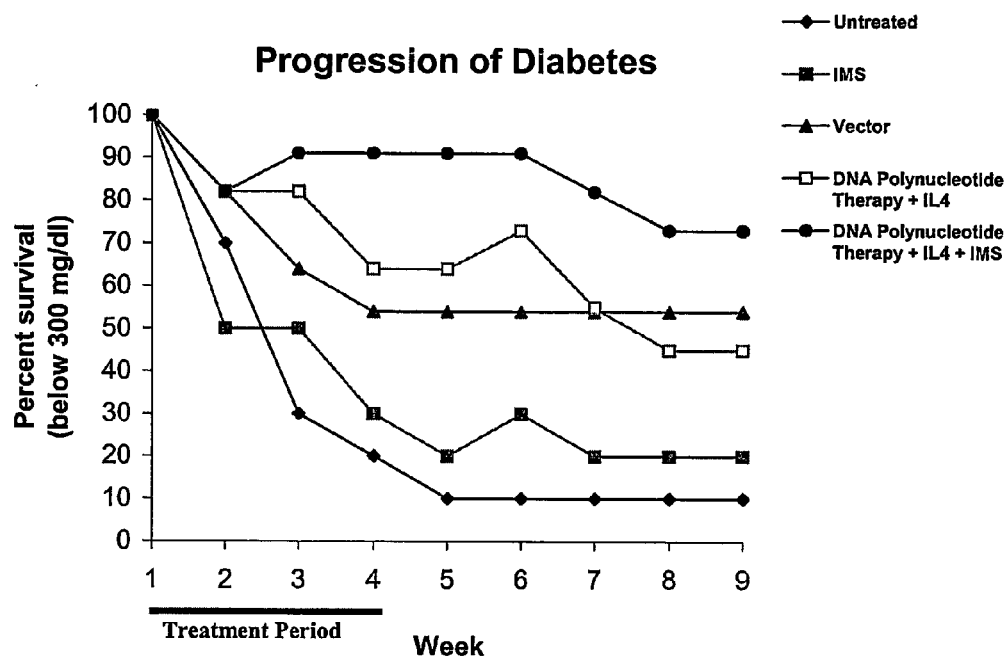
Figure 15B:
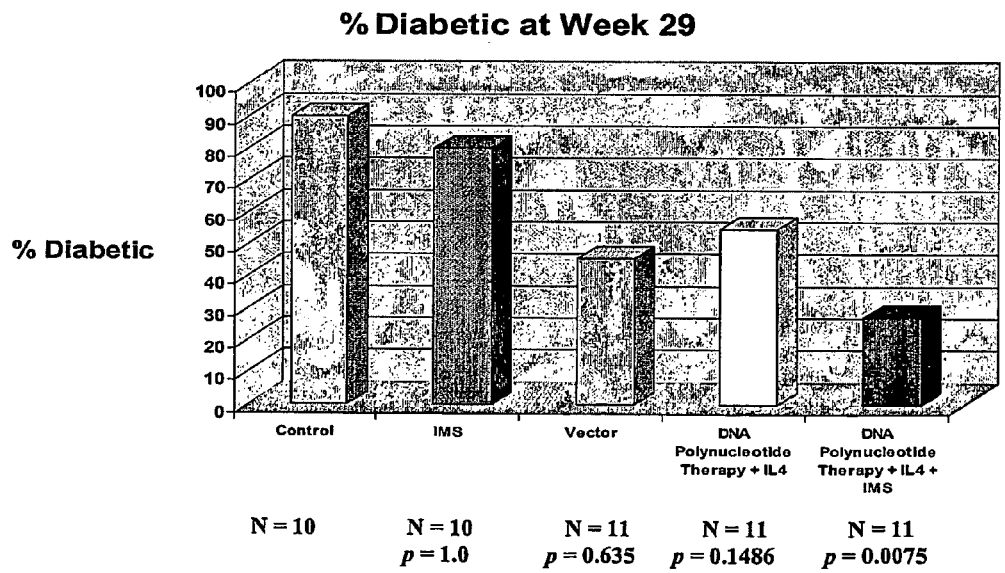

The percent diabetic is defined as mice with a sustained BGL of over 250 mg/dl. After four treatment injections, the survival rate of each group was observed (FIG. 15A). By week 9, the survival rate of the control group was 10%, the IMS alone group was 20%, the plasmid alone group was 54%, the combination of DNA polynucleotide plus IL-4 was 45%, and the combination of DNA polynucleotide plus IL-4 and IMS was 73%. When comparing the age of the mice relative to the respective treatment protocols, mice receiving IMS alone had a diabetes incidence of 80.0% by week 29 (FIG. 15B). Mice receiving empty pVAX1 (Invitrogen, Calif.) plasmid had a diabetes incidence of 45.4%. (p=0.635). Mice treated with a combination of DNA polynucleotide encoding autoantigens and the cytokine IL-4, together with immune modulatory sequences, developed only 27.3% diabetes incidence (p=0.0075) compared with 90% diabetes incidence in the untreated group by week 29 (FIG. 15B). In this experiment, DNA plasmids were injected IM, while IMSs were injected IP, strongly suggesting that DNA plasmids (ISSs) and IMSs were targeting different cell populations. Moreover, NOD mice were not exposed to ISSs in this study. Taken together, this surprising and unexpected result demonstrates that IMSs effectively treat a naturally occurring autoimmune disease.

This study was repeated to include additional treatment groups and the treatment course was modified to weekly intervals for 8 weeks. The treatment groups were 1) PBS treated, 2) empty pVAX1 plasmid at 200 ug/dose, 3) IMS at 50 ug/dose given intramuscularly, 4) the combination of empty pVAX1 plasmid plus IMS (intramuscularly), 5) the combination of DNA polynucleotide, 6) the combination of DNA polynucleotide plus IMS (intramuscularly), 7) the combination of DNA polynucleotide plus IL-4, 8) the combination of DNA polynucleotide plus IL-4 plus IMS (intramuscularly), 9) the comination of DNA polynucleotide plus IL-4 and a separate intraperitoneal injection of IMS. As indicated in FIG. 16, the percent survival of each group was 1) PBS treated (0%), 2) empty pVAX1 plasmid (36%), 3) IMS given intramuscularly (14%), 4) the combination of empty pVAX1 plasmid plus IMS (47%), 5) the combination of DNA polynucleotide (36%), 6) the combination of DNA polynucleotide plus IMS (25%), 7) the combination of DNA polynucleotide plus IL-4 (31%), 8) the combination of DNA polynucleotide plus IL-4 plus IMS (38%), 9) the combination of DNA polynucleotide plus IL-4 and a separate intraperitoneal injection of IMS (54%).

EXAMPLE 6

Treatment of Collagen-Induced Arthritis Using IMS in Combination with DNA Encoding the Self-Protein Whole Type II Collagen and IL4

Murine collagen-induced arthritis (CIA) is an animal model of Rheumatoid arthritis (RA). CIA is induced by injecting genetically susceptible strains of mice with whole type II collagen (CII) emulsified in complete Freund's adjuvant (CFA). CII, the major constituent protein of cartilage in diarthrodial joints, is the predominant site of inflammation in RA (Myers et al., *Life Sciences*, 61:1861-1878, 1997). The resulting severe polyarticular arthritis is characterized by synovitis and the chronic erosion of cartilage and bone that histologically resembles RA (Courtenay et al., *Nature*, 283 (5748):666-668, 1980). Like RA, susceptibility to CIA in rodents is linked to the expression of specific major histocompatibility complex class II molecules (Wooley et al., *J. Exp. Med.*, 154:688-700, 1981; Griffiths, *Int. Rev. Immunol.*, 4:1-15, 1988).

The efficacy of IMS treatment in combination with DNA encoding the self-protein whole type II collagen (CII) and IL-4 was examined. Groups of 20 six-week-old male DBA/1 mice were injected intramuscularly (IM) in both quadriceps with a total of 0.2 ml 0.25% Bupivacaine-HCL in PBS. Two days later, mice were injected intramuscularly in both quadriceps with 50 µg/dose of each of the indicated DNA vaccines and at the same time as initial DNA vaccination, 50 µg IMS in a volume of 200 µl PBS was administered intraperitoneally. The treatment groups were: 1) PBS only, 2) pTarget plasmid and IL-4 in pTarget, 3) pTarget plasmid and IL-4 in pTarget plus IMS, 4) whole CII in pTarget and IL-4 in pTarget; 5) whole CII in pTarget and IL-4 in pTarget plus IMS. Treatment was given 14 and 7 days prior to induction of CIA with CII emulsified in Complete Freund's Adjuvant. Mice received a third DNA tolerizing vaccine dose and/or IMS dose 1 week following induction of CIA. Mice were boosted 2 weeks later with CII emulsified in Incomplete Freund's Adjuvant. Arthritis was scored using the visual scoring system as described in Current Protocols in Immunology.

Figure 17B:
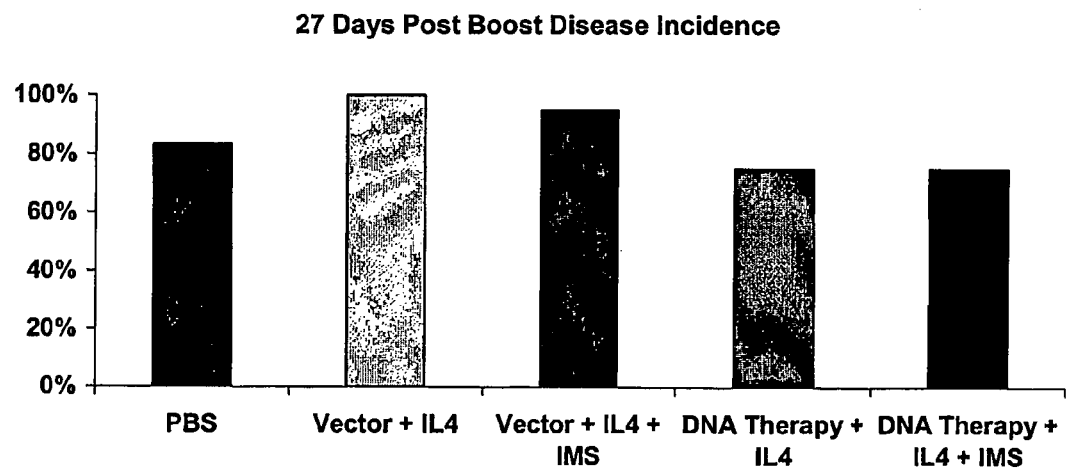

Mice treated with DNA encoding whole type II collagen (CII) plus DNA encoding IL-4, with and without IMS, resulted in significant reductions in the average severity of arthritis as compared to control groups treated with DNA vaccine vector (pTarget)+IL-4 with or without IMS. (FIG. 17A) The overall percent disease incidence was comparable in all groups (FIG. 17B). T cell proliferation to denatured whole CII indicated the presence of CII-reactive T cells in all treatment groups (FIG. 18). Cytokine analysis indicated that treatment with DNA plasmids with and without IMS had significant efficacy in suppressing IL-6 and TNF-alpha production while increasing IL-4 production (FIG. 19).

Figure 20B:
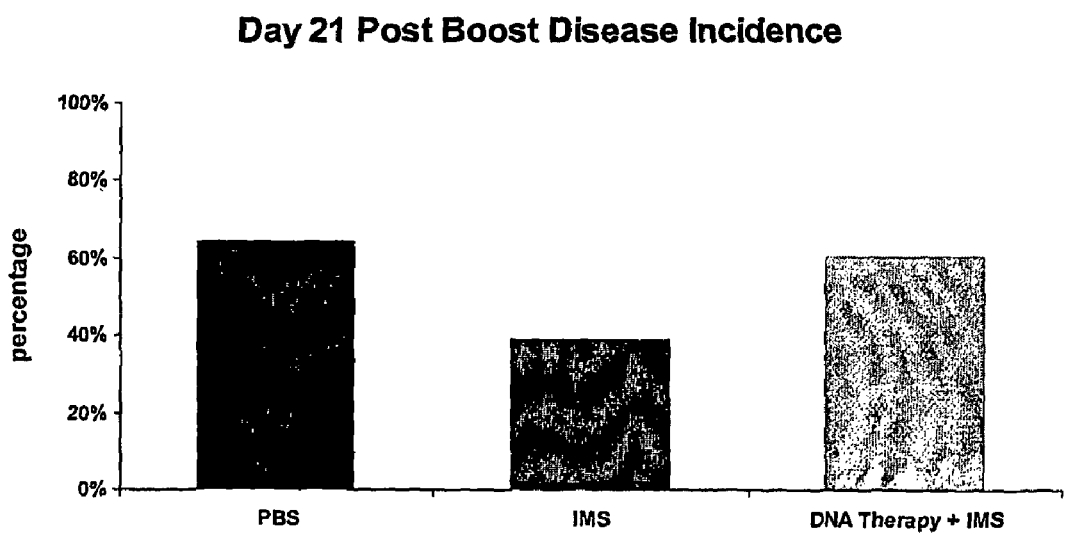

In a second in vivo experiment, the efficacy of IMS treatment alone and in combination with DNA encoding the self-protein whole type II collagen (CII) was examined. Groups of 20 six-week-old male DBA/1 mice were injected intramuscularly (M) in both quadriceps with a total of 0.2 ml 0.25% Bupivacaine-HCL in PBS. Two days later, mice were injected intramuscularly in both quadriceps with 50 µg/dose of each of the indicated DNA vaccines and at the same time as initial DNA vaccination, 50 μg IMS in a volume of 200 μl PBS was administered intraperitoneally. The treatment groups were: 1) PBS only, 2) IMS only, and 3) whole CII in pTarget plus IMS. Treatment was given 14 and 7 days prior to induction of CIA with CII emulsified in Complete Freund's Adjuvant. Mice received a third DNA tolerizing vaccine dose and/or IMS dose 1 week following induction of CIA. Arthritis was scored using the visual scoring system as described in Current Protocols in Immunology. IMS treatment alone resulted in significant reductions in the average severity of arthritis compared to the control group and the group treated with whole CII with IMS (FIG. 20A) as well as reduced disease incidence (FIG. 20B).

EXAMPLE 7

IMS Blocks the Stimulatory Effects of CpGs on Primary B Cells

In primary mature B cells, CpG DNA has been shown to function as a co-stimulatory factor in the presence of a specific antigen by amplifying immunoglobulin production and B cell proliferation(Krieg et al., Nature, 374:546, 1995; Yi et al., J. Immunol., 157:5394, 1996). Primary B cells were isolated from SJL/J spleens by a standard B cell panning technique using a goat anti-mouse IgG and IgM, heavy and light chain specific antibody with goat gamma globulin as a carrier protein, and purity>97% $B220^+$ cells was determined by FACScan analysis. Primary B cells were cultured with 5 ug/ml of indicated oligo for 72 h. LPS was co-cultured at 100 ng/ml. Wells were pulsed with 1 μCi[$^3$H]TDR for the final 16 h of culture before incorporated radioactivity was measured. Each data point represents the mean of triplicate wells+/−SD. As depicted in FIG. 21, an enriched B cell proliferation assay confirmed-that CpGs can cause robust proliferation whereas IMS was able to suppress the effects of CpG-ODN on mature B cells. The co-culture of B cells with LPS and CpG-ODN appeared to have an additive proliferative effect that was suppressed by the addition of IMS but not the control oligo. Cytokine analysis indicated that increased production of IL-6 (FIG. 22A), IFN-gamma (FIG. 22B), IL-10 (FIG. 22C), and IL-12(p40) (FIG. 22D) by CpG-ODN was effectively reduced by the addition of IMS.

EXAMPLE 8

Treatment of Systemic Lupus Erythematosus Using IMS Alone and in Combination with DNA Encoding Self-Proteins to Intracellular Macromolecules There are several murine models of spontaneous and induced lupus-like disease that share many features with human lupus. These include the spontaneous New Zealand hybrid model (NZB/NZW F1 hybrid), the spontaneous MRL-lpr/lpr model, and the pristine induced Balb/c model. The production of autoantibodies directed against intracellular macromolecules such as nucleosomes, DNA, and small nuclear ribonucleoproteins play an important role in the pathogenesis mechanism of tissue injury and glomerulonephritis.

The efficacy of IMS treatment alone and in combination with DNA encoding the self-protein small nuclear ribonucleoproteins U1A or U1C was tested in Balb/c female mice. Groups of 10 six-week-old female Balb/c mice were injected intramuscularly (IM) in both quadriceps with a total of 0.2 ml 0.25% Bupivacaine-HCL in PBS. Two days later, mice were injected intramuscularly in both quadriceps with the indicated DNA vaccines; 1) pTarget plasmid (100 μg/dose); 2) U1A in pTarget plus empty pTarget (each at 50 μg/dose); 3) U1C in pTarget plus empty pTarget (each at 50 μg/dose); and 4) the combination of U1A and U1C (each at 50 μg/dose). At the same time as initial DNA vaccination, 50 μg IMS or CpG in a volume of 200 μl PBS was administered intraperitoneally alone or with DNA vaccination. Injections were administered weekly for two weeks. SLE induction was by a single intraperitoneal injection of 0.5 ml Pristane. Mice then received a third DNA tolerizing vaccine dose and/or oligo dose 1 week following induction of SLE. Monthly injections of the same treatment regimen is to continue for a total of 9 months. The progression of SLE is assessed by monthly monitoring of urine protein levels. At the termination of the experiment, renal tissue damage is assessed by histology staining with hematoxylin and eosin, periodic acid-Schiff, trichrome, and silver-based reticulin stains. Kidney lesions are scored for severity of mesangial hypercellularity, mesangial matrix increase, lobular accentuation, and extent of staining of IgG and C3.

The efficacy of IMS treatment alone and in combination with DNA encoding the self-protein small nuclear ribonucleoprotiens U1A, U1C, and U170, and nucleosomal histones H2B and H3, is tested in MRL-MpJFAS lpr female mice. Groups of 10 six-week-old female MRL-MpJFAS lpr mice are injected intramuscularly (IM) in both quadriceps with a total of 0.2 ml 0.25% Bupivacaine-HCL in PBS. Two days later, mice are injected intramuscularly in both quadriceps with 50 μg/dose of each of the indicated DNA vaccines (pBHT1, U1A in pBHT1, U1C in pBHT1, H2B in pBHT1, and H3 in PBHT1) for 3 consecutive weeks. The vector pBHT1 is described in Example 3. At the same time as initial DNA vaccination, 50 μg/dose of IMS or CpG in a volume of 200 μl PBS is administered intraperitoneally alone or with DNA vaccination. Mice receive two more monthly injections of DNA tolerizing vaccine dose and/or oligo dose. The progression of SLE is assessed by monthly monitoring of urine protein levels. At the termination of the experiment, renal tissue damage is assessed by histology staining with hematoxylin and eosin, periodic acid-Schiff, trichrome, and silver-based reticulin stains. Kidney lesions are scored for severity of mesangial hypercellularity, mesangial matrix increase, lobular accentuation, and extent of staining of IgG and C3.

The efficacy of IMS treatment alone and in combination with DNA encoding the self-protein nucleosomal histones H2B or H3 is tested in (NZB×NZW) F1 hybrid female mice. Groups of 10 five-month-old female (NZB×NZW) F1 hybrid mice are injected intramuscularly (IM) in both quadriceps with a total of 0.2 ml 0.25% Bupivacaine-HCL in PBS. Two days later, mice are injected intramuscularly in both quadriceps with 50 μg/dose of each of the indicated DNA vaccines (pBHT1 plasmid, H2B in pBHT1, H3 in pBHT1, and the combination of H2B and H3) for 3 consecutive weeks. At the same time as initial DNA vaccination, 50 μg/dose of IMS or CpG in a volume of 200 μl PBS is administered intraperitoneally alone or with DNA vaccination. The progression of SLE is assessed by monthly monitoring of urine protein levels. At the termination of the experiment, renal tissue damage is assessed by histology staining with hematoxylin and eosin, periodic acid-Schiff, trichrome, and silver-based reticulin stains. Kidney lesions are scored for severity of mesangial hypercellularity, mesangial matrix increase, lobular accentuation, and extent of staining of IgG and C3.

EXAMPLE 9

Treatment of Primary Biliary Cirrhosis Using IMS Alone and in Combination with DNA Encoding the Self-Protein Pyruvate Dehydrogenase Complex and IL-4

Primary biliary cirrhosis (PBC) is an autoimmune chronic cholestatic liver disease that is CD4+ T cell mediated. Experimental autoimmune cholangitis (EAC) is the animal disease model that produces PBC-like lesions in the biliary epithelial cells lining the small intrahepatic bile ducts in SJL mice sensitized with the self-antigen, pyruvate dehydrogenase complex (PDC).

The efficacy of IMS treatment alone and in combination with DNA encoding the self-proteins dihydrolipoamide acetyl-transferase (E2) and E3-binding protein components of the PDC was tested in SJL/J female mice. Groups of 15 eight-week-old female SJL/J mice were injected intramuscularly (IM) in both quadriceps with a total of 0.2 ml 0.25% Bupivacaine-HCL in PBS. Two days later, mice were injected intramuscularly in both quadriceps with 50 µg/dose of each of the indicated DNA vaccines (pTarget plasmid, PDC-E2 in pTarget, and the combination of PDC-E2 and IL4) with three weekly doses. At the same time as initial DNA vaccination, 50 µg IMS or CpG in a volume of 200 µl PBS was administered intraperitoneally alone or with DNA vaccination. Mice were induced with PDC-E2 peptide GDLLAEIETDKATI (SEQ ID NO:51) (500 µg in 100 µl PBS) emulsified 1:1 (v/v) with CFA (containing 10 mg/ml *Mycobacterium tuberculosis* strain H37RA) with a single 200 µl intraperitoneal injection. EAC is assessed 30 weeks after sensitization. H&E stained liver sections is used for morphologic assessment of necro-inflammation and bile duct injury.

EXAMPLE 10

Screening of Additional IMS Oligonucleotides Predicted to Modulate Autoimmune Disease It is predicted that additional IMS oligonucleotides will have similar or improved efficacy in altering the course of autoimmune disease. The sequence of these additional IMS oligonucleotides are based on the efficacy data obtained with the IMS oligonucleotide described earlier (i.e., 5'TGACTGTGAAGGTTAGAGATGA-3' (SEQ ID NO:52)). Additional IMS oligonucleotides predicted to have similar or improved efficacy follow the following pattern: 5'-TGACTGTGTGRRαβYYAGAGATGA-3' (SEQ ID NO:53), where R represent purines (A or G), Y represent purimidines (C or T), and α and β are either GpG or non-GpG dinucleotides. These oligonucleotides are predicted to have the most robust efficacy in rodent assays as the consensus follows what has been reported to be most active in rodent systems. A complete list of these IMS oligonucleotides are listed in Table 4. In the table, "I" represents inosine.

Similarly, additional IMS oligonucleotides predicted to have similar or improved efficacy follow the following pattern: 5'-TGACTGTGTGRYαβYYAGAGATGA-3' (SEQ ID NO:54) where R represent purines (A or G), Y represent purimidines (C or T), and α and β are either GpG or non-GpG dinucleotides. These oligonucleotides are predicted to have the most robust efficacy in human assays as the consensus follows what has been reported to be most active in human systems. A complete list of these IMS oligonucleotides are listed in Table 5. In the table, "I" represents inosine.

All oligonucleotides are synthesized with a phosphothioate backbone at each and every nucleotide in order to increase the stability of the oligonucleotide. These oligonucleotides are screened individually by in vitro assays for effects on immune cell activation. These screens include cellular proliferation assays, cytokine secretion profiles, and cell surface marker expression analysis by FACS. Candidate IMS oligonucleotides that show inhibitory immune activity are then assayed using in vivo assays for immunomodulation. These in vivo assays include the analysis of immune cells by the above activation parameters after administration of the IMS oligonucleotide to the animal, as well as autoimmune disease models (e.g., EAE, NOD, SLE, and CIA).

In both Table 4 and Table 5, examples of both 5' and 3' flanking sequences around the core hexamer (i.e., RRαβYY or RYαβYY) are depicted. Additional flanking sequences surrounding this core hexamer are created by substituting the flanking sequences with any nucleotide sequence of any length. This is represented in the following sequences: 5'-NNNNNNNNNNRYαβYYNNNNNNNNNN-3' and 5'(SEQ ID NO:55)-NNNNNNNNNN RRαβYYNNNNNNNNNN-3' (SEQ ID NO:56), where N represents any nucleotide. Specific examples include, but are not limited to, the following oligonucleotides:

```
5'-GGGGGGGGGGAAGGTTGGGGGGGGGG-3',    (SEQ ID NO:57),
5'-GGGGGGGGGGATGGTTGGGGGGGGGG-3',    (SEQ ID NO:58),
5'-GGGGGGGGGGACGGTTGGGGGGGGGG-3',    (SEQ ID NO:59),
5'-GGGGGGGGGGAAGCTTGGGGGGGGGG-3',    (SEQ ID NO:60),
5'-GGGGGGGGGGATGCTTGGGGGGGGGG-3',    (SEQ ID NO:61),
5'-GGGGGGGGGGACGCTTGGGGGGGGGG-3',    (SEQ ID NO:62),
5'-CCCCCCCCCCAAGGTTCCCCCGCCCC-3',    (SEQ ID NO:63),
5'-CCCCCCCCGCCATGGTTCCCCCCCCCC-3',   (SEQ ID NO:64),
5'-CCCCCCCCCCACGGTTCCCCCCCCCC-3',    (SEQ ID NO:65),
5'-CCCCCCCCCCAAGCTTCCCCCCCCCC-3',    (SEQ ID NO:66),
5'-CCCCCCCCCCATGCTTCCCCCCCCCC-3',    (SEQ ID NO:67),
5'-CCCCCCCCCCACGCTTCCCCCCCCCC-3'     (SEQ ID NO:68).
```

TABLE 4

| 5' | R | R | α | β | Y | Y | 3' |
|---|---|---|---|---|---|---|---|
| TGACTGTG (SEQ ID NO:69) | A | A | G | C | T | T | AGAGATGA |
| TGACTGTG (SEQ ID NO:70) | A | A | G | C | T | C | AGAGATGA |
| TGACTGTG (SEQ ID NO:71) | A | A | G | C | C | T | AGAGATGA |
| TGACTGTG (SEQ ID NO:72) | A | A | G | C | C | C | AGAGATGA |
| TGACTGTG (SEQ ID NO:73) | A | G | G | C | T | T | AGAGATGA |

TABLE 4-continued

| 5' | R | R | α | β | Y | Y | 3' |
|---|---|---|---|---|---|---|---|
| TGACTGTG (SEQ ID NO:74) | A | G | G | C | T | C | AGAGATGA |
| TGACTGTG (SEQ ID NO:75) | A | G | G | C | C | T | AGAGATGA |
| TGACTGTG (SEQ ID NO:76) | A | C | G | C | C | C | AGAGATGA |
| TGACTGTG (SEQ ID NO:77) | G | A | C | C | T | T | AGAGATGA |
| TGACTGTG (SEQ ID NO:78) | G | A | G | C | T | C | AGAGATGA |
| TGACTGTG (SEQ ID NO:79) | G | A | C | C | C | T | AGAGATGA |
| TGACTGTG (SEQ ID NO:80) | G | A | G | C | C | C | AGAGATGA |
| TGACTGTG (SEQ ID NO:81) | G | G | G | C | T | T | AGAGATGA |
| TGACTGTG (SEQ ID NO:82) | G | C | G | C | T | C | AGAGATGA |
| TGACTGTG (SEQ ID NO:83) | G | G | C | C | C | T | AGAGATGA |
| TGACTGTG (SEQ ID NO:84) | G | G | C | C | C | C | AGAGATGA |
| TGACTGTG (SEQ ID NO:85) | A | A | C | G | T | T | AGAGATGA |
| TGACTGTG (SEQ ID NO:86) | A | A | G | T | T | C | AGAGATGA |
| TGACTGTG (SEQ ID NO:87) | A | A | G | C | C | T | AGAGATGA |
| TGACTGTG (SEQ ID NO:88) | A | A | G | G | C | C | AGAGATGA |
| TGACTGTG (SEQ ID NO:89) | A | G | G | G | T | T | AGAGATGA |
| TGACTGTG (SEQ ID NO:90) | A | C | G | G | T | C | AGAGATGA |
| TGACTGTG (SEQ ID NO:91) | A | C | C | G | C | T | AGAGATGA |
| TGACTGTG (SEQ ID NO:92) | A | G | G | G | C | C | AGAGATGA |
| TGACTGTG (SEQ ID NO:93) | G | A | C | C | T | T | AGAGATGA |
| TGACTGTG (SEQ ID NO:94) | G | A | C | C | T | C | AGAGATGA |
| TGACTGTG (SEQ ID NO:95) | G | A | G | C | C | T | AGAGATGA |
| TGACTGTG (SEQ ID NO:96) | G | A | C | C | C | C | AGAGATGA |
| TGACTGTG (SEQ ID NO:97) | G | G | G | C | T | T | AGAGATGA |
| TGACTGTG (SEQ ID NO:99) | G | G | G | T | T | C | AGAGATGA |
| TGACTGTG (SEQ ID NO:99) | G | C | C | G | C | T | AGAGATGA |
| TGACTGTG (SEQ ID NO:100) | G | C | C | C | C | C | AGAGATGA |
| TGACTGTG (SEQ ID NO:101) | A | A | A | C | T | T | AGAGATGA |
| TGACTGTG (SEQ ID NO:102) | A | A | A | C | T | C | AGAGATGA |
| TGACTGTG (SEQ ID NO:103) | A | A | A | G | C | T | AGAGATGA |
| TGACTGTG (SEQ ID NO:104) | A | A | A | G | C | C | AGAGATGA |
| TGACTGTG (SEQ ID NO:105) | A | G | A | G | T | T | AGAGATGA |
| TGACTGTG (SEQ ID NO:106) | A | G | A | G | T | C | AGAGATGA |
| TGACTGTG (SEQ ID NO:107) | A | G | A | G | C | T | AGAGATGA |
| TGACTGTG (SEQ ID NO:108) | A | G | A | G | C | C | AGAGATGA |
| TGACTGTG (SEQ ID NO:109) | G | A | A | G | T | T | AGAGATGA |
| TGACTGTG (SEQ ID NO:110) | G | A | A | G | T | C | AGAGATGA |
| TGACTGTG (SEQ ID NO:111) | G | A | A | G | C | T | AGAGATGA |

TABLE 4-continued

| 5' | R | R | α | β | Y | Y | 3' |
|---|---|---|---|---|---|---|---|
| TGACTGTG (SEQ ID NO:112) | G | A | A | G | C | C | AGAGATGA |
| TGACTGTG (SEQ ID NO:113) | G | G | A | G | T | T | AGAGATGA |
| TGACTGTG (SEQ ID NO:114) | G | G | A | G | T | C | AGAGATGA |
| TGACTGTG (SEQ ID NO:115) | G | G | A | G | C | T | AGAGATGA |
| TGACTGTG (SEQ ID NO:116) | G | G | A | G | C | C | AGAGATGA |
| TGACTGTG (SEQ ID NO:117) | A | A | I | G | T | T | AGAGATGA |
| TGACTGTG (SEQ ID NO:118) | A | A | I | G | T | C | AGAGATGA |
| TGACTGTG (SEQ ID NO:119) | A | A | I | G | C | T | AGAGATGA |
| TGACTGTG (SEQ ID NO:120) | A | A | I | G | C | C | AGAGATGA |
| TGACTGTG (SEQ ID NO:121) | A | G | I | G | T | T | AGAGATGA |
| TGACTGTG (SEQ ID NO:122) | A | G | I | G | T | C | AGAGATGA |
| TGACTGTG (SEQ ID NO:123) | A | G | I | G | C | T | AGAGATGA |
| TGACTGTG (SEQ ID NO:124) | A | G | I | G | C | C | AGAGATGA |
| TGACTGTG (SEQ ID NO:125) | G | A | I | G | T | T | AGAGATGA |
| TGACTGTG (SEQ ID NO:126) | G | A | I | G | T | C | AGAGATGA |
| TGACTGTG (SEQ ID NO:127) | G | A | I | G | C | T | AGAGATGA |
| TGACTGTG (SEQ ID NO:128) | G | A | I | G | C | C | AGAGATGA |
| TGACTGTG (SEQ ID NO:129) | G | G | I | G | T | T | AGAGATGA |
| TGACTGTG (SEQ ID NO:130) | G | G | I | G | T | C | AGAGATGA |
| TGACTGTG (SEQ ID NO:131) | G | G | I | G | C | T | AGAGATGA |
| TGACTGTG (SEQ ID NO:132) | G | G | I | G | C | C | AGAGATGA |
| TGACTGTG (SEQ ID NO:133) | A | A | I | C | T | T | AGAGATGA |
| TGACTGTG (SEQ ID NO:134) | A | A | I | C | T | C | AGAGATGA |
| TGACTGTG (SEQ ID NO:135) | A | A | I | C | C | T | AGAGATGA |
| TGACTGTG (SEQ ID NO:136) | A | A | I | C | C | C | AGAGATGA |
| TGACTGTG (SEQ ID NO:137) | A | G | I | C | T | T | AGAGATGA |
| TGACTGTG (SEQ ID NO:138) | A | G | I | C | T | C | AGAGATGA |
| TGACTGTG (SEQ ID NO:139) | A | G | I | C | C | T | AGAGATGA |
| TGACTGTG (SEQ ID NO:140) | A | G | I | C | C | C | AGAGATGA |
| TGACTGTG (SEQ ID NO:141) | G | A | I | C | T | T | AGAGATGA |
| TGACTGTG (SEQ ID NO:142) | G | A | I | C | T | C | AGAGATGA |
| TGACTGTG (SEQ ID NO:143) | G | A | I | C | C | T | AGAGATGA |
| TGACTGTG (SEQ ID NO:144) | G | A | I | C | C | C | AGAGATGA |
| TGACTGTG (SEQ ID NO:145) | G | G | I | C | T | T | AGAGATGA |
| TGACTGTG (SEQ ID NO:146) | G | G | I | C | T | C | AGAGAIGA |
| TGACTGTG (SEQ ID NO:147) | G | G | I | C | C | T | AGAGATGA |
| TGACTGTG (SEQ ID NO:148) | G | G | I | C | C | C | AGAGATGA |
| TGACTGTG (SEQ ID NO:149) | A | A | T | G | T | T | AGAGATGA |

TABLE 4-continued

| 5' | R | R | α | β | Y | Y | 3' |
|---|---|---|---|---|---|---|---|
| TGACTGTG (SEQ ID NO:150) | A | A | T | G | T | C | AGAGATGA |
| TGACTGTG (SEQ ID NO:151) | A | A | T | G | C | T | AGAGATGA |
| TGACTGTG (SEQ ID NO:152) | A | A | T | G | C | C | AGAGATGA |
| TGACTGTG (SEQ ID NO:153) | A | G | T | G | T | T | AGAGATGA |
| TGACTGTG (SEQ ID NO:154) | A | G | T | G | T | C | AGAGATGA |
| TGACTGTG (SEQ ID NO:155) | A | G | T | G | C | T | AGAGATGA |
| TGACTGTG (SEQ ID NO:156) | A | G | T | G | C | C | AGAGATGA |
| TGACTGTG (SEQ ID NO:157) | G | A | T | G | T | T | AGAGATGA |
| TGACTGTG (SEQ ID NO:158) | G | A | T | G | T | C | AGAGATGA |
| TGACTGTG (SEQ ID NO:159) | G | A | T | G | C | T | AGAGATGA |
| TGACTGTG (SEQ ID NO:160) | G | A | T | G | C | C | AGAGATGA |
| TGACTGTG (SEQ ID NO:161) | G | G | T | G | T | T | AGAGATGA |
| TGACTGTG (SEQ ID NO:162) | G | G | T | G | T | C | AGAGATGA |
| TGACTGTG (SEQ ID NO:163) | G | G | T | G | C | T | AGAGATGA |
| TGACTGTG (SEQ ID NO:164) | G | G | T | G | C | C | AGAGATGA |
| TGACTGTG (SEQ ID NO:165) | A | A | T | A | T | T | AGAGATGA |
| TGACTGTG (SEQ ID NO:166) | A | A | T | A | T | C | AGAGATGA |
| TGACTGTG (SEQ ID NO:167) | A | A | T | A | C | T | AGAGATGA |
| TGACTGTG (SEQ ID NO:168) | A | A | T | A | C | C | AGAGATGA |
| TGACTGTG (SEQ ID NO:169) | A | G | T | A | T | T | AGAGATGA |
| TGACTGTG (SEQ ID NO:170) | A | G | T | A | T | C | AGAGATGA |
| TGACTGTG (SEQ ID NO:171) | A | G | T | A | C | T | AGAGATGA |
| TGACTGTG (SEQ ID NO:172) | A | G | T | A | C | C | AGAGATGA |
| TGACTGTG (SEQ ID NO:173) | G | A | T | A | T | T | AGAGATGA |
| TGACTGTG (SEQ ID NO:174) | G | A | T | A | T | C | AGAGATGA |
| TGACTGTG (SEQ ID NO:175) | G | A | T | A | C | T | AGAGATGA |
| TGACTGTG (SEQ ID NO:176) | G | A | T | A | C | C | AGAGATGA |
| TGACTGTG (SEQ ID NO:177) | G | G | T | A | T | T | AGAGATGA |
| TGACTGTG (SEQ ID NO:178) | G | G | T | A | T | C | AGAGATGA |
| TGACTGTG (SEQ ID NO:179) | G | G | T | A | C | T | AGAGATGA |
| TGACTGTG (SEQ ID NO:180) | G | G | T | A | C | C | AGAGATGA |
| TGACTGTG (SEQ ID NO:181) | A | A | C | G | T | T | AGAGATGA |
| TGACTGTG (SEQ ID NO:182) | A | A | C | C | T | T | AGAGATGA |

TABLE 5

| 5' | R | Y | α | β | Y | Y | 3' |
|---|---|---|---|---|---|---|---|
| TGACTGTG (SEQ ID NO:183) | A | T | G | C | T | T | AGAGATGA |
| TGACTGTG (SEQ ID NO:184) | A | T | G | C | T | C | AGAGATGA |
| TGACTGTG (SEQ ID NO:185) | A | T | G | C | C | T | AGAGATGA |

TABLE 5-continued

| 5' | R | Y | α | β | Y | Y | 3' |
|---|---|---|---|---|---|---|---|
| TGACTGTG (SEQ ID NO:186) | A | T | G | C | C | C | AGAGATGA |
| TGACTGTG (SEQ ID NO:187) | A | C | G | C | T | T | AGAGATGA |
| TGACTGTG (SEQ ID NO:188) | A | C | G | C | T | C | AGAGATGA |
| TGACTGTG (SEQ ID NO:189) | A | C | G | C | C | T | AGAGATGA |
| TGACTGTG (SEQ ID NO:190) | A | C | G | C | C | C | AGAGATGA |
| TGACTGTG (SEQ ID NO:191) | G | T | G | C | T | T | AGAGATGA |
| TGACTGTG (SEQ ID NO:192) | G | T | G | C | T | C | AGAGATGA |
| TGACTGTG (SEQ ID NO:193) | G | T | G | C | C | T | AGAGATGA |
| TGACTGTG (SEQ ID NO:194) | G | T | G | C | C | C | AGAGATGA |
| TGACTGTG (SEQ ID NO:195) | G | C | G | C | T | T | AGAGATGA |
| TGACTGTG (SEQ ID NO:196) | G | C | G | C | T | C | AGAGATGA |
| TGACTGTG (SEQ ID NO:197) | G | C | G | C | C | T | AGAGATGA |
| TGACTGTG (SEQ ID NO:198) | G | C | G | C | C | C | AGAGATGA |
| TGACTGTG (SEQ ID NO:199) | A | T | G | G | T | T | AGAGATGA |
| TGACTGTG (SEQ ID NO:200) | A | T | G | G | T | C | AGAGATGA |
| TGACTGTG (SEQ ID NO:201) | A | T | G | G | C | T | AGAGATGA |
| TGACTGTG (SEQ ID NO:202) | A | T | G | G | C | C | AGAGATGA |
| TGACTGTG (SEQ ID NO:203) | A | C | G | G | T | T | AGAGATGA |
| TGACTGTG (SEQ ID NO:204) | A | C | G | G | T | C | AGAGATGA |
| TGACTGTG (SEQ ID NO:205) | A | C | G | G | C | T | AGAGATGA |
| TGACTGTG (SEQ ID NO:206) | A | C | G | G | C | C | AGAGATGA |
| TGACTGTG (SEQ ID NO:207) | G | T | G | G | T | T | AGAGATGA |
| TGACTGTG (SEQ ID NO:208) | G | T | G | G | T | C | AGAGATGA |
| TGACTGTG (SEQ ID NO:209) | G | T | G | G | C | T | AGAGATGA |
| TGACTGTG (SEQ ID NO:210) | G | T | G | G | C | C | AGAGATGA |
| TGACTGTG (SEQ ID NO:211) | G | C | G | G | T | T | AGAGATGA |
| TGACTGTG (SEQ ID NO:212) | G | C | G | G | T | C | AGAGATGA |
| TGACTGTG (SEQ ID NO:213) | G | C | G | G | C | T | AGAGATGA |
| TGACTGTG (SEQ ID NO:214) | G | C | G | G | C | C | AGAGATGA |
| TGACTGTG (SEQ ID NO:215) | A | T | A | G | T | T | AGAGATGA |
| TGACTGTG (SEQ ID NO:216) | A | T | A | G | T | C | AGAGATGA |
| TGACTGTG (SEQ ID NO:217) | A | T | A | G | C | T | AGAGATGA |
| TGACTGTG (SEQ ID NO:218) | A | T | A | G | C | C | AGAGATGA |
| TGACTGTG (SEQ ID NO:219) | A | C | A | G | T | T | AGAGATGA |
| TGACTGTG (SEQ ID NO:220) | A | C | A | G | T | C | AGAGATGA |
| TGACTGTG (SEQ ID NO:221) | A | C | A | G | C | T | AGAGATGA |
| TGACTGTG (SEQ ID NO:222) | A | C | A | G | C | C | AGAGATGA |
| TGACTGTG (SEQ ID NO:223) | G | T | A | G | T | T | AGAGATGA |

TABLE 5-continued

| 5' | R | Y | α | β | Y | Y | 3' |
|---|---|---|---|---|---|---|---|
| TGACTGTG (SEQ ID NO:224) | G | T | A | G | T | C | AGAGATGA |
| TGACTGTG (SEQ ID NO:225) | G | T | A | G | C | T | AGAGATGA |
| TGACTGTG (SEQ ID NO:226) | G | T | A | G | C | C | AGAGATGA |
| TGACTGTG (SEQ ID NO:227) | G | C | A | G | T | T | AGAGATGA |
| TGACTGTG (SEQ ID NO:228) | G | C | A | G | T | C | AGAGATGA |
| TGACTGTG (SEQ ID NO:229) | G | C | A | G | C | T | AGAGATGA |
| TGACTGTG (SEQ ID NO:230) | G | C | A | G | C | C | AGAGATGA |
| TGACTGTG (SEQ ID NO:231) | A | T | I | G | T | T | AGAGATGA |
| TGACTGTG (SEQ ID NO:232) | A | T | I | G | T | C | AGAGATGA |
| TGACTGTG (SEQ ID NO:233) | A | T | I | G | C | T | AGAGATGA |
| TGACTGTG (SEQ ID NO:234) | A | T | I | G | C | C | AGAGATGA |
| TGACTGTG (SEQ ID NO:235) | A | C | I | G | T | T | AGAGATGA |
| TGACTGTG (SEQ ID NO:236) | A | C | I | G | T | C | AGAGATGA |
| TGACTGTG (SEQ ID NO:237) | A | C | I | G | C | T | AGAGATGA |
| TGACTGTG (SEQ ID NO:238) | A | C | I | G | C | C | AGAGATGA |
| TGACTGTG (SEQ ID NO:239) | G | T | I | G | T | T | AGAGATGA |
| TGACTGTG (SEQ ID NO:240) | G | T | I | G | T | C | AGAGATGA |
| TGACTGTG (SEQ ID NO:241) | G | T | I | G | C | T | AGAGATGA |
| TGACTGTG (SEQ ID NO:242) | G | T | I | G | C | C | AGAGATGA |
| TGACTGTG (SEQ ID NO:243) | G | C | I | G | T | T | AGAGATGA |
| TGACTGTG (SEQ ID NO:244) | G | C | I | G | T | C | AGAGATGA |
| TGACTGTG (SEQ ID NO:245) | G | C | I | G | C | T | AGAGATGA |
| TGACTGTG (SEQ ID NO:246) | G | C | I | G | C | C | AGAGATGA |
| TGACTGTG (SEQ ID NO:247) | A | T | I | C | T | T | AGAGATGA |
| TGACTGTG (SEQ ID NO:248) | A | T | I | C | T | C | AGAGATGA |
| TGACTGTG (SEQ ID NO:249) | A | T | I | C | C | T | AGAGATGA |
| TGACTGTG (SEQ ID NO:250) | A | T | I | C | C | C | AGAGATGA |
| TGACTGTG (SEQ ID NO:251) | A | C | I | C | T | T | AGAGATGA |
| TGACTGTG (SEQ ID NO:252) | A | C | I | C | T | C | AGAGATGA |
| TGACTGTG (SEQ ID NO:253) | A | C | I | C | C | T | AGAGATGA |
| TGACTGTG (SEQ ID NO:254) | A | C | I | C | C | C | AGAGATGA |
| TGACTGTG (SEQ ID NO:255) | G | T | I | C | T | T | AGAGATGA |
| TGACTGTG (SEQ ID NO:256) | G | T | I | C | T | C | AGAGATGA |
| TGACTGTG (SEQ ID NO:257) | G | T | I | C | C | T | AGAGATGA |
| TGACTGTG (SEQ ID NO:258) | G | T | I | C | C | C | AGAGATGA |
| TGACTGTG (SEQ ID NO:259) | C | C | I | C | T | T | AGAGATGA |
| TGACTGTG (SEQ ID NO:260) | C | C | I | C | T | C | AGAGATGA |
| TGACTGTG (SEQ ID NO:261) | G | C | I | C | C | T | AGAGATGA |

TABLE 5-continued

| 5' | R | Y | α | β | Y | Y | 3' |
|---|---|---|---|---|---|---|---|
| TGACTGTG (SEQ ID NO:262) | G | C | I | C | C | C | AGAGATGA |
| TGACTGTG (SEQ ID NO:263) | A | T | T | C | T | T | AGAGATGA |
| TGACTGTG (SEQ ID NO:264) | A | T | T | C | T | C | AGAGATGA |
| TGACTGTG (SEQ ID NO:265) | A | T | T | C | C | T | AGAGATGA |
| TGACTGTG (SEQ ID NO:266) | A | T | T | G | C | C | AGAGATGA |
| TGACTGTG (SEQ ID NO:267) | A | C | T | G | T | T | AGAGATGA |
| TGACTGTG (SEQ ID NO:268) | A | C | T | G | T | C | AGAGATGA |
| TGACTGTG (SEQ ID NO:269) | A | C | T | C | C | T | AGAGATGA |
| TGACTGTG (SEQ ID NO:270) | A | C | T | C | C | C | AGAGATGA |
| TGACTGTG (SEQ ID NO:271) | C | T | T | G | T | T | AGAGATGA |
| TGACTGTG (SEQ ID NO:272) | C | T | T | C | T | C | AGAGATGA |
| TGACTGTG (SEQ ID NO:273) | C | T | T | C | C | T | AGAGATGA |
| TGACTGTG (SEQ ID NO:274) | C | T | T | C | C | C | AGAGATGA |
| TGACTGTG (SEQ ID NO:275) | C | C | T | C | T | T | AGAGATGA |
| TGACTGTG (SEQ ID NO:276) | C | C | T | C | T | C | AGAGATGA |
| TGACTGTG (SEQ ID NO:277) | C | C | T | C | C | T | AGAGATGA |
| TGACTGTG (SEQ ID NO:278) | C | C | T | C | C | C | AGAGATGA |
| TGACTGTG (SEQ ID NO:279) | A | T | T | A | T | T | AGAGATGA |
| TGACTGTG (SEQ ID NO:280) | A | T | T | A | T | C | AGAGATGA |
| TGACTGTG (SEQ ID NO:281) | A | T | T | A | C | T | AGAGATGA |
| TGACTGTG (SEQ ID NO:282) | A | T | T | A | C | C | AGAGATGA |
| TGACTGTG (SEQ ID NO:283) | A | C | T | A | T | T | AGAGATGA |
| TGACTGTG (SEQ ID NO:284) | A | C | T | A | T | C | AGAGATGA |
| TGACTGTG (SEQ ID NO:285) | A | C | T | A | C | T | AGAGATGA |
| TGACTGTG (SEQ ID NO:286) | A | C | T | A | C | C | AGAGATGA |
| TGACTGTG (SEQ ID NO:287) | C | T | T | A | T | T | AGAGATGA |
| TGACTGTG (SEQ ID NO:288) | C | T | T | A | T | C | AGAGATGA |
| TGACTGTG (SEQ ID NO:289) | C | T | T | A | C | T | AGAGATGA |
| TGACTGTG (SEQ ID NO:290) | C | T | T | A | C | C | AGAGATGA |
| TGACTGTG (SEQ ID NO:291) | C | C | T | A | T | T | AGAGATGA |
| TGACTGTG (SEQ ID NO:292) | C | C | T | A | T | C | AGAGATGA |
| TGACTGTG (SEQ ID NO:293) | C | C | T | A | C | T | AGAGATGA |
| TGACTGTG (SEQ ID NO:294) | C | C | T | A | C | C | AGAGATGA |
| TGACTGTG (SEQ ID NO:295) | A | T | C | C | T | T | AGAGATGA |
| TGACTGTG (SEQ ID NO:296) | A | C | C | C | T | T | AGAGATGA |

The previous examples are specific embodiments for carrying out the present invention. The examples are offered for illustrative purposes only, and are not intended to limit the scope of the present invention in any way. Other variants of the inventions will be readily apparent to those of ordinary skill in the art and encompassed by the appended claims. All publications, patents, patent applications, and other references cited herein are hereby incorporated by reference.

What is claimed is:

1. A pBHT1 vector having a nucleic acid sequence of ATCC Deposit No. PTA-10152.

2. The pBHT1 vector of claim 1, wherein the vector further comprises a polynucleotide encoding a self-protein associated with an autoimmune disease.

3. The pBHT1 vector of claim 2, wherein the autoimmune disease is multiple sclerosis.

4. The pBHT1 vector of claim 3, wherein the self-protein associated with multiple sclerosis is selected from the group consisting of myelin basic protein (MBP), proteolipid protein, myelin associated glycoprotein, cyclic nucleotide phosphodiesterase, myelin-associated glycoprotein, myelin-associated oligodendrocytic basic protein; alpha-B-crystallin and myelin oligodendrocyte glycoprotein.

5. The pBHT1 vector of claim 2, wherein the autoimmune disease is insulin dependent diabetes mellitus (IDDM).

6. The pBHT 1 vector of claim 5, wherein the self-protein associated with insulin dependent diabetes mellitus (IDDM) is selected from the group consisting of tyrosine phosphatase IA2, IA-2β, glutamic acid decarboxylase (65 and 67 kDa forms), carboxypeptidase H, heat shock proteins, glima 38, islet cell antigen 69 KDa, p52, islet cell glucose transporter GLUT-2, insulin, proinsulin and preproinsulin.

7. The pBHT1 vector of claim 4, wherein the self-protein associated with multiple sclerosis is myelin basic protein (MBP).

8. The pBHT1 vector of claim 4, wherein the self-protein associated with insulin dependent diabetes mellitus is proinsulin.

9. A vector comprising nucleic acid sequence of ATCC Deposit No. PTA-10152 and a nucleic acid sequence encoding a self-protein associated with insulin dependent diabetes mellitus.

10. The vector of claim 9 wherein the self-protein associated with insulin dependent diabetes mellitus encoded by the nucleic acid is proinsulin.

11. A pharmaceutical formulation comprising the vector of claim 9 in a pharmaceutically acceptable carrier.

* * * * *

SEQUENCE LISTING

<160> NUMBER OF SEQ ID NOS: 298

<210> SEQ ID NO 1
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 1 gtggtt                                                                     6

<210> SEQ ID NO 2
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 2 atggtt                                                                     6

<210> SEQ ID NO 3
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 3 gcggtt                                                                     6

<210> SEQ ID NO 4
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 4 acggtt                                                                     6

<210> SEQ ID NO 5
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 5 gtggct                                                                     6

<210> SEQ ID NO 6
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 6 atggct                                                            6

<210> SEQ ID NO 7
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 7 gcggct                                                            6

<210> SEQ ID NO 8
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 8 acggct                                                            6

<210> SEQ ID NO 9
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 9 gtggtc                                                            6

<210> SEQ ID NO 10
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 10 atggtc                                                            6

<210> SEQ ID NO 11
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 11 gcggtc                                                            6

<210> SEQ ID NO 12
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 12

-continued acggtc                                                                6

<210> SEQ ID NO 13
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 13 gtgctt                                                                6

<210> SEQ ID NO 14
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 14 atgctt                                                                6

<210> SEQ ID NO 15
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 15 gcgctt                                                                6

<210> SEQ ID NO 16
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 16 acgctt                                                                6

<210> SEQ ID NO 17
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 17 gtgcct                                                                6

<210> SEQ ID NO 18
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 18 atgcct                                                                6

<210> SEQ ID NO 19
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 19 gcgcct                                                                    6

<210> SEQ ID NO 20
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 20 acgcct                                                                    6

<210> SEQ ID NO 21
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 21 gtgctc                                                                    6

<210> SEQ ID NO 22
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 22 atgctc                                                                    6

<210> SEQ ID NO 23
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 23 gcgctc                                                                    6

<210> SEQ ID NO 24
<211> LENGTH: 6
<212> TYPE: DNA
<213> ORGANISM: Artificial Sequence
<220> FEATURE:
<223> OTHER INFORMATION: synthetic immune modulatory sequence (IMS),
      immune modulatory nucleic acid, core hexamer

<400> SEQUENCE: 24 acgctc                                                                    6

```
<210> SEQ ID NO 25
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 25 ggggtt                                                                    6

<210> SEQ ID NO 26
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 26 agggtt                                                                    6

<210> SEQ ID NO 27
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 27 gaggtt                                                                    6

<210> SEQ ID NO 28
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 28 aaggtt                                                                    6

<210> SEQ ID NO 29
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 29 ggggct                                                                    6

<210> SEQ ID NO 30
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 30 agggct                                                                    6
```

```
<210> SEQ ID NO 31
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 31 gaggct                                                                    6

<210> SEQ ID NO 32
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 32 aaggct                                                                    6

<210> SEQ ID NO 33
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 33 ggggtc                                                                    6

<210> SEQ ID NO 34
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 34 agggtc                                                                    6

<210> SEQ ID NO 35
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 35 gaggtc                                                                    6

<210> SEQ ID NO 36
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 36 aaggtc                                                                    6

<210> SEQ ID NO 37
```

```
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 37 gggctt                                                                      6

<210> SEQ ID NO 38
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 38 aggctt                                                                      6

<210> SEQ ID NO 39
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 39 gagctt                                                                      6

<210> SEQ ID NO 40
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 40 aagctt                                                                      6

<210> SEQ ID NO 41
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 41 gggcct                                                                      6

<210> SEQ ID NO 42
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 42 aggcct                                                                      6

<210> SEQ ID NO 43
<211> LENGTH: 6
```

```
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 43 gagcct                                                                      6

<210> SEQ ID NO 44
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 44 aagcct                                                                      6

<210> SEQ ID NO 45
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 45 gggctc                                                                      6

<210> SEQ ID NO 46
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 46 aggctc                                                                      6

<210> SEQ ID NO 47
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 47 gagctc                                                                      6

<210> SEQ ID NO 48
<211> LENGTH: 6
<212> TYPE: DNA
<213> ORGANISM: Artificial Sequence
<220> FEATURE:
<223> OTHER INFORMATION: synthetic immune inhibitory sequence (IIS),
      immune modulatory sequence (IMS), core hexamer

<400> SEQUENCE: 48 aagctc                                                                      6

<210> SEQ ID NO 49
<211> LENGTH: 6
<212> TYPE: DNA
```

```
<213> ORGANISM: Artificial Sequence
<220> FEATURE:
<223> OTHER INFORMATION: synthetic immunostimulatory sequence (ISS),
      stimulatory CpG-ODN oligodeoxynucleotide

<400> SEQUENCE: 49 aacgtt                                                                      6

<210> SEQ ID NO 50
<211> LENGTH: 6
<212> TYPE: DNA
<213> ORGANISM: Artificial Sequence
<220> FEATURE:
<223> OTHER INFORMATION: synthetic immune modulatory sequence (IMS)
<220> FEATURE:
<221> NAME/KEY: misc_feature
<222> LOCATION: (1)..(6)
<223> OTHER INFORMATION: phosphorothioate backbone

<400> SEQUENCE: 50 aaggtt                                                                      6

<210> SEQ ID NO 51
<211> LENGTH: 14
<212> TYPE: PRT
<213> ORGANISM: Artificial Sequence
<220> FEATURE:
<223> OTHER INFORMATION: dihydrolipoamide acetyl-transferase (E2)
      component of pyruvate dehydrogenase complex (PDC), PDC-E2 peptide
      self-antigen

<400> SEQUENCE: 51

Gly Asp Leu Leu Ala Glu Ile Glu Thr Asp Lys Ala Thr Ile
1               5                   10

<210> SEQ ID NO 52
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide

<400> SEQUENCE: 52
tgactgtgaa ggttagagat ga                                                   22

<210> SEQ ID NO 53
<211> LENGTH: 24
<212> TYPE: DNA
<213> ORGANISM: Artificial Sequence
<220> FEATURE:
<223> OTHER INFORMATION: synthetic immune modulatory sequence (IMS)
      oligonucleotide
<220> FEATURE:
<221> NAME/KEY: misc_feature
<222> LOCATION: (13)..(14)
<223> OTHER INFORMATION: nn is GpG or non-GpG dinucleotide

<400> SEQUENCE: 53
tgactgtgtg rrnnyyagag atga                                                 24

<210> SEQ ID NO 54
<211> LENGTH: 24
<212> TYPE: DNA
<213> ORGANISM: Artificial Sequence
<220> FEATURE:
<223> OTHER INFORMATION: synthetic immune modulatory sequence (IMS)
      oligonucleotide
<220> FEATURE:
```

-continued

```
<221> NAME/KEY: misc_feature
<222> LOCATION: (13)..(14)
<223> OTHER INFORMATION: nn is GpG or non-GpG dinucleotide

<400> SEQUENCE: 54
tgactgtgtg rynnyyagag atga                                              24

<210> SEQ ID NO 55
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (1)..(10)
<223> OTHER INFORMATION: n is any nucleotide
<220> FEATURE:
<221> NAME/KEY: misc_feature
<222> LOCATION: (13)..(14)
<223> OTHER INFORMATION: nn is GpG or non-GpG dinucleotide
<220> FEATURE:
<221> NAME/KEY: misc_feature
<222> LOCATION: (17)..(26)
<223> OTHER INFORMATION: n is any nucleotide

<400> SEQUENCE: 55
nnnnnnnnnn rynnyynnnn nnnnnn                                            26

<210> SEQ ID NO 56
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (1)..(10)
<223> OTHER INFORMATION: n is any nucleotide
<220> FEATURE:
<221> NAME/KEY: misc_feature
<222> LOCATION: (13)..(14)
<223> OTHER INFORMATION: nn is GpG or non-GpG dinucleotide
<220> FEATURE:
<221> NAME/KEY: misc_feature
<222> LOCATION: (17)..(26)
<223> OTHER INFORMATION: n is any nucleotide

<400> SEQUENCE: 56
nnnnnnnnnn rrnnyynnnn nnnnnn                                            26

<210> SEQ ID NO 57
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 57
gggggggggg aaggttgggg gggggg                                            26

<210> SEQ ID NO 58
<211> LENGTH: 26
<212> TYPE: DNA
<213> ORGANISM: Artificial Sequence
```

```
<220> FEATURE:
<223> OTHER INFORMATION: synthetic immune modulatory sequence (IMS)
      oligonucleotide with 5' and 3' flanking sequences around core
      hexamer

<400> SEQUENCE: 58
gggggggggg atggttgggg gggggg                                              26

<210> SEQ ID NO 59
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 59
gggggggggg acggttgggg gggggg                                              26

<210> SEQ ID NO 60
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 60
gggggggggg aagcttgggg gggggg                                              26

<210> SEQ ID NO 61
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 61
gggggggggg atgcttgggg gggggg                                              26

<210> SEQ ID NO 62
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 62
gggggggggg acgcttgggg gggggg                                              26

<210> SEQ ID NO 63
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 63
cccccccccc aaggttcccc cccccc                                              26
```

<210> SEQ ID NO 64
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 64 ccccccccc atggttcccc ccccccc                                         26

<210> SEQ ID NO 65
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 65 ccccccccc acggttcccc ccccc                                           26

<210> SEQ ID NO 66
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 66 ccccccccc aagcttcccc ccccc                                           26

<210> SEQ ID NO 67
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 67 ccccccccc atgcttcccc ccccc                                           26

<210> SEQ ID NO 68
<211> LENGTH: 26
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 68 ccccccccc acgcttcccc ccccc                                           26

<210> SEQ ID NO 69
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer -continued

```
<400> SEQUENCE: 69
tgactgtgaa gcttagagat ga                                              22

<210> SEQ ID NO 70
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 70
tgactgtgaa gctcagagat ga                                              22

<210> SEQ ID NO 71
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 71
tgactgtgaa gcctagagat ga                                              22

<210> SEQ ID NO 72
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 72
tgactgtgaa gcccagagat ga                                              22

<210> SEQ ID NO 73
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 73
tgactgtgag gcttagagat ga                                              22

<210> SEQ ID NO 74
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 74
tgactgtgag gctcagagat ga                                              22

<210> SEQ ID NO 75
<211> LENGTH: 22
<212> TYPE: DNA
```

```
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 75
tgactgtgag gcctagagat ga                                              22

<210> SEQ ID NO 76
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 76
tgactgtgag gcccagagat ga                                              22

<210> SEQ ID NO 77
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 77
tgactgtgga gcttagagat ga                                              22

<210> SEQ ID NO 78
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 78
tgactgtgga gctcagagat ga                                              22

<210> SEQ ID NO 79
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 79
tgactgtgga gcctagagat ga                                              22

<210> SEQ ID NO 80
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 80
tgactgtgga gcccagagat ga                                              22
```

```
<210> SEQ ID NO 81
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 81
tgactgtggg gcttagagat ga                                              22

<210> SEQ ID NO 82
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 82
tgactgtggg gctcagagat ga                                              22

<210> SEQ ID NO 83
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 83
tgactgtggg gcctagagat ga                                              22

<210> SEQ ID NO 84
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 84
tgactgtggg gcccagagat ga                                              22

<210> SEQ ID NO 85
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 85
tgactgtgaa ggttagagat ga                                              22

<210> SEQ ID NO 86
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
```

-continued hexamer

<400> SEQUENCE: 86
tgactgtgaa ggtcagagat ga                                              22

<210> SEQ ID NO 87
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 87
tgactgtgaa ggctagagat ga                                              22

<210> SEQ ID NO 88
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 88
tgactgtgaa ggccagagat ga                                              22

<210> SEQ ID NO 89
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 89
tgactgtgag ggttagagat ga                                              22

<210> SEQ ID NO 90
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 90
tgactgtgag ggtcagagat ga                                              22

<210> SEQ ID NO 91
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 91
tgactgtgag ggctagagat ga                                              22

<210> SEQ ID NO 92
<211> LENGTH: 22

```
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 92
tgactgtgag ggccagagat ga                                                    22

<210> SEQ ID NO 93
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 93
tgactgtgga ggttagagat ga                                                    22

<210> SEQ ID NO 94
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 94
tgactgtgga ggtcagagat ga                                                    22

<210> SEQ ID NO 95
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 95
tgactgtgga ggctagagat ga                                                    22

<210> SEQ ID NO 96
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 96
tgactgtgga ggccagagat ga                                                    22

<210> SEQ ID NO 97
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 97
```

-continued tgactgtggg ggttagagat ga					22

<210> SEQ ID NO 98
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 98
tgactgtggg ggtcagagat ga					22

<210> SEQ ID NO 99
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 99
tgactgtggg ggctagagat ga					22

<210> SEQ ID NO 100
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 100
tgactgtggg ggccagagat ga					22

<210> SEQ ID NO 101
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 101
tgactgtgaa agttagagat ga					22

<210> SEQ ID NO 102
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 102
tgactgtgaa agtcagagat ga					22

<210> SEQ ID NO 103
<211> LENGTH: 22
<212> TYPE: DNA
<213> ORGANISM: Artificial Sequence
<220> FEATURE:
<223> OTHER INFORMATION: synthetic immune modulatory sequence (IMS)

-continued oligonucleotide with 5' and 3' flanking sequences around core
hexamer

<400> SEQUENCE: 103
tgactgtgaa agctagagat ga                                                  22

<210> SEQ ID NO 104
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 104
tgactgtgaa agccagagat ga                                                  22

<210> SEQ ID NO 105
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 105
tgactgtgag agttagagat ga                                                  22

<210> SEQ ID NO 106
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 106
tgactgtgag agtcagagat ga                                                  22

<210> SEQ ID NO 107
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 107
tgactgtgag agctagagat ga                                                  22

<210> SEQ ID NO 108
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 108
tgactgtgag agccagagat ga                                                  22

<210> SEQ ID NO 109

```
<210> SEQ ID NO 109
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 109
tgactgtgga agttagagat ga                                              22

<210> SEQ ID NO 110
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 110
tgactgtgga agtcagagat ga                                              22

<210> SEQ ID NO 111
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 111
tgactgtgga agctagagat ga                                              22

<210> SEQ ID NO 112
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 112
tgactgtgga agccagagat ga                                              22

<210> SEQ ID NO 113
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 113
tgactgtggg agttagagat ga                                              22

<210> SEQ ID NO 114
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 114
```
tgactgtggg agtcagagat ga                                                22

<210> SEQ ID NO 115
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 115
tgactgtggg agctagagat ga                                                22

<210> SEQ ID NO 116
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 116
tgactgtggg agccagagat ga                                                22

<210> SEQ ID NO 117
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 117
tgactgtgaa ngttagagat ga                                                22

<210> SEQ ID NO 118
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 118
tgactgtgaa ngtcagagat ga                                                22

<210> SEQ ID NO 119
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)

<223> OTHER INFORMATION: n is i

<400> SEQUENCE: 119
tgactgtgaa ngctagagat ga     22

<210> SEQ ID NO 120
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 120
tgactgtgaa ngccagagat ga     22

<210> SEQ ID NO 121
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 121
tgactgtgag ngttagagat ga     22

<210> SEQ ID NO 122
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 122
tgactgtgag ngtcagagat ga     22

<210> SEQ ID NO 123
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 123
tgactgtgag ngctagagat ga     22

<210> SEQ ID NO 124
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer
<220> FEATURE:
<221> NAME/KEY: misc_feature
<222> LOCATION: (11)..(11)
<223> OTHER INFORMATION: n is i

<400> SEQUENCE: 124
tgactgtgag ngccagagat ga                                              22

<210> SEQ ID NO 125
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer
<220> FEATURE:
<221> NAME/KEY: misc_feature
<222> LOCATION: (11)..(11)
<223> OTHER INFORMATION: n is i

<400> SEQUENCE: 125
tgactgtgga ngttagagat ga                                              22

<210> SEQ ID NO 126
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer
<220> FEATURE:
<221> NAME/KEY: misc_feature
<222> LOCATION: (11)..(11)
<223> OTHER INFORMATION: n is i

<400> SEQUENCE: 126
tgactgtgga ngtcagagat ga                                              22

<210> SEQ ID NO 127
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer
<220> FEATURE:
<221> NAME/KEY: misc_feature
<222> LOCATION: (11)..(11)
<223> OTHER INFORMATION: n is i

<400> SEQUENCE: 127
tgactgtgga ngctagagat ga                                              22

<210> SEQ ID NO 128
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core

```
                                         hexamer
<220> FEATURE:
<221> NAME/KEY: misc_feature
<222> LOCATION: (11)..(11)
<223> OTHER INFORMATION: n is i

<400> SEQUENCE: 128
tgactgtgga ngccagagat ga                                              22

<210> SEQ ID NO 129
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 129
tgactgtggg ngttagagat ga                                              22

<210> SEQ ID NO 130
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 130
tgactgtggg ngtcagagat ga                                              22

<210> SEQ ID NO 131
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 131
tgactgtggg ngctagagat ga                                              22

<210> SEQ ID NO 132
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 132
```
tgactgtggg ngccagagat ga                                              22

<210> SEQ ID NO 133
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 133
tgactgtgaa ncttagagat ga                                              22

<210> SEQ ID NO 134
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 134
tgactgtgaa nctcagagat ga                                              22

<210> SEQ ID NO 135
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 135
tgactgtgaa ncctagagat ga                                              22

<210> SEQ ID NO 136
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 136
tgactgtgaa ncccagagat ga                                              22

<210> SEQ ID NO 137
<211> LENGTH: 22
<212> TYPE: DNA

```
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 137
tgactgtgag ncttagagat ga                                          22

<210> SEQ ID NO 138
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 138
tgactgtgag nctcagagat ga                                          22

<210> SEQ ID NO 139
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 139
tgactgtgag ncctagagat ga                                          22

<210> SEQ ID NO 140
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 140
tgactgtgag ncccagagat ga                                          22

<210> SEQ ID NO 141
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
```

```
<222> LOCATION: (11)..(11)
<223> OTHER INFORMATION: n is i

<400> SEQUENCE: 141
tgactgtgga ncttagagat ga                                          22

<210> SEQ ID NO 142
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 142
tgactgtgga nctcagagat ga                                          22

<210> SEQ ID NO 143
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 143
tgactgtgga ncctagagat ga                                          22

<210> SEQ ID NO 144
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 144
tgactgtgga ncccagagat ga                                          22

<210> SEQ ID NO 145
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 145
tgactgtggg ncttagagat ga                                          22
```

```
<210> SEQ ID NO 146
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 146
tgactgtggg nctcagagat ga                                            22

<210> SEQ ID NO 147
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 147
tgactgtggg ncctagagat ga                                            22

<210> SEQ ID NO 148
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 148
tgactgtggg ncccagagat ga                                            22

<210> SEQ ID NO 149
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 149
tgactgtgaa tgttagagat ga                                            22

<210> SEQ ID NO 150
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 150
```

```
tgactgtgaa tgtcagagat ga                                              22

<210> SEQ ID NO 151
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 151
tgactgtgaa tgctagagat ga                                              22

<210> SEQ ID NO 152
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 152
tgactgtgaa tgccagagat ga                                              22

<210> SEQ ID NO 153
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 153
tgactgtgag tgttagagat ga                                              22

<210> SEQ ID NO 154
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 154
tgactgtgag tgtcagagat ga                                              22

<210> SEQ ID NO 155
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 155
tgactgtgag tgctagagat ga                                              22

<210> SEQ ID NO 156
<211> LENGTH: 22
<212> TYPE: DNA
<213> ORGANISM: Artificial Sequence
<220> FEATURE:
```

```
<223> OTHER INFORMATION: synthetic immune modulatory sequence (IMS)
      oligonucleotide with 5' and 3' flanking sequences around core
      hexamer

<400> SEQUENCE: 156
tgactgtgag tgccagagat ga                                              22

<210> SEQ ID NO 157
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 157
tgactgtgga tgttagagat ga                                              22

<210> SEQ ID NO 158
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 158
tgactgtgga tgtcagagat ga                                              22

<210> SEQ ID NO 159
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 159
tgactgtgga tgctagagat ga                                              22

<210> SEQ ID NO 160
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 160
tgactgtgga tgccagagat ga                                              22

<210> SEQ ID NO 161
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 161
tgactgtggg tgttagagat ga                                              22
```

```
<210> SEQ ID NO 162
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 162
tgactgtggg tgtcagagat ga                                              22

<210> SEQ ID NO 163
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 163
tgactgtggg tgctagagat ga                                              22

<210> SEQ ID NO 164
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 164
tgactgtggg tgccagagat ga                                              22

<210> SEQ ID NO 165
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 165
tgactgtgaa tattagagat ga                                              22

<210> SEQ ID NO 166
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 166
tgactgtgaa tatcagagat ga                                              22

<210> SEQ ID NO 167
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
```

```
<400> SEQUENCE: 167
tgactgtgaa tactagagat ga                                              22

<210> SEQ ID NO 168
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 168
tgactgtgaa taccagagat ga                                              22

<210> SEQ ID NO 169
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 169
tgactgtgag tattagagat ga                                              22

<210> SEQ ID NO 170
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 170
tgactgtgag tatcagagat ga                                              22

<210> SEQ ID NO 171
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 171
tgactgtgag tactagagat ga                                              22

<210> SEQ ID NO 172
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 172
tgactgtgag taccagagat ga                                              22

<210> SEQ ID NO 173
<211> LENGTH: 22
<212> TYPE: DNA
<213> ORGANISM: Artificial Sequence
```

-continued

```
<220> FEATURE:
<223> OTHER INFORMATION: synthetic immune modulatory sequence (IMS)
      oligonucleotide with 5' and 3' flanking sequences around core
      hexamer

<400> SEQUENCE: 173
tgactgtgga tattagagat ga                                              22

<210> SEQ ID NO 174
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 174
tgactgtgga tatcagagat ga                                              22

<210> SEQ ID NO 175
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 175
tgactgtgga tactagagat ga                                              22

<210> SEQ ID NO 176
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 176
tgactgtgga taccagagat ga                                              22

<210> SEQ ID NO 177
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 177
tgactgtggg tattagagat ga                                              22

<210> SEQ ID NO 178
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 178
tgactgtggg tatcagagat ga                                              22
```

<210> SEQ ID NO 179
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 179
tgactgtggg tactagagat ga                                              22

<210> SEQ ID NO 180
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 180
tgactgtggg taccagagat ga                                              22

<210> SEQ ID NO 181
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 181
tgactgtgaa cgttagagat ga                                              22

<210> SEQ ID NO 182
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 182
tgactgtgaa ccttagagat ga                                              22

<210> SEQ ID NO 183
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 183
tgactgtgat gcttagagat ga                                              22

<210> SEQ ID NO 184
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

```
<400> SEQUENCE: 184
tgactgtgat gctcagagat ga                                              22

<210> SEQ ID NO 185
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 185
tgactgtgat gcctagagat ga                                              22

<210> SEQ ID NO 186
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 186
tgactgtgat gcccagagat ga                                              22

<210> SEQ ID NO 187
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 187
tgactgtgac gcttagagat ga                                              22

<210> SEQ ID NO 188
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 188
tgactgtgac gctcagagat ga                                              22

<210> SEQ ID NO 189
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 189
tgactgtgac gcctagagat ga                                              22

<210> SEQ ID NO 190
<211> LENGTH: 22
<212> TYPE: DNA
```

```
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 190
tgactgtgac gcccagagat ga                                              22

<210> SEQ ID NO 191
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 191
tgactgtggt gcttagagat ga                                              22

<210> SEQ ID NO 192
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 192
tgactgtggt gctcagagat ga                                              22

<210> SEQ ID NO 193
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 193
tgactgtggt gcctagagat ga                                              22

<210> SEQ ID NO 194
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 194
tgactgtggt gcccagagat ga                                              22

<210> SEQ ID NO 195
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 195
tgactgtggc gcttagagat ga                                              22
```

<210> SEQ ID NO 196
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 196
tgactgtggc gctcagagat ga                                              22

<210> SEQ ID NO 197
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 197
tgactgtggc gcctagagat ga                                              22

<210> SEQ ID NO 198
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 198
tgactgtggc gcccagagat ga                                              22

<210> SEQ ID NO 199
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 199
tgactgtgat ggttagagat ga                                              22

<210> SEQ ID NO 200
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 200
tgactgtgat ggtcagagat ga                                              22

<210> SEQ ID NO 201
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 201
tgactgtgat ggctagagat ga                                              22

<210> SEQ ID NO 202
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 202
tgactgtgat ggccagagat ga                                              22

<210> SEQ ID NO 203
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 203
tgactgtgac ggttagagat ga                                              22

<210> SEQ ID NO 204
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 204
tgactgtgac ggtcagagat ga                                              22

<210> SEQ ID NO 205
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 205
tgactgtgac ggctagagat ga                                              22

<210> SEQ ID NO 206
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 206
tgactgtgac ggccagagat ga                                              22

<210> SEQ ID NO 207
<211> LENGTH: 22

```
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 207
tgactgtggt ggttagagat ga                                              22

<210> SEQ ID NO 208
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 208
tgactgtggt ggtcagagat ga                                              22

<210> SEQ ID NO 209
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 209
tgactgtggt ggctagagat ga                                              22

<210> SEQ ID NO 210
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 210
tgactgtggt ggccagagat ga                                              22

<210> SEQ ID NO 211
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 211
tgactgtggc ggttagagat ga                                              22

<210> SEQ ID NO 212
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 212
```
tgactgtggc ggtcagagat ga                                              22

<210> SEQ ID NO 213
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 213
tgactgtggc ggctagagat ga                                              22

<210> SEQ ID NO 214
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 214
tgactgtggc ggccagagat ga                                              22

<210> SEQ ID NO 215
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 215
tgactgtgat agttagagat ga                                              22

<210> SEQ ID NO 216
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 216
tgactgtgat agtcagagat ga                                              22

<210> SEQ ID NO 217
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 217
tgactgtgat agctagagat ga                                              22

<210> SEQ ID NO 218
<211> LENGTH: 22
<212> TYPE: DNA
<213> ORGANISM: Artificial Sequence
<220> FEATURE:
<223> OTHER INFORMATION: synthetic immune modulatory sequence (IMS)

oligonucleotide with 5' and 3' flanking sequences around core
hexamer

<400> SEQUENCE: 218
tgactgtgat agccagagat ga                                              22

<210> SEQ ID NO 219
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 219
tgactgtgac agttagagat ga                                              22

<210> SEQ ID NO 220
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 220
tgactgtgac agtcagagat ga                                              22

<210> SEQ ID NO 221
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 221
tgactgtgac agctagagat ga                                              22

<210> SEQ ID NO 222
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 222
tgactgtgac agccagagat ga                                              22

<210> SEQ ID NO 223
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 223
tgactgtggt agttagagat ga                                              22

<210> SEQ ID NO 224

```
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 224
tgactgtggt agtcagagat ga                                              22

<210> SEQ ID NO 225
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 225
tgactgtggt agctagagat ga                                              22

<210> SEQ ID NO 226
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 226
tgactgtggt agccagagat ga                                              22

<210> SEQ ID NO 227
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 227
tgactgtggc agttagagat ga                                              22

<210> SEQ ID NO 228
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 228
tgactgtggc agtcagagat ga                                              22

<210> SEQ ID NO 229
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 229
```

```
tgactgtggc agctagagat ga                                               22
```

<210> SEQ ID NO 230
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 230

```
tgactgtggc agccagagat ga                                               22
```

<210> SEQ ID NO 231
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 231

```
tgactgtgat ngttagagat ga                                               22
```

<210> SEQ ID NO 232
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 232

```
tgactgtgat ngtcagagat ga                                               22
```

<210> SEQ ID NO 233
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 233

```
tgactgtgat ngctagagat ga                                               22
```

<210> SEQ ID NO 234
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core

```
                                          hexamer
<220> FEATURE:
<221> NAME/KEY: misc_feature
<222> LOCATION: (11)..(11)
<223> OTHER INFORMATION: n is i

<400> SEQUENCE: 234
tgactgtgat ngccagagat ga                                              22

<210> SEQ ID NO 235
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 235
tgactgtgac ngttagagat ga                                              22

<210> SEQ ID NO 236
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 236
tgactgtgac ngtcagagat ga                                              22

<210> SEQ ID NO 237
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 237
tgactgtgac ngctagagat ga                                              22

<210> SEQ ID NO 238
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 238
```
tgactgtgac ngccagagat ga                                              22

<210> SEQ ID NO 239
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 239
tgactgtggt ngttagagat ga                                              22

<210> SEQ ID NO 240
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 240
tgactgtggt ngtcagagat ga                                              22

<210> SEQ ID NO 241
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 241
tgactgtggt ngctagagat ga                                              22

<210> SEQ ID NO 242
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 242
tgactgtggt ngccagagat ga                                              22

<210> SEQ ID NO 243
<211> LENGTH: 22
<212> TYPE: DNA

```
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 243
tgactgtggc ngttagagat ga                                              22

<210> SEQ ID NO 244
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 244
tgactgtggc ngtcagagat ga                                              22

<210> SEQ ID NO 245
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 245
tgactgtggc ngctagagat ga                                              22

<210> SEQ ID NO 246
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 246
tgactgtggc ngccagagat ga                                              22

<210> SEQ ID NO 247
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
```

```
<222> LOCATION: (11)..(11)
<223> OTHER INFORMATION: n is i

<400> SEQUENCE: 247
tgactgtgat ncttagagat ga                                          22

<210> SEQ ID NO 248
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 248
tgactgtgat nctcagagat ga                                          22

<210> SEQ ID NO 249
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 249
tgactgtgat ncctagagat ga                                          22

<210> SEQ ID NO 250
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 250
tgactgtgat ncccagagat ga                                          22

<210> SEQ ID NO 251
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 251
tgactgtgac ncttagagat ga                                          22
```

```
<210> SEQ ID NO 252
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 252
tgactgtgac nctcagagat ga                                           22

<210> SEQ ID NO 253
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 253
tgactgtgac ncctagagat ga                                           22

<210> SEQ ID NO 254
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 254
tgactgtgac ncccagagat ga                                           22

<210> SEQ ID NO 255
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 255
tgactgtggt ncttagagat ga                                           22

<210> SEQ ID NO 256
<211> LENGTH: 22
<212> TYPE: DNA
<213> ORGANISM: Artificial Sequence
<220> FEATURE:
<223> OTHER INFORMATION: synthetic immune modulatory sequence (IMS)
```

```
oligonucleotide with 5' and 3' flanking sequences around core
     hexamer
<220> FEATURE:
<221> NAME/KEY: misc_feature
<222> LOCATION: (11)..(11)
<223> OTHER INFORMATION: n is i

<400> SEQUENCE: 256
tgactgtggt nctcagagat ga                                              22

<210> SEQ ID NO 257
<211> LENGTH: 22
<212> TYPE: DNA
<213> ORGANISM: Artificial Sequence
<220> FEATURE:
<223> OTHER INFORMATION: synthetic immune modulatory sequence (IMS)
     oligonucleotide with 5' and 3' flanking sequences around core
     hexamer
<220> FEATURE:
<221> NAME/KEY: misc_feature
<222> LOCATION: (11)..(11)
<223> OTHER INFORMATION: n is i

<400> SEQUENCE: 257
tgactgtggt ncctagagat ga                                              22

<210> SEQ ID NO 258
<211> LENGTH: 22
<212> TYPE: DNA
<213> ORGANISM: Artificial Sequence
<220> FEATURE:
<223> OTHER INFORMATION: synthetic immune modulatory sequence (IMS)
     oligonucleotide with 5' and 3' flanking sequences around core
     hexamer
<220> FEATURE:
<221> NAME/KEY: misc_feature
<222> LOCATION: (11)..(11)
<223> OTHER INFORMATION: n is i

<400> SEQUENCE: 258
tgactgtggt ncccagagat ga                                              22

<210> SEQ ID NO 259
<211> LENGTH: 22
<212> TYPE: DNA
<213> ORGANISM: Artificial Sequence
<220> FEATURE:
<223> OTHER INFORMATION: synthetic immune modulatory sequence (IMS)
     oligonucleotide with 5' and 3' flanking sequences around core
     hexamer
<220> FEATURE:
<221> NAME/KEY: misc_feature
<222> LOCATION: (11)..(11)
<223> OTHER INFORMATION: n is i

<400> SEQUENCE: 259
tgactgtggc ncttagagat ga                                              22

<210> SEQ ID NO 260
<211> LENGTH: 22
<212> TYPE: DNA
<213> ORGANISM: Artificial Sequence
<220> FEATURE:
<223> OTHER INFORMATION: synthetic immune modulatory sequence (IMS)
     oligonucleotide with 5' and 3' flanking sequences around core
     hexamer
<220> FEATURE:
<221> NAME/KEY: misc_feature
<222> LOCATION: (11)..(11)
<223> OTHER INFORMATION: n is i
```

```
<400> SEQUENCE: 260
tgactgtggc nctcagagat ga                                              22

<210> SEQ ID NO 261
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 261
tgactgtggc ncctagagat ga                                              22

<210> SEQ ID NO 262
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is i

<400> SEQUENCE: 262
tgactgtggc ncccagagat ga                                              22

<210> SEQ ID NO 263
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 263
tgactgtgat tgttagagat ga                                              22

<210> SEQ ID NO 264
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 264
tgactgtgat tgtcagagat ga                                              22

<210> SEQ ID NO 265
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 265
```

```
tgactgtgat tgctagagat ga                                              22

<210> SEQ ID NO 266
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 266
tgactgtgat tgccagagat ga                                              22

<210> SEQ ID NO 267
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 267
tgactgtgac tgttagagat ga                                              22

<210> SEQ ID NO 268
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 268
tgactgtgac tgtcagagat ga                                              22

<210> SEQ ID NO 269
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 269
tgactgtgac tgctagagat ga                                              22

<210> SEQ ID NO 270
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 270
tgactgtgac tgccagagat ga                                              22

<210> SEQ ID NO 271
<211> LENGTH: 22
<212> TYPE: DNA
<213> ORGANISM: Artificial Sequence
<220> FEATURE:
```

```
<223> OTHER INFORMATION: synthetic immune modulatory sequence (IMS)
      oligonucleotide with 5' and 3' flanking sequences around core
      hexamer

<400> SEQUENCE: 271
tgactgtggt tgttagagat ga                                              22

<210> SEQ ID NO 272
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 272
tgactgtggt tgtcagagat ga                                              22

<210> SEQ ID NO 273
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 273
tgactgtggt tgctagagat ga                                              22

<210> SEQ ID NO 274
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 274
tgactgtggt tgccagagat ga                                              22

<210> SEQ ID NO 275
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 275
tgactgtggc tgttagagat ga                                              22

<210> SEQ ID NO 276
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 276
tgactgtggc tgtcagagat ga                                              22
```

```
<210> SEQ ID NO 277
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 277
tgactgtggc tgctagagat ga                                              22

<210> SEQ ID NO 278
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 278
tgactgtggc tgccagagat ga                                              22

<210> SEQ ID NO 279
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 279
tgactgtgat tattagagat ga                                              22

<210> SEQ ID NO 280
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 280
tgactgtgat tatcagagat ga                                              22

<210> SEQ ID NO 281
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 281
tgactgtgat tactagagat ga                                              22

<210> SEQ ID NO 282
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer
```

```
<400> SEQUENCE: 282
tgactgtgat taccagagat ga                                              22

<210> SEQ ID NO 283
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 283
tgactgtgac tattagagat ga                                              22

<210> SEQ ID NO 284
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 284
tgactgtgac tatcagagat ga                                              22

<210> SEQ ID NO 285
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 285
tgactgtgac tactagagat ga                                              22

<210> SEQ ID NO 286
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 286
tgactgtgac taccagagat ga                                              22

<210> SEQ ID NO 287
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 287
tgactgtggt tattagagat ga                                              22

<210> SEQ ID NO 288
<211> LENGTH: 22
<212> TYPE: DNA
<213> ORGANISM: Artificial Sequence
```

```
<220> FEATURE:
<223> OTHER INFORMATION: synthetic immune modulatory sequence (IMS)
      oligonucleotide with 5' and 3' flanking sequences around core
      hexamer

<400> SEQUENCE: 288
tgactgtggt tatcagagat ga                                              22

<210> SEQ ID NO 289
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 289
tgactgtggt tactagagat ga                                              22

<210> SEQ ID NO 290
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 290
tgactgtggt taccagagat ga                                              22

<210> SEQ ID NO 291
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 291
tgactgtggc tattagagat ga                                              22

<210> SEQ ID NO 292
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 292
tgactgtggc tatcagagat ga                                              22

<210> SEQ ID NO 293
<211> LENGTH: 22
<212> TYPE: DNA
<213> ORGANISM: Artificial Sequence
<220> FEATURE:
<223> OTHER INFORMATION: synthetic immune modulatory sequence (IMS)
      oligonucleotide with 5' and 3' flanking sequences around core
      hexamer

<400> SEQUENCE: 293
tgactgtggc tactagagat ga                                              22
```

<210> SEQ ID NO 294
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 294
tgactgtggc taccagagat ga                                              22

<210> SEQ ID NO 295
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 295
tgactgtgat cgttagagat ga                                              22

<210> SEQ ID NO 296
<211> LENGTH: 22
<212> TYPE: DNA
<213> ORGANISM: Artificial Sequence
<220> FEATURE:
<223> OTHER INFORMATION: synthetic immune modulatory sequence (IMS) oligonucleotide with 5' and 3' flanking sequences around core hexamer

<400> SEQUENCE: 296
tgactgtgac cgttagagat ga                                              22

<210> SEQ ID NO 297
<211> LENGTH: 2999
<212> TYPE: DNA
<213> ORGANISM: Artificial Sequence
<220> FEATURE:
<223> OTHER INFORMATION: pVAX1 plasmid vector

<400> SEQUENCE: 297
gactcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
ctatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccactag tccagtgtgg tggaattctg cagatatcca gcacagtggc     780
ggccgctcga gtctagaggg cccgtttaaa cccgctgatc agcctcgact gtgccttcta     840

```
gttgccagcc atctgttgtt tgcccctccc ccgtgccttc cttgaccctg gaaggtgcca    900
ctcccactgt cctttcctaa taaaatgagg aaattgcatc gcattgtctg agtaggtgtc    960
attctattct gggggtggg gtggggcagg acagcaaggg ggaggattgg gaagacaata    1020
gcaggcatgc tggggatgcg gtgggctcta tggcttctac tgggcggttt tatggacagc   1080
aagcgaaccg gaattgccag ctggggcgcc tctggtaag gttgggaagc cctgcaaagt    1140
aaactggatg gctttctcgc cgccaaggat ctgatggcgc aggggatcaa gctctgatca   1200
agagacagga tgaggatcgt ttcgcatgat tgaacaagat ggattgcacg caggttctcc   1260
ggccgcttgg gtggagaggc tattcggcta tgactgggca caacagacaa tcggctgctc   1320
tgatgccgcc gtgttccggc tgtcagcgca ggggcgcccg gttcttttg tcaagaccga   1380
cctgtccggt gccctgaatg aactgcaaga cgaggcagcg cggctatcgt ggctggccac   1440
gacgggcgtt ccttgcgcag ctgtgctcga cgttgtcact gaagcgggaa gggactggct   1500
gctattgggc gaagtgccgg ggcaggatct cctgtcatct caccttgctc ctgccgagaa   1560
agtatccatc atggctgatg caatgcggcg gctgcatacg cttgatccgg ctacctgccc   1620
attcgaccac caagcgaaac atcgcatcga gcgagcacgt actcggatgg aagccggtct   1680
tgtcgatcag gatgatctgg acgaagagca tcaggggctc gcgccagccg aactgttcgc   1740
caggctcaag gcgagcatgc ccgacggcga ggatctcgtc gtgacccatg gcgatgcctg   1800
cttgccgaat atcatggtgg aaaatggccg cttttctgga ttcatcgact gtggccggct   1860
gggtgtggcg gaccgctatc aggacatagc gttggctacc cgtgatattg ctgaagagct   1920
tggcggcgaa tgggctgacc gcttcctcgt gctttacggt atcgccgctc ccgattcgca   1980
gcgcatcgcc ttctatcgcc ttcttgacga gttcttctga attattaacg cttacaattt   2040
cctgatgcgg tattttctcc ttacgcatct gtgcggtatt tcacaccgca tacaggtggc   2100
acttttcggg gaaatgtgcg cggaacccct atttgtttat ttttctaaat acattcaaat   2160
atgtatccgc tcatgagaca ataaccctga taaatgcttc aataatagca cgtgctaaaa   2220
cttcattttt aatttaaaag gatctaggtg aagatccttt ttgataatct catgaccaaa   2280
atcccttaac gtgagttttc gttccactga gcgtcagacc ccgtagaaaa gatcaaagga   2340
tcttcttgag atcctttttt tctgcgcgta atctgctgct tgcaaacaaa aaaaccaccg   2400
ctaccagcgg tggtttgttt gccggatcaa gagctaccaa ctcttttcc gaaggtaact    2460
ggcttcagca gagcgcagat accaaatact gtccttctag tgtagccgta gttaggccac   2520
cacttcaaga actctgtagc accgcctaca tacctcgctc tgctaatcct gttaccagtg   2580
gctgctgcca gtggcgataa gtcgtgtctt accgggttgg actcaagacg atagttaccg   2640
gataaggcgc agcggtcggg ctgaacgggg ggttcgtgca cacagcccag cttggagcga   2700
acgacctaca ccgaactgag atacctacag cgtgagctat gagaaagcgc cacgcttccc   2760
gaagggagaa aggcggacag gtatccggta agcggcaggg tcggaacagg agagcgcacg   2820
agggagcttc caggggggaaa cgcctggtat ctttatagtc ctgtcgggtt tcgccacctc   2880
tgacttgagc gtcgattttt gtgatgctcg tcagggggc ggagcctatg gaaaaacgcc    2940
agcaacgcgg cctttttacg gttcctgggc ttttgctggc cttttgctca catgttctt   2999
```

<210> SEQ ID NO 298
<211> LENGTH: 22
<212> TYPE: DNA
<213> ORGANISM: Artificial Sequence
<220> FEATURE:

-continued

```
<223> OTHER INFORMATION: synthetic immune modulatory sequence (IMS)
      oligonucleotide with 5' and 3' flanking sequences around core
      hexamer
<220> FEATURE:
<221> NAME/KEY: misc_feature
<222> LOCATION: (11)..(11)
<223> OTHER INFORMATION: n is any naturally occurring or synthetic
      nucleotide except c
<220> FEATURE:
<221> NAME/KEY: misc_feature
<222> LOCATION: (12)..(12)
<223> OTHER INFORMATION: n is any naturally occurring or synthetic
      nucleotide except g

<400> SEQUENCE: 298
tgactgtgry nnyyagagat ga                                              22
```